US008568982B2

(12) United States Patent
Raghunath et al.

(10) Patent No.: US 8,568,982 B2
(45) Date of Patent: Oct. 29, 2013

(54) METHODS OF NUCLEIC ACID SYNTHESIS USING PARTICULAR CROWDING AGENTS AND CONCENTRATIONS

(75) Inventors: Michael Raghunath, Singapore (SG); Ricardo Rodolfo Lareu, Singapore (SG); Subramhanya Karthik Harve, Singapore (SG)

(73) Assignee: National University of Singapore, Singapore (SG)

( * ) Notice: Subject to any disclaimer, the term of this patent is extended or adjusted under 35 U.S.C. 154(b) by 239 days.

(21) Appl. No.: 12/376,926

(22) PCT Filed: Aug. 10, 2007

(86) PCT No.: PCT/SG2007/000248
§ 371 (c)(1),
(2), (4) Date: Feb. 9, 2009

(87) PCT Pub. No.: WO2008/018839
PCT Pub. Date: Feb. 14, 2008

(65) Prior Publication Data
US 2010/0279283 A1 Nov. 4, 2010

Related U.S. Application Data

(60) Provisional application No. 60/836,374, filed on Aug. 9, 2006.

(51) Int. Cl.
C12Q 1/68 (2006.01)
C12P 19/34 (2006.01)

(52) U.S. Cl.
USPC .................. 435/6.12; 435/91.1; 435/91.2

(58) Field of Classification Search
USPC ........................................ 435/6, 91.1, 91.2
See application file for complete search history.

(56) References Cited

U.S. PATENT DOCUMENTS

| 4,582,802 | A | 4/1986 | Zimmerman et al. |
| 5,665,572 | A * | 9/1997 | Ikeda et al. .................. 435/91.2 |
| 5,972,603 | A | 10/1999 | Bedford et al. |
| 6,114,150 | A | 9/2000 | Weismann et al. |
| 6,300,073 | B1 | 10/2001 | Zhao et al. |
| 6,428,986 | B1 | 8/2002 | Lapidot et al. |
| 6,656,685 | B2 | 12/2003 | Utermohlen et al. |
| 6,787,305 | B1 | 9/2004 | Li et al. |
| 2003/0135030 | A1* | 7/2003 | Guttman et al. ............. 530/402 |
| 2004/0241713 | A1 | 12/2004 | Mirzabekov et al. |
| 2005/0112631 | A1* | 5/2005 | Piepenburg et al. .............. 435/6 |

FOREIGN PATENT DOCUMENTS

| WO | WO 94/18333 | 8/1994 |
| WO | WO 01/92501 A1 | 12/2001 |
| WO | WO 03/053647 A2 | 7/2003 |

OTHER PUBLICATIONS

Bambara R.A., et.al., "On the Processive Mechanism of *Escherichia coli* DNA Polymerase I", The Journal of Biological Chemistry, 1978, vol. 253(2):413-423.

Chebotareva N.A., et.al., "Biochemical Effects of Molecular Crowding", Biochemistry (Moscow), 2004, vol. 69(11):1239-1251.
Cheung M.S., et.al., "Molecular crowding enhances native state stability and refolding rates of globular proteins", Proc Natl Acad Sci, USA, Mar. 2005, vol. 102(13):4753-4758.
Chomczynski P. & Sacchi N., "Single-Step Method of RNA Isolation by Acid Guanidinium Thiocyanate-Phenol-Chloroform Extraction", Analytical Biochemistry, 1987, vol. 162:156-159.
Ellis R.J., "Macromolecular crowding: obvious but underappreciated", Trends in Biochemicai Sciences, Oct. 2001, vol. 26(10):597-604.
Gottlieb J., et.al., "The Herpes Simplex Virus Type 1 UL42 Gene Product: a Subunit of DNA Polymerase That Functions to Increase Processivity", Journal of Virology, Dec. 1990, vol. 64 (12):5976-5987.
Gronthos S., et.al., "Molecular and cellular characterisation of highly purified stromal stem cells derived from human bone marrow", Journal of Cell Science, 2003, vol. 116:1827-1835.
Kotewicz M.L., et.al., "Cloning and overexpression of Moloney murine leukemia virus reverse transcriptase in *Escherichia coli*", Gene, 1985, vol. 35:249-258.
Liu W. & Saint D.A., "A New Quantitative Method of Real Time Reverse Transcription Polymerase Chain Reaction Assay Based on Simulation of Polymerase Chain Reaction Kinetics", Analytical Biochemistry, 2002, vol. 302:52-59.
Livak K., "User Bulletin #2 ABI PRISM 7700 Sequence Detection System", Applied Biosystems, Dec. 11, 1997.
Minton A.P., "Protein folding: Thickening the broth", Current Biology, 2000, vol. 10:R97-R99.
Minton A.P., "The Influence of Macromolecular Crowding and Macromolecular Confinement on Biochemical Reactions in Physiological Media", The Journal of Biological Chemistry, Apr. 6, 2001, vol. 276(14):10577-10580.
Motz M., et.al., "Elucidation of an Archaeal Replication Protein Network to Generate Enhanced PCR Enzymes", The Journal of Biological Chemistry, May 3, 2002, vol. 277(18):16179-16188.
Ponchel F., et.al., "Real-time PCR based on SYBR-Green I fluorescence: An alternative to the TaqMan assay for a relative quantification of gene rearrangements, gene amplications and micro gene deletions", BMC Biotechnology, Oct. 2003, vol. 3(18).
Rasmussen R., et.al., "Quantitative PCR by Continuous Fluorescence Monitoring of a Double Strand DNA Specific Binding Dye", Biochemica, 1998, 2:8-11.
Schnell S. & Mendoza C., "Theoretical Description of the Polymerase Chain Reaction", Journal of Theoretical Biology, 1997, vol. 188:313-318.
Spiess A.N. & Ivell R., "A Highly Efficient Method for Long-Chain cDNA Synthesis Using Trehalose and Betaine", Analytical Biochemistry, 2002, vol. 301:168-174.

(Continued)

*Primary Examiner* — Kenneth Horlick
(74) *Attorney, Agent, or Firm* — Hamilton, Brook, Smith & Reynolds, P.C.

(57) ABSTRACT

The invention provides a method of nucleic acid synthesis and/or amplification, and/or of improving the efficiency, activity and/or stability of at least one nucleic acid-modifying enzyme, comprising carrying out the method in the presence of (a) at least one organic-based macromolecule having a molecular weight of 50 kDa to 500 kDa and neutral surface charge; or (b) at least one organic-based macromolecule of radius 2 to 50 nm and neutral surface charge. There is also provided a method of determining the optimum crowding conditions of macromolecule(s) in solution.

14 Claims, 36 Drawing Sheets

(56) References Cited

OTHER PUBLICATIONS

Spiess A.N., et.al., "Trehalose Is a Potent PCR Enhancer: Lowering of DNA Melting Temperature and Thermal Stabilization of Taq Polymerase by the Disaccharide Trehalose", Clinical Chemistry, 2004, vol. 50(7):1256-1259.

Tokuriki N., et.al., "Protein folding by the effects of macromolecular crowding", Protein Science, 2004, vol. 13:125-133.

Wenner J.R. & Bloomfield V.A., "Crowding Effects on EcoRV Kinetics and Binding", Biophysical Journal, Dec. 1999, vol. 77:3234-3241.

Zhou B.R. et.al., "Mixed macromolecular crowding accelerates the oxidative refolding of reduced, denatured lysozyme. Implications for Protein Folding in Intracellular Environments", The Journal of Biological Chemistry, Dec. 31, 2004, vol. 279(53):55109-55116.

Zimmerman S.B. & Minton A.P., "Macromolecular Crowding: Biochemical, Biophysical, and Physiological Consequences", Annual Review of Biophysics and Biomolecular Structure, 1993, vol. 22:27-65.

Guy R.A., et.al., "Real-Time PCR for Quantification of *Giardia* and *Cryptosporidium* in Environmental Water Samples and Sewage", Applied and Environmental Microbiology, Sep. 2003; vol. 69(9):5178-5185.

Zimmerman S.B. & Trach S.O., "Macromolecular crowding extends the range of conditions under which DNA polymerase is functional", Biochimica et Biophysica Acta, 1988, vol. 949 (3):297-304.

Zimmerman S.B. & Harrison B., "Macromolecular crowding increases binding of DNA polymerase to DNA: An adaptive effect", Proceedings of the National Academy of Sciences USA, Apr. 1987, vol. 84(7):1871-1875.

Li J.J. & Tan W., "Macromolecular Crowding Accelerates DNA Cleavage Reaction Catalyzed by DNA Nucleases", Polymer Preprints, 2002, vol. 43(1):712-713.

Zhang X.J. & Julin D.A., "Isolation and characterization of the C-terminal nuclease domain from the RecB protein of *Escherichia coli*", Nucleic Acids Research, 1999, vol. 27(21):4200-4207.

Ballantyne K.N., et.al., "Molecular crowding Increases the amplification success of multiple displacement amplification and short tandem repeat genotyping", Analytical Biochemistry, 2006, vol. 355(2):298-303.

Sasaki Y., et.al., "Effect of molecular crowding on DNA polymerase activity", Biotechnology Journal, 2006, vol. 1(4):440-446.

Nashimoto M., "Correct folding of a ribozyme induced by nonspecific macromolelcules", European Journal of Biochemistry, 2000, vol. 267(9):2738-2745.

Boyd A.C., "Turbo cloning: a fast, efficient method for cloning PCR products and other blunt-ended DNA fragments into plasmids", Nucleic Acids Research, 1993, vol. 21(4):817-821.

\* cited by examiner

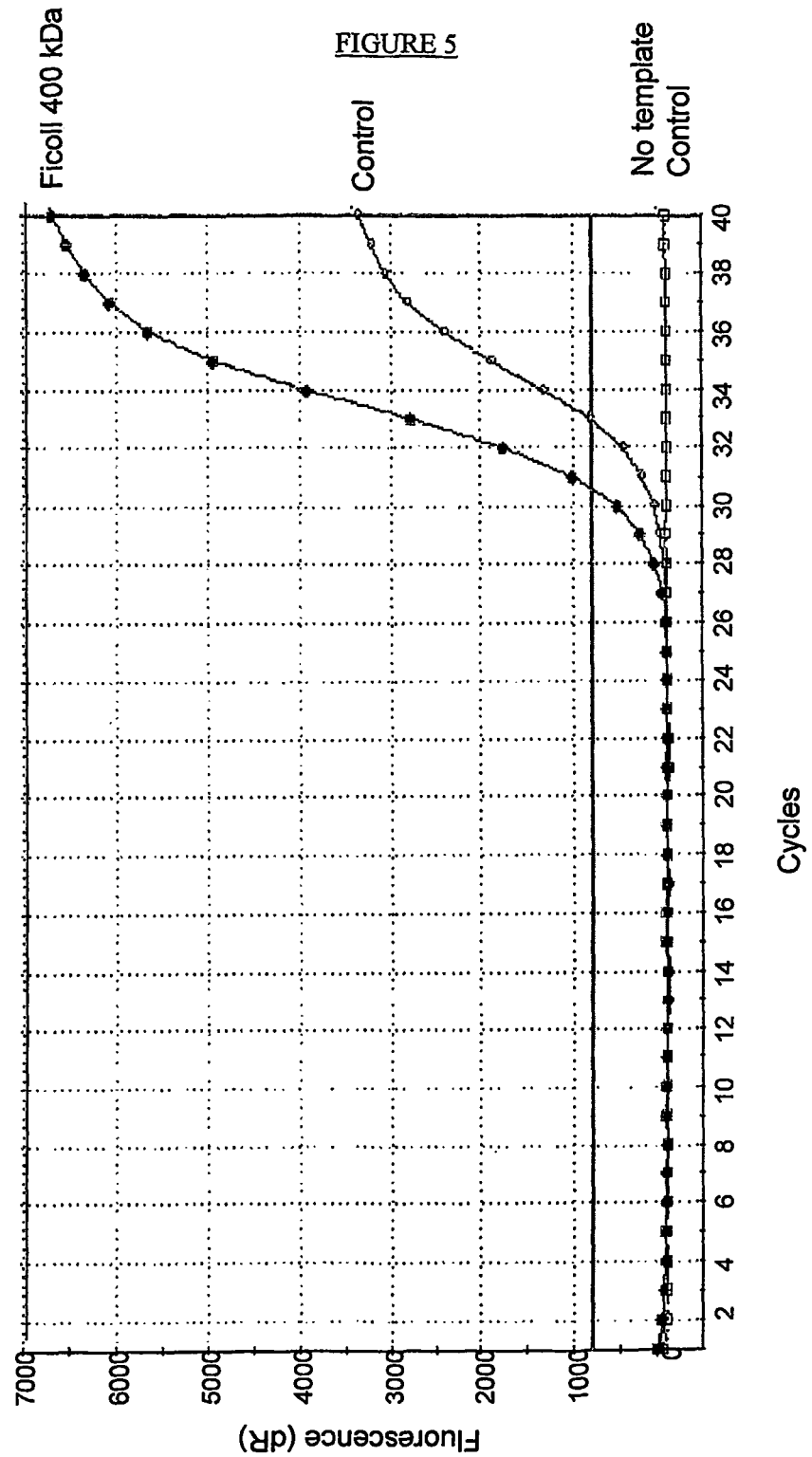

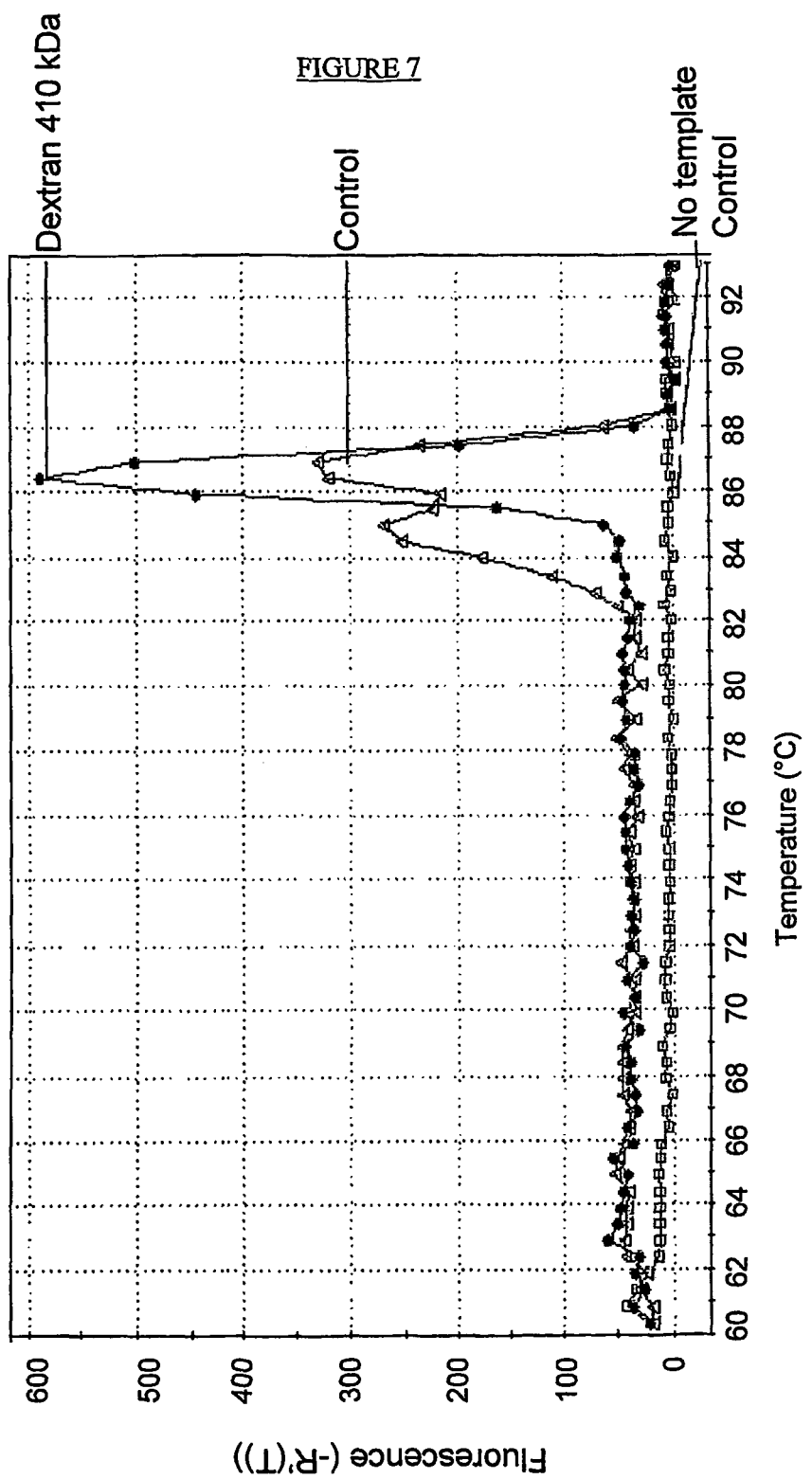

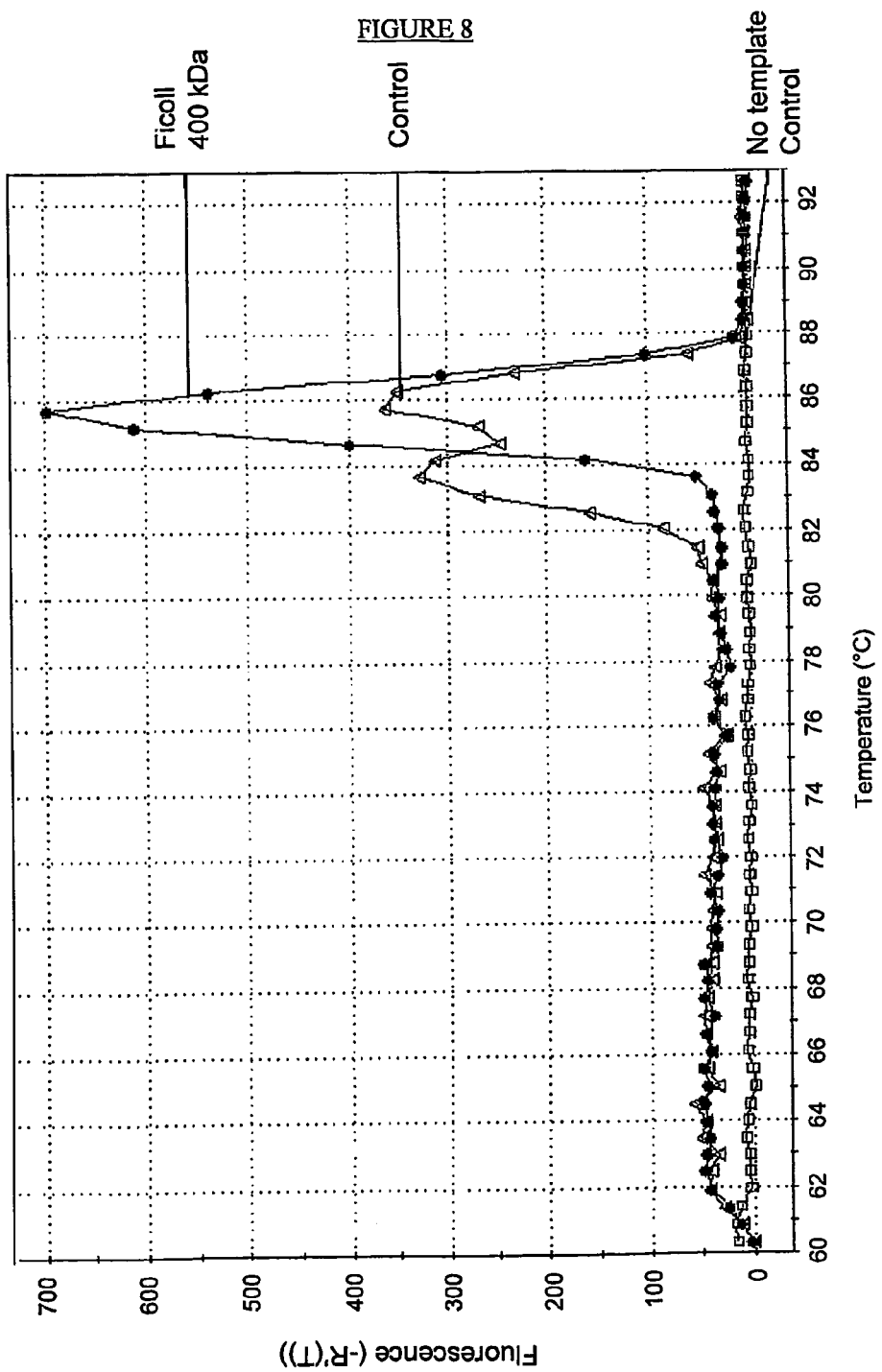

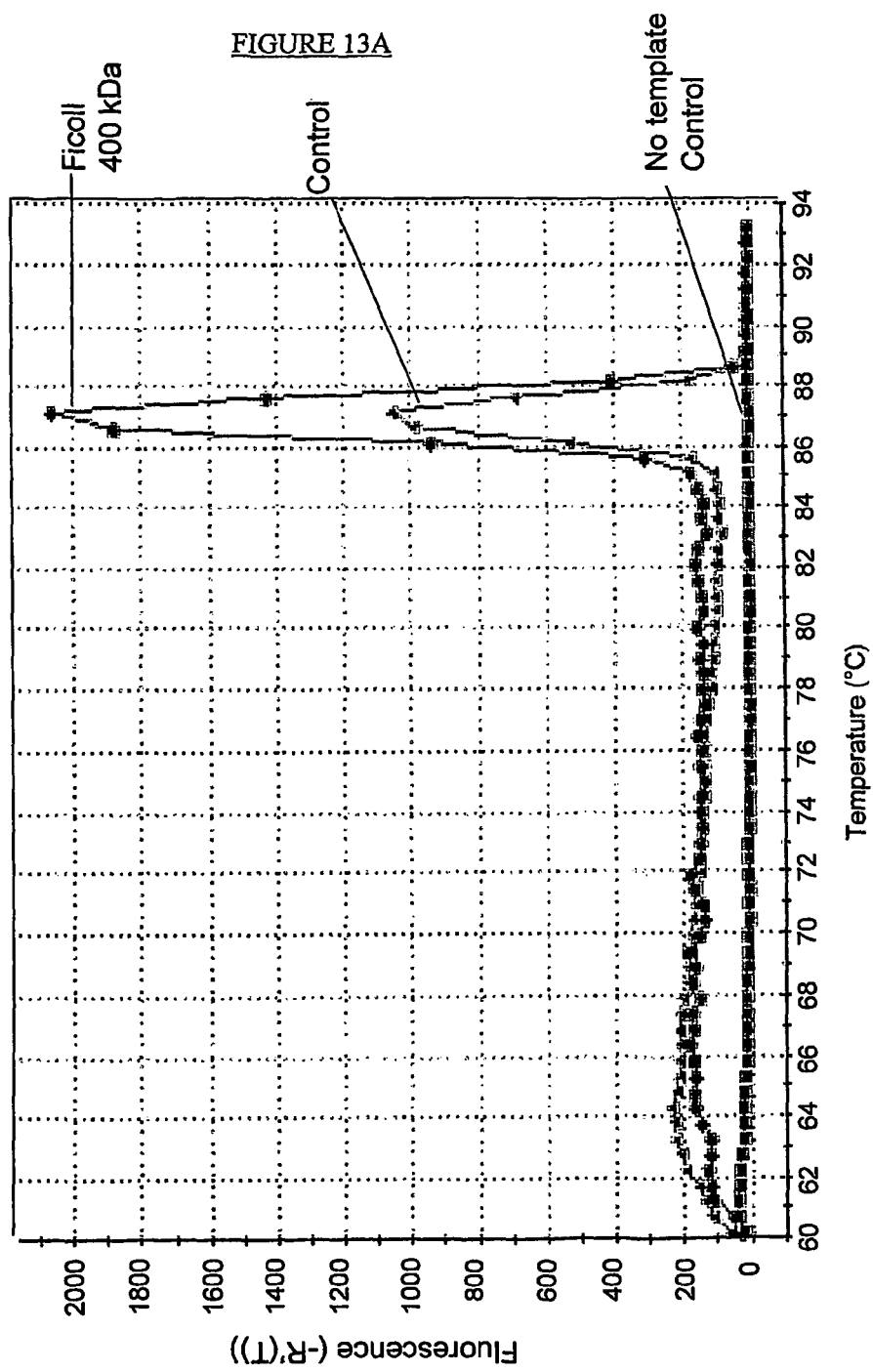

FIGURE 15c and d
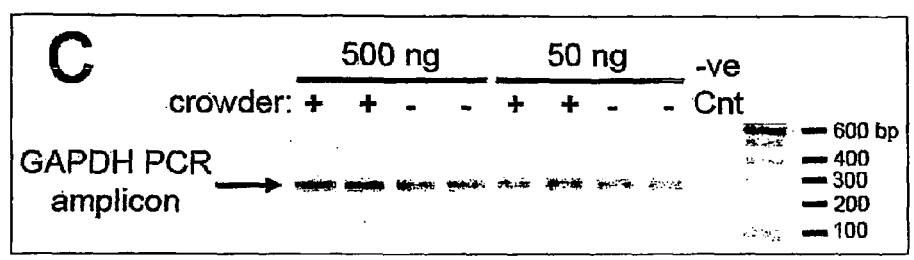
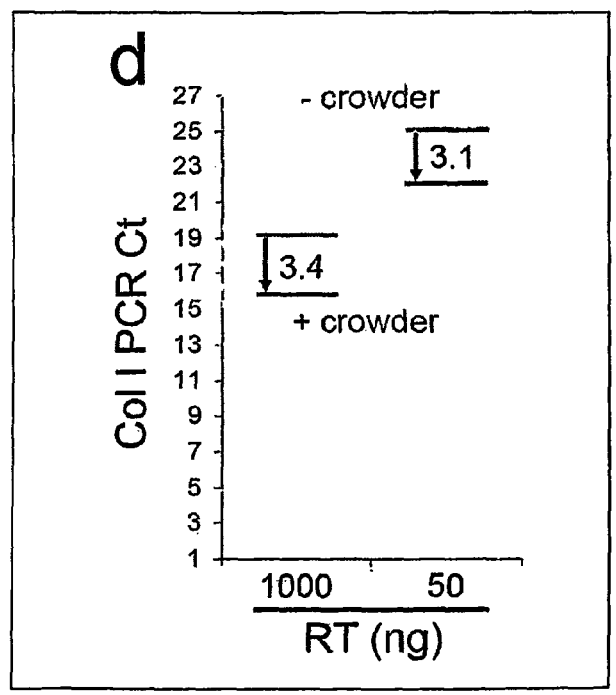

FIGURE 16d
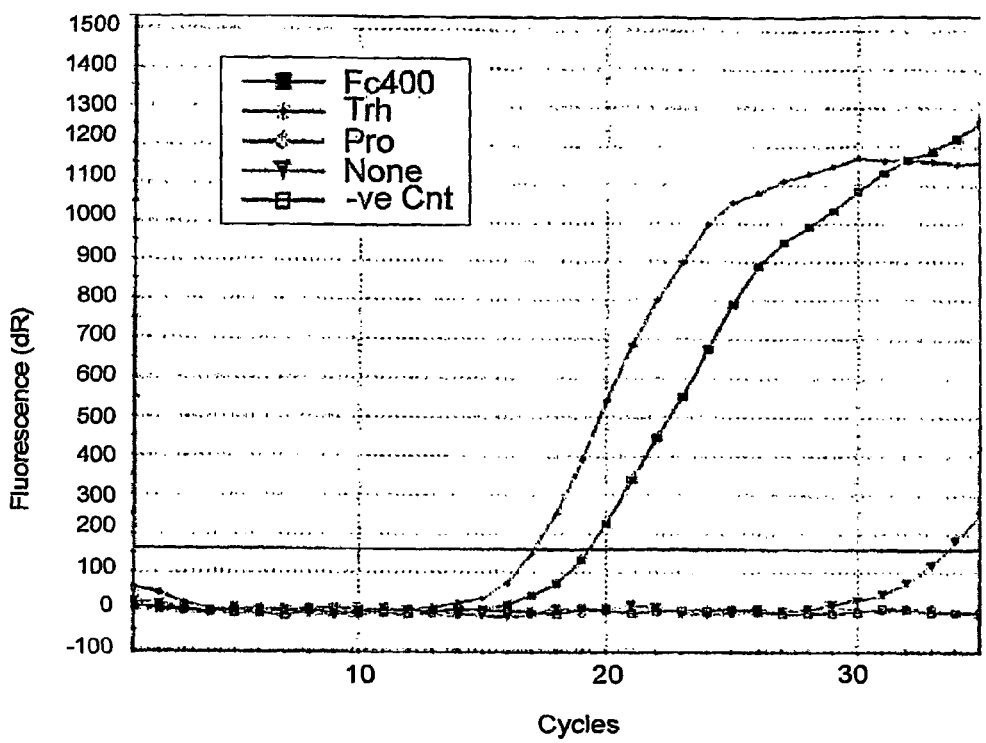
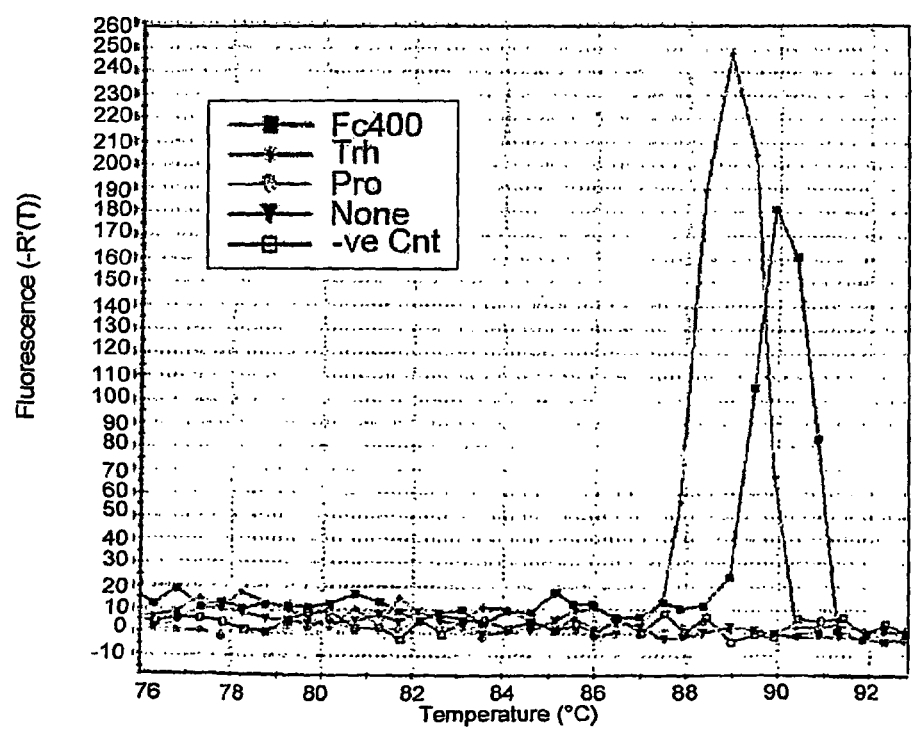

FIGURE 17a and b
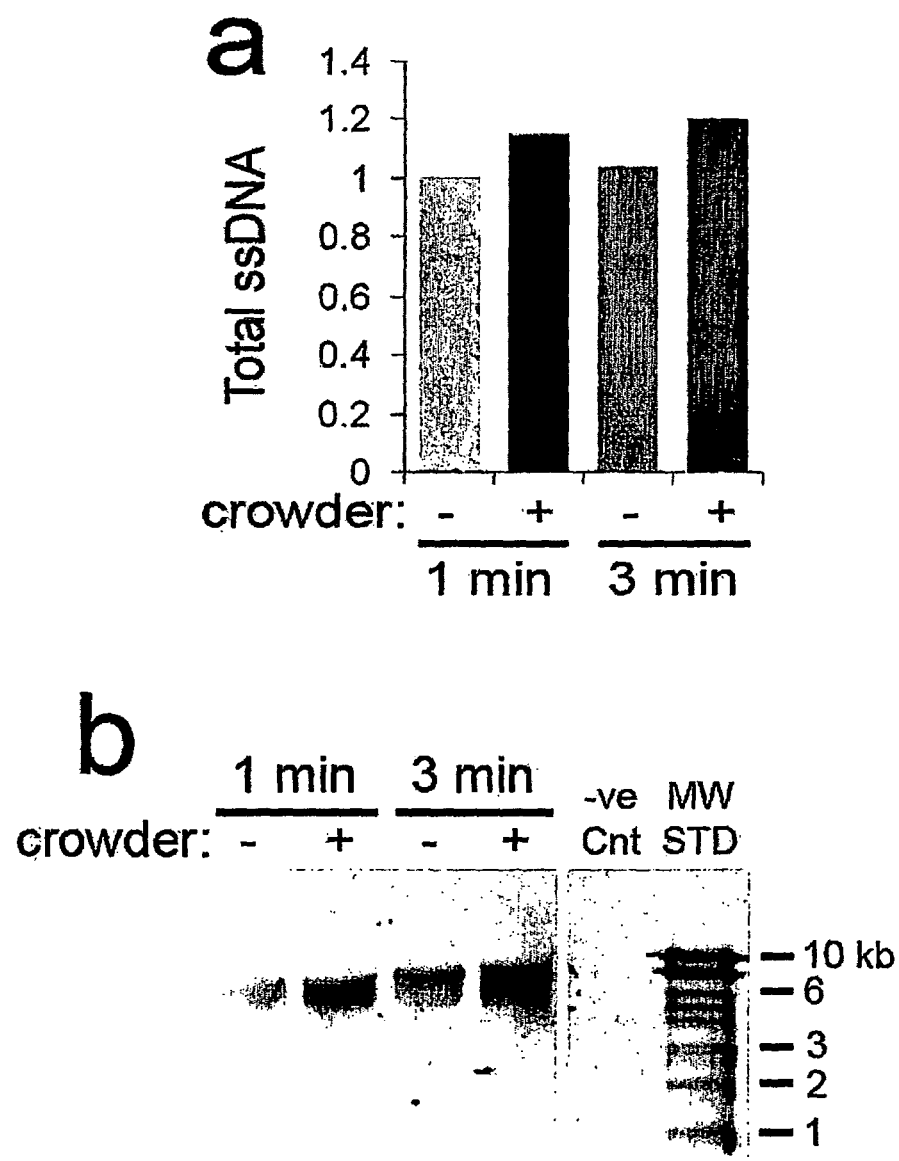

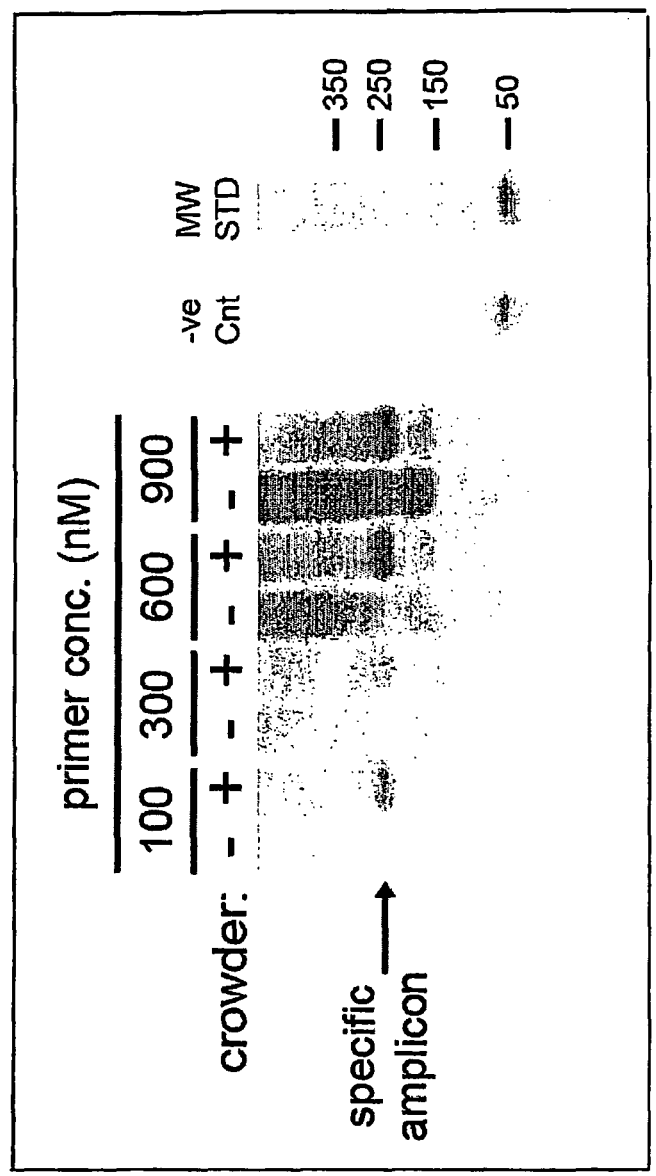

| Well | Well Name | Assay | Well Type | Threshold (dR) | Ct (dR) |
|---|---|---|---|---|---|
| C2 | UC1 | SYBR | Unknown | 347.684 | 21.21 |
| C4 | MMC1 | SYBR | Unknown | 347.684 | 18.78 |
| C9 | NTC1 | SYBR | Unknown | 347.684 | No Ct |
| D2 | PEG2.5 | SYBR | Unknown | 347.684 | 25.69 |
| D4 | PEG5 | SYBR | Unknown | 347.684 | 25.64 |
| D6 | PEG10 | SYBR | Unknown | 347.684 | 26.54 |
| D9 | NTC2 | SYBR | Unknown | 347.684 | No Ct |

SEQUENCE LISTING

<160> NUMBER OF SEQ ID NOS: 11

<210> SEQ ID NO 1
<211> LENGTH: 20
<212> TYPE: DNA

-continued

```
<213> ORGANISM: artificial
<220> FEATURE:
<223> OTHER INFORMATION: aP2 Forward primer

<400> SEQUENCE: 1
tactgggcca ggaatttgac                                              20

<210> SEQ ID NO 2
<211> LENGTH: 20
<212> TYPE: DNA
<213> ORGANISM: artificial
<220> FEATURE:
<223> OTHER INFORMATION: aP2 reverse primer

<400> SEQUENCE: 2
gtggaagtga cgaatttcat                                              20

<210> SEQ ID NO 3
<211> LENGTH: 20
<212> TYPE: DNA
<213> ORGANISM: artificial
<220> FEATURE:
<223> OTHER INFORMATION: GAPDH forward primer

<400> SEQUENCE: 3
gtccactggc gtcttcacca                                              20

<210> SEQ ID NO 4
<211> LENGTH: 20
<212> TYPE: DNA
<213> ORGANISM: artificial
<220> FEATURE:
<223> OTHER INFORMATION: GAPDH reverse primer

<400> SEQUENCE: 4
gtggcagtga tggcatggac                                              20

<210> SEQ ID NO 5
<211> LENGTH: 20
<212> TYPE: DNA
<213> ORGANISM: artificial
<220> FEATURE:
<223> OTHER INFORMATION: Collagen forward primer

<400> SEQUENCE: 5
agccagcaga tcgagaacat                                              20

<210> SEQ ID NO 6
<211> LENGTH: 20
<212> TYPE: DNA
<213> ORGANISM: artificial
<220> FEATURE:
<223> OTHER INFORMATION: Collagen reverse primer

<400> SEQUENCE: 6
tcttgtcctt ggggttcttg                                              20

<210> SEQ ID NO 7
<211> LENGTH: 18
<212> TYPE: DNA
<213> ORGANISM: artificial
<220> FEATURE:
<223> OTHER INFORMATION: M13 forward primer

<400> SEQUENCE: 7
ttgcttccgg tctggttc                                                18
```

```
<210> SEQ ID NO 8
<211> LENGTH: 18
<212> TYPE: DNA
<213> ORGANISM: artificial
<220> FEATURE:
<223> OTHER INFORMATION: M13 reverse primer

<400> SEQUENCE: 8
caccctcaga gccaccac                                                   18

<210> SEQ ID NO 9
<211> LENGTH: 20
<212> TYPE: DNA
<213> ORGANISM: artificial
<220> FEATURE:
<223> OTHER INFORMATION: Collagen I set 2 forward primer

<400> SEQUENCE: 9
gtgctaaagg tgccaatggt                                                 20

<210> SEQ ID NO 10
<211> LENGTH: 20
<212> TYPE: DNA
<213> ORGANISM: artificial
<220> FEATURE:
<223> OTHER INFORMATION: Collagen I set 2 reverse primer

<400> SEQUENCE: 10
ctcctcgctt tccttcctct                                                 20

<210> SEQ ID NO 11
<211> LENGTH: 17
<212> TYPE: DNA
<213> ORGANISM: artificial
<220> FEATURE:
<223> OTHER INFORMATION: M13 processivity primer

<400> SEQUENCE: 11
gtaaaacgac ggccagt                                                    17
```

METHODS OF NUCLEIC ACID SYNTHESIS USING PARTICULAR CROWDING AGENTS AND CONCENTRATIONS

FIELD OF THE INVENTION

The invention relates to the field of molecular biology, in particular to method(s) for molecular biology applications. For example, the method(s) according to the invention may be performed to synthesize, and/or amplify DNA and/or RNA using at least one nucleic acid-modifying enzyme for diagnostic, scientific and therapeutic purposes.

BACKGROUND OF THE INVENTION

A characteristic of the interiors of all cells is the high total concentration of macromolecules they contain. Such media are termed 'crowded' rather than 'concentrated' because, in general, no single macromolecular species occurs at high concentration but, taken together, show a volume occupancy of 20-30% of a given specific volume with a concentration close to 1 kg/l. Thus, these values define an approximate range of 200-300 g/l to be considered when using physical theory to calculate the consequences of crowding inside cells. As pointed out by Ellis (2001) and Minton (2000) crowding by macromolecules has both thermodynamic and kinetic effects on the properties of other macromolecules that are not generally appreciated (Minton 2000, Ellis 2001). Biological macromolecules such as enzymes have evolved to function inside such crowded environments. For example, the total concentration of protein and RNA inside bacteria like *E. coli* is in the range of 300-400 g/l. Macromolecular crowding is also termed the excluded volume effect, because its most basic characteristic is the mutual impenetrability of all solute molecules. This nonspecific steric repulsion is always present, regardless of any other attractive or repulsive interactions that might occur between the solute molecules. Thus, crowding cannot be avoided and is a hallmark of the intracellular milieu of all carbon-based life-forms on earth (reviewed in Ellis 2001). These resulting effects are so large that authorities in the field state that many estimates of enzyme catalyzed reaction rates and equilibria made with uncrowded solutions in the test tube differ by orders of magnitude from those of the same reactions operating under crowded conditions within cells (Ellis 2001).

Surprisingly, biochemists commonly study enzymatic reactions in solutions with a total macromolecular concentration of 1-10 g/l or less, in which crowding is negligible. In particular, all biochemical and enzymatic reactions relating to the amplification of RNA and DNA for diagnostic, scientific and therapeutic purposes are done in aqueous media under conditions that do not reflect the crowded environment of the organism they have been originally derived from. Of note, transcriptase and polymerases used in these systems are derived from thermophilic bacteria, most prominently *Thermus aquaticus* (Taq polymerase). These thermophilic bacteria reside and survive in hot pools and the enzymes derived from these organisms are employed under similar temperatures. The similarity of working conditions ends here, since these enzymes are put to work in aqueous solutions that do not emulate the crowded conditions in the bacteria they were originally derived from. Taq polymerase is a non-replicative type of DNA polymerase with an inherently low processivity compared to replicative type polymerases (T4 polymerase) which depend on specific peptides for their high processivity in vivo. Hence, to make Taq highly processive, it has to be "coaxed" to polymerise DNA in vitro for a detectable yield of PCR product that does not normally happen in vivo. In physiological conditions it was suggested that macromolecular crowding could enhance and/or maintain the integrity and/or stability of the DNA-Polymerase complex (Zimmermann and Harrison, 1987), although this was suggested only in reference to a T4 *E. coli* DNA polymerase binding to its target DNA at room temperature. Non-crowding approaches to increase processivity have revolved around complex procedures like engineering recombinant constructs to synthesise peptides that function as 'processivity factors' to enhance the binding of the enzyme to the target DNA in a "sliding clamp" mechanism which only partially resembles the normal physiology. Certain non-replicative polymerases such as the T7 DNA polymerase may have their processivity enhanced in the presence of proteins like thioredoxin, with the resultant T7-thioredoxin complex being able to function like the sliding clamp processor of replicative polymerases. A recent genetically engineered construct was suggested for synthesizing a peptide to enhance the binding between the polymerase and its target DNA (Wang et al, 2004) in a non-sequence dependent manner.

Though the current methods have been suggested to be effective, they do not address the underlying flaw of not observing that macromolecular crowding is an inherent physiological requirement for a highly processive DNA and RNA polymerization in vivo and hence in vitro.

Another aspect of in vitro DNA polymerization (as in a PCR) that has, not been currently addressed is the degree of fidelity of the polymerizing enzyme. This refers to the ability of the enzyme to incorporate the correct nucleotides complementary to the target sequence, so that minimal error is found in the final product. Current measures to enhance fidelity involve using thermostable polymerases armed with proofreading properties or having been engineered to carry them. This slows down the processivity of the enzyme automatically. Hence, ensuring simultaneous high processivity and high fidelity is still eluding current molecular biology techniques. Again, physiological in vivo DNA synthesis occurs in a highly crowded environment within the nucleus. In this situation, it has been theorized and biophysically shown that crowding favors correct DNA base-pair matching (the matchmaking effect) under physiological conditions (Goobes et al, 2003).

From a biophysical standpoint, the absence of crowding conditions in molecular biology techniques must lead to a variety of deficiencies when performing these extremely widely used procedures 1) PCR—Polymerase Chain Reaction
   without chaperones and protecting macromolecular crowders, folding of enzymes is compromised and they are, albeit sturdy, subjected to increased hydrolysis and decay towards the end of PCR cycles;
   the polymerizing enzymes are not optimally folded and perform poorly under high temperatures after several cycles, leading to poor yield (enzymatic exhaustion) and copying mistakes (reduced fidelity);
   the DNA-enzyme, DNA/DNA, RNA/DNA, RNA/RNA and related enzyme/protein complexes are less stable leading to suboptimal enzyme substrate kinetics compared to that in vivo;
   with more stringent conditions such as low copy number of target DNA, the detection ability with routine PCR conditions often fails;
   under stringent conditions of salt and temperature (large cycle number), the physical limits of the enzyme activity with regard to stability and processivity, are soon reached and hence the enzyme often fails to synthesize a complete complementary copy of the target. This results in production of too short PCR products;

the non-specific binding of primers to target is another problem with conventional PCRs that needs to be addressed by methods that select only the correctly bound primer-target duplex for further extension.

Prior art has tried to remedy above deficiencies by either modifying the amplifying enzymes (purification, recombinant expression, site directed mutagenesis (Gottlieb et al 1990 that describes a type 1 UL42 gene product which is a subunit of DNA polymerase that functions to increase processivity and WO0192501), or elaborate polymerization protocols (Wang et al. 2000). Only two approaches are documented that deal with the modification of the PCR reaction medium as such.

(A) The first approach is based on the principle of water structuring and preferential hydration due to compatible solutes, also known as osmolytes (U.S. Pat. Nos. 6,114,150A; 6,428,986; 6,300,073). This family comprises of several low molecular weight compounds that may be derived from carbohydrates (sucrose, trehalose), aminoacids (betaine, proline) or ectoines (homoectoine), all of which belong to the class of compatible solutes. The addition of the small molecule, trehalose, has been shown to be beneficial for PCR reactions with difficult target templates to perform leading to a higher yield. Trehalose, a sugar that is only found in certain lower organisms and actively synthesized in *Th. aquaticus*, is the original source for in vitro DNA polymerase (Taq polymerase). Thus, it is a natural component of the interior of the bacterial cell and known to belong to the group of compatible solutes (Spiess et al. 2002). that help these organisms to withstand extreme physico-chemical environments. However, trehalose with a molecular weight of 342 Da is far from being a macromolecule and thus, even in huge amounts cannot substitute them. In addition, a small but significant decrease in melting temperature of DNA or RNA hybrids in the presence of trehalose changes basic parameters of a typical PCR reaction as such. But this is supposedly the mechanism by which trehalose and the other like-compounds function, i.e by reducing the melting temperature of the target DNA. They have been mostly effective only when the target DNA or RNA has a significant secondary structure which could be linearized by such compounds that reduce their melting temperatures. However, this in itself limits the utility of these compounds to only a small sector of their applications on PCR.

(B) The second approach is also based on the concept of structuring water using engineered nanoparticles. The addition of nanoparticles (Neowater©) to the PCR mix as given in WO03053647. The nanoparticles are derived from metallic materials such as $BaTiO_3$, $Ba_2F_9O_{12}$, $WO_3$ in a top-down approach by breaking down 10 µm particles ending up in particles of a size distribution of 5-50 nm which retain their crystalline structure. The application of nanoparticles described in WO03053647 is claimed to work on the basis of structuring water and propagating alignment of water molecules. It is difficult to conceive how water molecules should be able maintain a structured state under PCR-typical high temperatures (close to boiling point of water) with its typical excess of Brownian molecular movements.

Chebotareva et al., 2004 reviewed the basic mechanisms by which the low molecular weight solutes (compatible solutes; osmolytes) effected a molecular crowding phenomenon which differs from the principle of macromolecular crowding and is the essential platform of our invention. Basically, molecular crowders work by structuring water (kosmotropes), whilst the macromolecular crowders function by excluding volume due to non-specific steric repulsive interactions. The implications of this basic fact are significant: while one has to use hundreds of milligrams of cosolutes per milliliter of solvent, macromolecules will be effective in micrograms to a few milligrams per ml of the solvent. This keeps the reaction conditions unchanged in terms of viscosity, pH and electrolyte concentrations which are key determinants of any biological enzymatic reaction. In fact, osmolytes in high concentrations can act as "molecular brakes" and reduce the rate of enzymatic reactions significantly (Spiess et al. 2004). Earlier work before the PCR era has shown that the addition of the macromolecules Ficoll 70 and Dextran T 70 to polymerase reactions from *E. coli* derived enzymes at 37° C. improved DNA enzyme binding and resulted in a longer survival of polymerase activity (Zimmermann & Harrison 1987). However, Ficoll 70 used alone was not resistant to the usual PCR temperatures. Further, Wenner and Bloomfield, 1999, have studied the possible crowding effect of Ficoll 70 of EcoRV cleavage. However, the results indicated that Ficoll had little effect on EcoRV reaction velocity.

2) Reverse Transcriptase Reaction

This is basically the most crucial step in all amplification procedures in order to create cDNA from extracted total mRNA. The extraction yield of this material is usually very limited, in particular if only a small collection of cells from needle biopsies of tissue or laser dissected portions from histological sections or forensic samples (saliva, fingerprints, blood, sperm) are available. The faithful and specific reverse transcription process will not only rule the amount and yield but also specificity and number of faulty copies generated (fidelity). Basically, the same shortcomings as listed for PCR apply. The current remedial action in prior art is to create high quality reverse transcripts of total mRNA are based on i) creation of novel and modified reverse transcriptases ii) modifications on the amplification procedures as such (template switching). With the advent of automation in RT-PCR, it has made the utility of enhancing this step of cDNA synthesis all the more crucial for obtaining a reasonable yield of second strand DNA downstream. With some recent reports of miniaturization of PCR using MEMS technology, application of principles to improve the environmental conditions of both reverse transcription for first strand cDNA synthesis and ds-cDNA has assumed prime importance.

However as yet, there are no reports of a combined approach to enhance simultaneously both the first and second strand cDNA syntheses.

SUMMARY OF THE INVENTION

The present invention addresses the problems above, and in particular to provide improved method(s) for molecular biology applications under optimum crowding conditions.

Accordingly, the present invention relates to a method of nucleic acid synthesis and/or amplification, and/or a method of improving the efficiency, activity and/or stability of at least one nucleic acid-modifying enzyme, the method comprising carrying out the method in the presence of at least one organic-based hydrophilic macromolecule of neutral surface change. In particular, there is provided a method of nucleic acid synthesis and/or amplification, and/or of improving the efficiency, activity and/or stability of at least one nucleic acid-modifying enzyme, the method comprising carrying out the method in the presence of (a) at least one organic-based hydrophilic macromolecule having a molecular weight of 50 kDa to 500 kDa and neutral surface charge, or (b) at least one organic-based hydrophilic macromolecule having a radius range of 2 to 50 nm and neutral surface change.

The macromolecule(s) according to the invention may have a radius range of 2 to 50 nm, in particular, a radius range of 5 to 20 nm. The macromolecule(s) according to the invention may have a molecular weight of 50 kDa to 500 kDa. In particular, the organic-based macromolecule according to the invention is a carbohydrate-based hydrophilic macromolecule. The carbohydrate-based macromolecule of the invention may be a polymer of glucose and/or sucrose. In particular, the macromolecule according to the invention may be a macromolecule selected from Ficoll 70, Ficoll 400, neutral dextran of 410 KDa, neutral dextran 670, PVP or a mixture thereof. More in particular, the carbohydrate-based macromolecule may be Ficoll 70 or Ficoll 400, or a mixture thereof. The total macromolecular concentration may be present at a concentration of 2.5-25 mg/ml, in particular 10-20 mg/ml. More in particular, the macromolecule may be Ficoll 70 present at a concentration of 2.5-25 mg/ml and/or Ficoll 400 at a concentration of 2.5-25 mg/ml, or a mixture thereof. The macromolecule according to the invention may have viscosity of less than 2 mPa·s. For example, a viscosity in the vicinity or about 1 mPa·s.

The nucleic acid-modifying enzyme used in the method according to any aspect of the invention may be is at least one polymerase and/or nuclease. Further, the method according any aspect of the invention may comprise the synthesis of complementary DNA (cDNA) from total RNA, mRNA and/or DNA in the presence of at least one polymerase. The polymerase may be at least one reverse transcriptase. In particular the method according to any aspect of the invention may be any amplification known in the art, for example PCR. In particular, RT-PCR.

There is also provided a kit for nucleic acid synthesis and/or amplification and/or for improving the efficiency, activity and/or stability of at least one nucleic acid-modifying enzyme, the kit comprising at least one organic-based hydrophilic macromolecule of neutral surface charge, and optionally an enzyme. In particular, the enzyme may be at least one nucleic acid-modifying enzyme, for example a polymerase or nuclease. However, the nucleic acid-modifying enzyme is not limited to polymerase or nuclease. In particular, the kit according to the invention may be a kit for nucleic acid synthesis, and/or amplification and/or for improving the efficiency, activity and/or stability of at least one nucleic acid-modifying enzyme, the kit comprising (a) at least one organic-based hydrophilic macromolecule of molecular weight 50 kDa to 500 kDa and neutral surface charge, or (b) at least one organic-based hydrophilic macromolecule of radius range of 2 to 50 nm and neutral surface charge; and optionally at least one nucleic acid-modifying enzyme. The macromolecule used in the kit of the invention is as defined throughout the whole content of the present application.

There is also provided at least one macromolecule mixture comprising at least two organic-based hydrophilic macromolecules, wherein each macromolecule, independently, is an organic-based hydrophilic macromolecule of neutral surface charge. More in particular, there is provided a macromolecule mixture comprising at least two organic-based hydrophilic macromolecules, wherein each macromolecule, independently, is: (a) at least one macromolecule having molecular weight 50 kDa to 500 kDa and neutral surface charge; and/or (b) at least one macromolecule having a radius range of 2 to 50 nm and neutral surface charge.

There is also provided a macromolecule solution for use in nucleic acid synthesis, and/or amplification and/or for improving the efficiency, activity and/or stability of an enzyme, the solution comprising at least one macromolecule or a mixture of macromolecules as defined throughout the whole content of the present application.

There is also provided a method of preparing a macromolecule solution for use in nucleic acid synthesis, and/or amplification and/or for improving the efficiency, activity and/or stability of at least one nucleic acid-modifying enzyme, comprising preparing a solution comprising at least one macromolecule or a mixture of macromolecules as defined throughout the whole content of the present application. In particular, the macromolecule(s) solution may have a viscosity of less than 2 mPa·s, more in particular, a viscosity of about 1 mPa·s.

According to another aspect, the invention also provides a method of nucleic acid digestion comprising carrying out the method in the presence of at least one nuclease and at least one organic-based hydrophilic macromolecule of neutral surface charge. In particular, there is provided a method of nucleic acid digestion comprising carrying out the method in presence of at least one nuclease and (a) at least one organic-based hydrophilic macromolecule having a molecular weight of 50 kDa to 500 kDa and neutral surface charge, or (b) at least one organic-based hydrophilic macromolecule having a radius range of 2 to 50 nm. The method may be carried out (a) at standard time and temperature conditions, or (b) at extended time and lower temperature conditions compared to the time and temperature in (a).

According to another aspect, there is provided a method of determining the optimum crowding conditions in a method for nucleic acid synthesis, and/or amplification and/or for improving the efficiency, activity and/or stability of at least one nucleic acid-modifying enzyme, the method comprising providing at least one macromolecule candidate, wherein the macromolecule is (a) at least one organic-based hydrophilic macromolecule of molecular weight 50 kDa to 500 kDa and neutral surface charge, or (b) at least one organic-based macromolecule of radius or radius range 2 to 50 nm and neutral surface charge, and determining the macromolecular concentration or macromolecular concentration range for the optimal volume exclusion effect with minimal viscosity changes of the macromolecule in solution.

The method determining of macromolecular concentration or macromolecular concentration range for optimum crowding may be based on estimation of hydrodynamic radius of the at least one macromolecule.

According to another aspect, there is provided a method of identifying a suitable macromolecule and/or macromolecular conditions for nucleic acid synthesis and/or amplification and/or for improving the efficiency, activity and/or stability of at least one nucleic acid modifying enzyme, the method comprising providing at least one macromolecule candidate, wherein the macromolecule is (a) at least one organic-based hydrophilic macromolecule of molecular weight 50 kDa to 500 kDa and neutral surface charge, or (b) at least one carbohydrate-based hydrophilic macromolecule of radius 2 to 50 nm, and determining the molecular weight and/or concentration of the macromolecule or mixture of macromolecules with improved of nucleic acid synthesis, and/or amplification and/or of efficiency, activity and/or stability of at least one nucleic acid-odifying enzyme compared to a control macromolecule or mixture of macromolecules of predetermined molecular weight, radius and/or concentration.

BRIEF DESCRIPTION OF THE FIGURES

FIG. 5. Amplification curves for aP2 gene from real-time PCR under crowded conditions due to Ficoll 400 kDa (Fc400, 2.5 mg/ml) is 30.6 which is lower than $C_T$ for the uncrowded condition (control) that is about 32.9.

FIG. 8. Dissociation curves from real-time PCR using primers against aP2 under crowded conditions due to Fc400. Dissociation curves from real-time PCR using primers against aP2 under crowded conditions due to Ficoll 400 kDa (2.5 mg/ml) show a single peak, also higher than control. Primer concentrations used 250 nM; Specificity confirmed by observing the melting temperature for aP2 (~87.5° C.). Note the double-peak for PCR in uncrowded condition.

FIG. 18. Macromolecules increased primer specificity. Agarose gel (2%) of RT-PCR samples amplified with the collagen I set 2 PCR in the absence or presence of the macromolecule mixture Fc70/Fc400 (15 and 5 mg/ml, respectively) with increasing concentrations (conc.) of primers. The specific target was the band indicated at 228 bp. The cDNA was prepared from 250 ng total RNA. The −ve Cnt (control) was the PCR template-free control. The molecular weight marker (MW STD) was the 50 bp DNA Ladder.

DETAILED DESCRIPTION OF THE INVENTION

Figure 1:
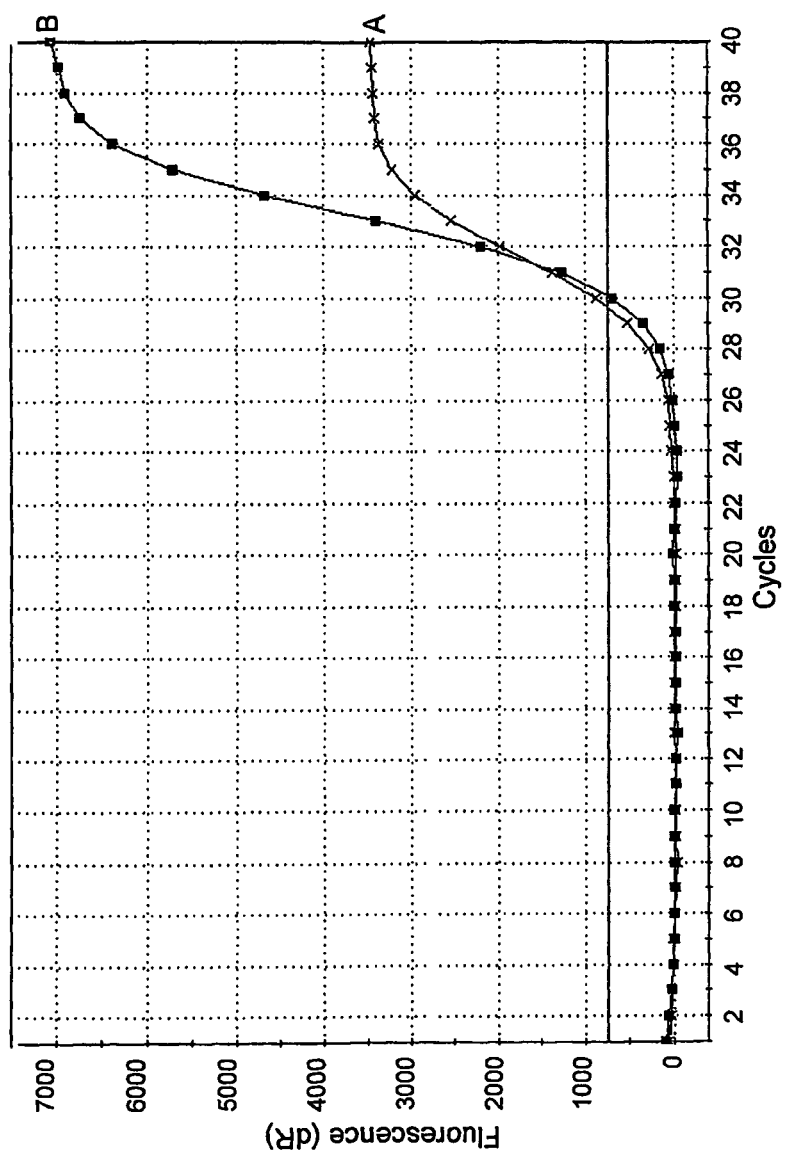
FIG. 1. Illustration of how efficiency increases few cycles post-$C_T$ under crowded conditions (B) in comparison to a routine (uncrowded) PCR (A).

Bibliographic references mentioned in the present specification are for convenience listed in the form of a list of references and added at the end of the examples. The whole content of such bibliographic references is herein incorporated by reference.

The current invention applies the principle of macromolecular crowding on an enzyme-catalyzed nucleic acid (for example DNA) synthesis and/or amplification in a cell-free environment. In particular, there is provided at least one method of nucleic acid synthesis and/or amplification, comprising carrying out the method in the presence of at least one organic-based hydrophilic macromolecule of neutral surface charge. In particular, the macromolecule according the invention may be (a) at least one organic-based hydrophilic macromolecule of molecular weight of 50 kDa to 500 kDa and neutral surface charge; and/or (b) at least one organic-based hydrophilic macromolecule having a radius of 2 to 50 nm, in particular, 5 to 20 nm, and neutral surface charge. There is also provided a method of improving the efficiency, activity and/or stability of at least one enzyme comprising using at least one enzyme in the presence of at least one organic-based hydrophilic macromolecule of neutral surface charge. In particular, there is provided a method of improving the efficiency, activity and/or stability of at least one enzyme comprising using at least one enzyme in the presence of (a) at least one organic-based hydrophilic macromolecule having a molecular weight of 50 kDa to 500 kDa and neutral surface charge, or (b) at least one organic-based hydrophilic macromolebule having a radius range of 2 to 50 nm and neutral surface change. The enzyme may be at least one nucleic acid-modifying enzyme, for example, a polymerase and/or a nuclease.

Enzyme(s)

Any enzyme suitable for the purpose of the present invention may be used. As mentioned the enzyme according to any aspect of the invention may be at least one nucleic acid-modifying enzyme, for example, but not limited to, a polymerase and/or a nuclease. For example, the polymerase may be any polymerase, like a reverse transcriptase. The nuclease may be an endonuclease or esonuclease. Accordingly, the enzyme may be a restriction enzyme. More specifically, any one of the following list of enzymes may be used for the purposes of the present invention. Any skilled person will know how to select any suitable enzyme to be used in any aspect of the present invention.

List of DNA and/or RNA Polymerizing and Modifying Enzymes

Thermophilic DNA Polymerases:

The thermophilic DNA polymerases, like other DNA polymerases, catalyze template-directed synthesis of DNA from nucleotide triphosphates requiring a primer having a free 3' hydroxyl to initiate synthesis and magnesium ion is necessary. There ability to sustain DNA polymerase activity at high biological temperatures enables their use in reactions requiring thermal cycling. This includes the following most commonly used polymerases and their various genetically engineered or isolated derivatives.

Taq DNA Polymerase: [From *Thermus aquaticus*] Half-life at 95 C. is 1.6 hours.

Pfu DNA Polymerase: [From *Pyrococcus furiosus*] Appears to have the lowest error rate of known thermophilic DNA polymerases.

Vent DNA Polymerase: also known as Tli DNA polymerase [From *Thermococcus litoralis*]. Half-life at 95 C. is approximately 7 hours.

One of the most discussed characteristics of thermostable polymerases is their error rate. Error rates are measured using several different assays, and as a result, estimates of error rate vary, particularly when the assays are performed by different labs. As would be expected from first principles, polymerases lacking 3'→5' exonuclease activity generally have higher error rates than the polymerases with exonuclease activity. The total error rate of Taq polymerase has been variously reported between $1 \times 10^{-4}$ to $2 \times 10^{-5}$ errors per base pair. Pfu polymerase appears to have the lowest error rate at roughly $1.5 \times 10^{-6}$ error per base pair, and Vent is probably intermediate between Taq and Pfu. Error rate is not the only consideration in choosing a polymerase for PCR, otherwise Taq polymerase would not continue to be the most widely used enzyme by far for the myriad of PCR applications. Other considerations, including reliability and what might be called "fussiness" enter into the choice.

Eukaryotic polymerases. Any known eukaryotic polymerase is encompassed.

Mesophilic DNA polymerases:

DNA polymerase 1 (DNA polymerase I): (from *E. coli*) implicated in DNA repair; has both 5'→3'(Nick translation) and 3'→5' (Proofreading) exonuclease activity.

DNA polymerase II: involved in replication of damaged DNA; has both 5'→3' chain extension ability and 3'→5' exonuclease activity.

DNA polymerase III: the main polymerase in bacteria (elongates in DNA replication); has 3'→5' exonuclease proof-reading ability.

DNA polymerase IV: a Y-family DNA polymerase.

DNA polymerase V: a Y-family DNA polymerase; participates in bypassing DNA damage.

Klenow fragment: (from *E. coli* DNA polymerase 1)
with or without exonuclease activity
some of the applications: synthesis of double-stranded DNA from single-stranded templates; filling in recessed 3' ends of DNA fragments; digesting away protruding 3' overhangs; preparation of radioactive DNA probes; DNA sequencing by the Sanger method T4 DNA polymerase: (from bacteriophage of *E. coli*)
very similar to the Klenow fragment
it functions as a 5'→3' DNA polymerase and a 3'→5' exonuclease
used for the same types of reactions as Klenow fragment, particularly in blunting the ends of DNA with 5' or 3' overhangs T7 DNA polymerase: (from bacteriophage of *E. coli*)
has high processivity
some applications: DNA sequencing by the chain termination technique
T7 DNA polymerase can be chemically-treated or genetically engineered to abolish it's 3'→5' exonuclease activity. These forms of the enzyme are marketed under the name Sequenase and Sequenase 2.0, and are widely used for DNA sequencing reactions.

Terminal deoxynucleotidyl transferase: (a mammalian enzyme, expressed in lymphocytes)
function: catalyzes the addition of nucleotides to the 3' terminus of DNA; it works on single-stranded DNA, including 3' overhangs of double-stranded DNA.
common application: used in adding homopolymers of ribonucleotides to the 3' end of DNA; labeling of the 3° ends of DNA with radioisotope-labeled nucleotides phi29 DNA Polymerase:
a highly processive polymerase featuring strong strand displacement activity which allows for highly efficient isothermal DNA amplification. The phi29 DNA Polymerase also possesses a 3'=>5' exonuclease (proofreading) activity acting preferentially on single-stranded DNA
Source: *E. coli* cells with a cloned gene 2 of *Bacillus subtilis* phage phi29 Applications: rolling circle amplification (RCA); multiple displacement amplification (MDA); unbiased amplification of whole genome; DNA template preparation for sequencing; protein-primed DNA amplification Bacteriophage DNA-dependent RNA polymerases
Phage-encoded DNA-dependent RNA polymerases are used for in vitro transcription to generate defined RNAs. Most commonly, the reaction utilizes ribonucleotides that are labeled with radionucleotides or some other tag, and the resulting labeled RNA is used as a probe for hybridization. Other applications of in vitro transcription including making RNAs for in vitro translation or to study RNA structure and function Commercially available bacteriophage RNA polymerases:
T7 RNA polymerase (from *E. coli*)
T3 RNA polymerase (from *E. coli*)
SP6 RNA polymerase (from *Salmonella typhimurium*)

Reverse Transcriptases
Reverse transcriptase is a common name for an enzyme that functions as a RNA-dependent DNA polymerase. They are encoded by retroviruses, where they copy the viral RNA genome into DNA prior to its integration into host cells.
Commercially significant types of RTs:
Moloney murine leukemia virus: a single polypeptide
Avian myeloblastosis virus: composed of two peptide chains Reverse transcriptases have two activities:
DNA polymerase activity: In the retroviral life cycle, reverse transcriptase copies only RNA, but, as used in the laboratory, it will transcribe both single-stranded RNA and single-stranded DNA templates with essentially equivalent efficiency. In both cases, an RNA or DNA primer is required to initiate synthesis.
RNase H activity: RNase H is a ribonuclease that degrades the RNA from RNA-DNA hybrids, such as are formed during reverse transcription of an RNA template. This enzyme functions as both an endonuclease and exonuclease in hydrolyzing its target.
Uses: Reverse transcriptase is used to copy RNA into DNA, to generate DNA copies of RNAs prior to amplifying that DNA by polymerase chain reaction (PCR).

Nucleic Acid Modifying Enzymes and their Applications (Non-Polymerases)
Exonuclease I: (from *E. coli*)
digestion of ssDNA or oligonucleotides
T4 Polynucleotide kinase (PNKase): (from T4 bacteriophage)
catalyzes the transfer of a phosphate from ATP to the 5' end of either DNA or RNA.
commercial preparations are usually products of the cloned phage gene expressed in *E. coli*.

The enzymatic activity of PNK is utilized in two types of reactions:
In the "forward reaction", PNK transfers the gamma phosphate from ATP to the 5' end of a polynucleotide (DNA or RNA). The target nucleotide is lacking a 5' phosphate either because it has been dephorphorylated or has been synthesized chemically.
In the "exchange reaction", target DNA or RNA that has a 5' phosphate is incubated with an excess of ADP—in this setting, PNK will first transfer the phosphate from the nucleic acid onto an ADP, forming ATP and leaving a dephosphorylated target. PNK will then perform a forward reaction and transfer a phosphate from ATP onto the target nucleic acid.

There are two major indications for phosphorylating nucleic acids and hence use of PNK are:
Phosphorylating linkers and adaptors, or fragments of DNA as a prelude to ligation, which requires a 5' phosphate. This includes products of polymerase chain reaction, which are typically generated using non-phosphorylated primers.
Radiolabeling oligonucleotides, usually with $^{32}$P, for use as hybridization probes.

T4 DNA Ligase: (from bacteriophage)
Ligation of blunt or cohesive ends of DNA

Alkaline phosphatase:
removes 5' phosphate groups from DNA and RNA. It will also remove phosphates from nucleotides and proteins. These enzymes are most active at alkaline pH—hence the name.
Sources: Bacterial alkaline phosphatase (BAP) is the most active of the enzymes, but also the most difficult to destroy at the end of the dephosphorylation reaction; Calf intestinal alkaline phosphatase (CIP) is purified from bovine intestine. This is phosphatase most widely used in molecular biology labs because, although less active than BAP, it can be effectively destroyed by protease digestion or heat (75 C. for 10 minutes in the presence of 5 mM EDTA); Shrimp alkaline phosphatase is derived from a cold-water shrimp and is promoted for being readily destroyed by heat (65 C. for 15 minutes).
Primary uses: Removing 5' phosphates from plasmid and bacteriophage vectors that have been cut with a restriction enzyme. In subsequent ligation reactions, this treatment prevents self-ligation of the vector and thereby greatly facilitates ligation of other DNA fragments into the vector (e.g. subcloning); Removing 5' phosphates from fragments of DNA prior to labeling with radioactive phosphate. Polynucleotide kinase is much more effective in phosphorylating DNA if the 5' phosphate has previously been removed.

Restriction endonucleases: enzymes that cleave the sugar-phosphate backbone of DNA.
  3 classes: I, II and III
  class II is the most common and commercially important one Nucleases:
  cleave or digest nucleic acids into smaller fragments Deoxyribonuclease I: (from bovine pancreas)
  cleaves double-stranded or single stranded DNA, endonuclease
  some common applications: eliminating DNA (e.g. plasmid) from preparations of RNA; analyzing DNA-protein interactions via DNase footprinting; nicking DNA prior to radiolabeling by nick translation.

Ribonuclease A: (from bovine pancreas)
  is an endoribonuclease that cleaves single-stranded RNA at the 3' end of pyrimidine residues.
  some common applications: eliminating or reducing RNA contamination in preparations of plasmid DNA; mapping mutations in DNA or RNA by mismatch cleavage (RNase will cleave the RNA in RNA:DNA hybrids at sites of single base mismatches, and the cleavage products can be analyzed)

Exonuclease III: (*E. coli*)
  Removes mononucleotides from the 3' termini of duplex DNA. The preferred substrates are DNAs with blunt or 5' protruding ends. It will also extend nicks in duplex DNA to create single-stranded gaps
  Used most commonly to prepare a set of nested deletions of the termini of linear DNA fragments Endonuclease IV:
  The Endonuclease IV recognizes apurinic/apyrimidinic (AP) sites of dsDNA and cleaves the phosphodiester bond 5' to the lesion generating a hydroxyl group at the 3'-terminus. The enzyme can also act as a 3'-diesterase that is able to release 3'-phosphoglycolate or 3'-phosphate from the damaged ends of dsDNA
  Applications: studies of DNA damage and repair; single cell electrophoresis (Comet assay); antitumor drug research; DNA structure research.

Endonuclease V: (from *T. maritima*)
  a 3'-endonuclease, which initiates removal of deaminated bases from damaged DNA, including uracil, hypoxanthine and xanthine. Endonuclease V is also active toward abasic and urea sites, base pair mismatches, flap and pseudo Y structures, and small insertions/deletions in DNA molecules. The cleavage site generated by Endonuclease V occurs at the second phosphodiester bond in the 3' direction from the lesion. When an excess of the enzyme is present, the primary nicked products experience a second nicking event on the complementary strand, leading to a double-stranded break. At low concentrations, Endonuclease V first nicks a DNA strand at the lesions located closer to the 5'-end of the DNA molecule. Single-stranded DNA is cleaved with much lower efficiency than double-stranded DNA. $Mg^{2+}$ or $Mn^{2+}$ ions are required for enzyme activity
  Applications: High-throughput methods for mutation research; Studies in mutagenesis and DNA repair; Mismatch cleavage; Genotyping.

Lambda Exonuclease:
  is a highly processive 5'=>3' exodeoxyribonuclease. It selectively digests the phosphorylated strand of double-stranded DNA. The enzyme exhibits greatly reduced activity on single-stranded DNA and non-phosphorylated DNA, and has no activity at nicks and limited activity at gaps in DNA
  some applications: generating single-stranded PCR products for use in: DNA sequencing and analysis of DNA single-strand conformation polymorphism (SSCP); Producing single-stranded DNA from double-stranded DNA fragments.

Mung Bean Nuclease: (Mung bean sprouts)
  Digests single-stranded DNA to 5'-phosphorylated mono or oligonucleotides. High concentrations of enzyme will also degrade double-stranded nucleic acids.
  Used to remove single-stranded extensions from DNA to produce blunt ends.

Nuclease BAL 31: (*Alteromonas*)
  Functions as an exonuclease to digest both 5' and 3' ends of double-stranded DNA. It also acts as a single-stranded endonuclease that cleaves DNA at nicks, gaps and single stranded regions. Does not cleave internally in duplex DNA.
  Used for shortening fragments of DNA at both ends.

Nuclease S1: (*Aspergillus*)
  The substrate depends on the amount of enzyme used. Low concentrations of S1 nuclease digests single-stranded DNAs or RNAs, while double-stranded nucleic acids (DNA:DNA, DNA:RNA and RNA:RNA) are degraded by large concentrations of enzyme. Moderate concentrations can be used to digest double-stranded DNA at nicks or small gaps.
  Used commonly to analyze the structure of DNA:RNA hybrids (S1 nuclease mapping), and to remove single-stranded extensions from DNA to produce blunt ends.

Ribonuclease T1: (*Aspergillus*)
  An endonuclease that cleaves RNA at 3' phosphates of guanine residues, producing oligonucleotides terminal guanosine 3' phosphates.
  Used to remove unannealed regions of RNA from DNA:RNA hybrids.

Ribonuclease H: (*E. coli*)
  The Ribonuclease H(RNase H) specifically degrades only the RNA strand in RNA-DNA hybrids. It does not hydrolyze the phosphodiester bonds within single-stranded and double-stranded DNA and RNA.
  Applications: Removal of mRNA prior to the synthesis of the second strand of cDNA; Removal of the poly(A) sequences of mRNA after hybridization with oligo(dT); Site-specific cleavage of RNA; Studies of in vitro polyadenylation reaction products Ribonuclease I: (RNase I)
  an endoribonuclease, preferentially hydrolyzes single-stranded RNA to nucleoside 3'-monophosphates via nucleoside 2'-,3'-cyclic monophosphate intermediates
  Applications: Removal of RNA from DNA solutions; Removal of RNA from recombinant protein preparations; Ribonuclease protection assays With reference to the macromolecule according to any aspect of the invention, the macromolecule is at least one organic-based hydrophilic macromolecule of neutral surface charge. The macromolecule may have a molecular weight of 50 kDa to 500 kDa. In particular, the macromolecule may have a molecular weight of 70 kDa to 450 kDa. More in particular, the macromolecule may be a mixture of at least two macromolecule with different molecular weight, like Ficoll 70, Ficoll 400, PVP 360, neutral dextran 410 and/or neutral dextran 670. More in particular, the macromolecule(s) may be a mixture of Ficoll 70 and Ficoll 400. Further, the macromolecule may have a radius range of 2 to 50 nm, in particular, 5 to 20 nm. The macromolecule may be a carbohydrate-based hydrophilic macromolecule. For example, the macromolecule may be a polymer, in particular, a polymer of glucose and/or sucrose.

The invention will now be described in more detail with reference to nucleic acid amplification, and in particular to polymerase chain reaction (PCR) application. In particular, a PCR and a host of other DNA and/or RNA synthesis/amplification methodologies are provided to demonstrate that the construct can enhance the nucleic acid synthesis and/or amplification. However, the invention is not limited to the application of PCR and any other amplification method known in the art or still to be developed may be used. Further, the invention also comprises the application of the macromolecule according to the invention in nucleic acid(s) synthesis. The invention also encompasses the uses of the macromolecule according to the invention for improving the efficiency, activity and/or stability of at least one enzyme. Accordingly, any tool, reagent, conditions and/or reference to "amplification" or "PCR" should be considered to apply, in general, also to the nucleic acid synthesis or the method of improving the efficiency, activity and/or stability according to the invention.

The present inventors have targeted a spectrum of parameters that may be influenced to extend the applicability of the said techniques for research, diagnostic and/or therapeutic purposes. These parameters include but not restricted to (i) sensitivity, specificity and efficiency of PCR when it is the pertinent DNA amplification procedure, (ii) productivity, processivity and fidelity of the DNA polymerizing enzyme (iii) the yield of the product due to amplification which may be DNA or RNA as the case may be. Specificity: ability to synthesize and/or amplify the exact length of the target sequence indicated by the melting temperature. Sensitivity: ability to produce detectable amplification from low concentrations of target. Processivity: number of nucleotides polymerised/unit time before enzyme detaches from target. Efficiency: rate of amplification per unit cycle indicated by the slope of the amplification curve. Fidelity: enzyme's ability to add correct complementary base expressed as error/nucleotides added. Productivity: ability to use a fraction of routinely used concentration of enzyme for detectable amplification.

The present inventors provide high-molecular weight macromolecules, of 50 kDa to 500 kDa, which have not till date been tried for DNA synthesis and/or amplification procedures such as but not limited to PCR, at such concentrations that do not affect the solution viscosity, pH, ionic strength or reporter dye fluorescence, where applicable, of a typical DNA synthesis and/or amplification procedure.

For estimating the required macromolecule concentrations, the inventors employed biophysical tools such as dynamic light scattering and viscosimetry that helped in determining the size and shape characteristics of the macromolecules in addition to finding out the concentrations at which crowding actually set-in in a purely biophysical environment and tested the applicability of the obtained values on DNA and/or RNA synthesis and/or amplification.

Increased Specificity. The inventors have applied macromolecular crowding to obtain a greater yield of specific-length PCR products as determined by their dissociation profiles in a real-time PCR. The specificity of amplification depends on the extent to which the primers can recognize and bind to sequences other than the intended target DNA sequences. Although conditions are usually chosen to ensure that only strongly matched primer-target duplexes are stable, spurious amplification products can nevertheless be observed. This can happen if one or both chosen primer sequences contain part of a repetitive DNA sequence, and so primers have been designed to avoid matching to known repetitive DNA sequences, including large runs of a single nucleotide GGG or CCC). Accidental matching at the 3' end of the primer is critically important: spurious products may derive from substantially mismatched primer-target duplexes unless the 3' end of the primer shows perfect matching.

Increased Sensitivity. The inventors have tested the ability of a PCR to produce detectable amplification from low concentrations of template which defines the degree of sensitivity of the PCR. In a real-time setting, this amplification is measured by the incorporation of a fluorescent dye SYBR Green that can bind to double-stranded DNA. The concept of the threshold cycle (Ct) allows for accurate and reproducible quantification using fluorescence based RT-PCR. Fluorescence values are recorded during every cycle and represent the amount of product amplified to that point in the amplification reaction. The more templates present at the beginning of the reaction, the fewer number of cycles it takes to reach a point in which the fluorescent signal is first recorded as statistically significant above background, which is the definition of the (Ct) values. By increasing the apparent concentrations of the reactant molecules by macromolecular crowding, we aim to show that it improves the sensitivity of a PCR by lowering the $C_T$ of an amplification run in a real-time setting.

Increase Productivity. The inventors have investigated the increased productivity of polymerase (for example, Taq polymerase) and the yield of synthesis and/or amplification (for example, PCR) product(s). By crowding the PCR environment, the inventors showed a "polymerase sparing effect"; in the sense that detectable amplification were obtained even with significantly less amount of enzyme in the reaction mix. Under crowded conditions, it is shown that the activity of the Taq polymerase is increased at higher number of cycles and if this results ultimately in a greater population of DNA copies. The structural integrity of the enzyme can be a limiting factor at the later PCR cycles due to repeated thermal cycling. However, since macromolecular crowding can stabilize the native structure of a protein (Cheung et al. 2005), we expected that the principle can maintain the thermostability of the enzyme even at the late cycles and hence prolong the exponential amplification which might be required if the copy number of initial target templates is low.

This amplification (example, PCR) procedures according to the invention have shown several results:
(i) It demonstrates the effect of crowding in producing detectable amplification at reduced enzyme amounts; makes PCR more economical, hence more suited for up-scaling of PCR and mass production.
(ii) It does not compromise on specificity or sensitivity of the original PCR. In fact, it improves the specificity and spares the redundant excess of polymerase that is routinely used.
(iii) By crowding a PCR, the amount of product generated is enhanced and this represents a useful tool to maximize the efficiency and increase the number of PCR cycles and still generate an exponential amplification which otherwise would hit a saturation.

Efficiency of PCR amplification: The inventors have also shown that macromolecular crowding enhances the rate at which the copy numbers increase with each PCR cycle (FIG. 1). This rate depends on the slope of the amplification curve and is an index of the efficiency of the PCR amplification. Efficiency in a PCR is a measure of the rate of amplification per cycle. It is thus suggestive of the 'speed' of amplification. During the early exponential phase of the PCR it is close to 1, which is equal to 100% in terms of percentage. The $C_T$ is measured at this early phase. Hence it is plausible to compare the sensitivities of two different amplification curves based on the $C_T$. But the efficiency drastically reduces at the late exponential phase and decreases to zero at saturation plateau. These effects are not reflected if amplification profile is judged based only on the $C_T$. Therefore, efficiency of PCR particularly at the post-threshold phase of the PCR is equally important to know the complete amplification profile. This is exemplified by a simple example. Two amplification runs, A and B (see illustration below in FIG. 1) may have the same $C_T$ but 'A' may hit a plateau a few cycles after the $C_T$, whilst 'B' may continue with exponential amplification for many cycles more than the other before it hits a plateau. It is easy to evaluate that B is definitely more efficient than A and yields a greater amount of product finally.

Increased Fidelity. The inventors have studied whether crowding could reduce the error rate of the polymerase for nucleotide incorporation by favoring the binding of the correct complementary base-pairs which are thermodynamically more stable than mis-matched base-pairs. Cell-based DNA cloning involves DNA replication in vivo, which is associated with a very high fidelity of copying because of proofreading mechanisms. However, when DNA is replicated in vitro the copying error rate is relatively higher. Of the heat-stable DNA polymerases required for PCR, the most widely used is Taq DNA polymerase derived from *T. aquaticus*. This DNA polymerase, however, has no associated 3'→5' exonuclease to confer a proofreading function, and the error rate due to base mis-incorporation during DNA replication is rather high. This means that, even if the PCR reaction involves amplification of a single DNA sequence, the final product will be a mixture of extremely similar, but not identical DNA sequences.

Despite the errors due to replication in vitro, DNA sequencing of the total PCR product may give the correct sequence. This is because, although individual DNA strands in the PCR product often contain incorrect bases, the incorporation of incorrect bases is essentially random. As a result, for each base position, the contribution of one incorrect base on one or more strands is overwhelmed by the contributions from the huge majority of strands which will have the correct sequence. Accordingly, further analysis of the product may be difficult. If the PCR product is to be cloned in cells (e.g. to facilitate DNA sequencing or to permit functional studies in a cell-based expression system), transformation selects for a single molecule, and the cell clones chosen to be amplified will contain identical molecules, each the same as a single starting molecule which may well have the incorrect DNA sequence because of a copying error during PCR amplification.

Increased Processivity: The synthesis of complementary DNA strands depends on how long the enzyme is able to bind to DNA over time while copying it. Thus, highly processive polymerases may synthesize a long stretch of DNA before they detach from the target. This ability is crucial if the target is considerably long (several kb). The processivity depends on the following factors:
(i) Nature of the enzyme: replicative polymerases such as the T4 DNA polymerase have an inherent high processivity (several kb/minute). These are continuously involved in DNA replication in the nucleus/nucleoid of a cell. But non-replicative polymerases such as the Taq polymerase are generally called upon to repair any gaps in the DNA and are as such not critical for constitutive (routine) DNA synthesis in vivo. In other words, they are inherently of a lower processivity. This presents a potential problem for in vitro DNA synthesis in reactions such as the PCR that employ these low processivity enzymes, particularly if the target is long (one to several kb). (ii) The conditions of the polymerization reaction: PCR depends on multiple rounds of thermal cycling. Hence the polymerase can suffer structural damage after a number of repetitive thermal cycles. This can adversely affect the processivity that already is relatively low due to the inherent non-replicative property of DNA polymerase that is being used.

By enhancing the binding strength of polymerase to DNA, crowding can act as a processivity factor so that the polymerase does not fall-off from its target while synthesizing long complementary strands of DNA. In addition, the structural integrity of the enzyme is not perturbed much and thus helps in maintaining the stability of the target-primer-polymerase complex.

Applications of the embodiments according to the present invention. The following applications are given only as example and accordingly any embodiment of the invention should not be considered to be limited to the application given. Further applications in the art evident to a skilled person are also encompassed by the application of the present invention.

1. Single-Tube PCR

The application of the principle of macromolecular crowding on a one-step PCR can be greatly helpful in automating the PCR. A reverse transcription system is combined with a PCR amplification system such that at temperatures conducive for reverse transcription, the PCR amplification is prevented and when the PCR amplification takes over after the RT has been synthesized, the reverse transcriptase-system gets inactivated at the high temperatures of the PCR. This is essentially the principle of the one-step PCR. Incorporating a single macromolecule or combinations of different macromolecules according to the invention, for example at biophysically predetermined concentrations, enables enhancement of both reverse transcription and PCR amplification in the same tube without having to add them sequentially. This application represents an approach to simplify current PCR technologies and to lead to methods to automate PCR with an intention of using as less an amount of the target and PCR components with maximum sensitivity and specificity which could be applied to short or long base-pair amplifications, and be able to obtain large amounts of amplification products.

2. Miniature PCR Based on Micro-Fluidics Technology (MEMS)

Recent PCR silicon chips fabricated using MEMS techniques have shown great potential for DNA amplification. Their low thermal inertia enables a more rapid DNA sample amplification process with reduced sample and reagent consumption. Micro-chip devices based PCR for rapid diagnosis of bacterial infection and antibiotic resistance genes are known in the art. Incorporation of a macromolecular crowder in a microchip PCR system can greatly enhance the ability of the system in terms of sensitivity and specificity for diagnostic purposes. The low viscosity of the macromolecular crowders at the concentrations that are sufficient for effecting volume exclusion can be a useful property.

3. Applications in Forensic Medicine, Archaeology and Anthropology

The ability to use low amounts of RNA for reverse transcription in the presence of crowding so that the cDNA transcripts are in high copies is beneficial to applications in the field of forensic medicine where, more often than not, the availability of a sufficient amount of material for RNA extraction is the key to solving many medico-legal/criminological issues. The same application can also be used in field of archeology and/or medical anthropology for detection and/or identification of genetic linkages for population studies, or the like.

4. Commercial Kits

Development of reaction buffers with pre-included macromolecular crowding agents for different molecular biology applications such as PCR, reverse transcription, restriction enzymatic digestion, or the like. These buffers may be provided as prepacked, premixed solutions and are easily integrated in preexisting molecular biology kits.

Comparison of the present invention in view of existing strategies. The comparison and/or discussion here as follows is only given as example with reference to some existing strategies and it is not intended to be limiting.

(i) Strategies adopted to optimize reaction specificity:
  (a) Nested primers. By using nested primers, the products of an initial amplification reaction are diluted and used as the target DNA source for a second reaction in which a different set of primers is used, corresponding to sequences located close, but internal, to those used in the first reaction. The present invention addresses this problem by crowding the PCR reaction buffer to promote the specific binding of the target DNA, primer and polymerase to form a stable ternary complex at the start of the PCR run. Hence when compared to the nested PCR, the method of the present invention does not require two or more sets of primers and hence is much simpler. This also reduces the number of steps that might be required and hence reduces the time consumed for each run.
  (b) Hot-start PCR. Mixing of all PCR reagents prior to an initial heat denaturation step allows more opportunity for nonspecific binding of primer sequences. To reduce this possibility, one or more components of the PCR are physically separated until the first denaturation step. A popular approach is to use a specially formulated wax bead designed to fit snugly into a PCR reaction tube. The reaction components minus the enzyme and reaction buffer are added to the tube followed by the molten wax bead which floats on top and then solidifies on cooling. The thermostable polymerase is then added with buffer. At the initial denaturation step the wax melts again and rises to the surface causing all the reaction components to come into contact with each other. Another approach is to use a polymerase that is chemically-conjugated to an antibody that prevents any activity of the enzyme until when it has been heated to the denaturation temperature (eg. AmpliTaq gold from Applied Biosystems). Although Hot-start PCR is a fail-safe mechanism for ensuring non-specific binding, the present invention permits the use of a less complex enzyme that still can yield products without compromising on specificity.
  (c) Touch-down PCR. Most thermal cyclers can be programmed to perform runs in which the annealing temperature is lowered incrementally during the PCR cycling from an initial value above the expected $T_m$ to a value below the $T_m$. By keeping the stringency of hybridization initially very high, the formation of spurious products is discouraged, allowing the expected sequence to predominate. Using the macromolecular crowder according to the present invention, there is no need to re-program the cycler and the PCR may still proceed under the same temperature settings as before. Thus the reproducibility is not affected.
  (d) Enhancement of PCR by low molecular weight osmolytes. Osmolytes, such as betaine (trimethylglycine), are naturally occurring small molecular weight compound which may help in saline tolerance of several bacteria. The mechanisms of action of these small molecules is rather not very clear. It is described that they function by thermostabilizing the proteins and destabilizing DNA helix. However, the report (Spiess et al, 2002) notes that these effects are evident only for difficult templates that have extensive secondary structures. Hence the effect is to simplify and linearise the secondary DNA structure (for example due to a high GC content). This lowers the $T_m$ of the template and indirectly favours polymerization at a lower temperature.

The effect of the osmolytes is to denature the target by breaking down secondary structures. This may not be the exact physiological condition for ensuring high fidelity base-pair matching for complementary strand synthesis. Therefore, the advantages of such compounds are not applicable for situations where the improvement of the PCR amplification profile is sought for reasons other than the difficult template characteristics. Such other examples are when there is a low concentration of the target, reduced enzyme amounts available or higher number of cycles required, or even when a larger amount of product is desired. It is pointed out that it has not been shown that these osmolytes offer any advantage in increasing the productivity and yield of the Taq polymerase and fidelity of the enzyme. Perhaps fidelity may even be compromised due to the non-physiological structural changes of DNA in the presence of high amounts of the osmolyte. The method according to the present invention applies the principle of Excluded Volume Effect (EVE) to reduce the amounts of enzyme needed for amplification. Since the crowded environment is a physiological condition for DNA synthesis, the structure of DNA is not interfered with and this helps the polymerase in adding the correct base-pairs at a high fidelity.

(ii) Processivity

Several attempts have been proposed to improve processivity of polymerase. Approaches taken towards this goal till date are:
  (a) generation of a chimerical protein containing a heterologous motif or domain for binding to a known processivity factor, such as thioredoxin (U.S. Pat. No. 5,972, 603) or PCNA (Motz, M., et al., 2002). Although improvement in processivity was observed when the chimeric protein and the corresponding processivity factor were used together, the application of this method to improve PCR has not been established. In a different approach, a replication complex composed of multiple polypeptides isolated from *T. thermophilus* was reassembled in vitro. Although processive DNA synthesis from single-stranded (ss)DNA template was observed, again, utility in PCR was not confirmed.
  (b) WO0192501 describes a constructed fusion protein of the polymerase with a sequence non-specific ds-DNA binding protein. This may be beneficial to polymerase operating at room temperature. However for PCR amplification, this construct again has to go through the temperature cycles of a PCR.

Although the peptide factors increased processivity, developing the art needs complex methods. The present invention is based on non-peptide strategies that are simpler than the reported techniques. It is also possible to combine the technology according to the invention with the peptide strategies for synergistic effects on processivity. Accordingly, the present invention provides a novel strategy to enhance the processivity of the polymerase by a generic and purely physical mechanism that does not alter the conditions of the PCR as such and can be used independently or in collaboration with prior strategies in this regard.

(iii) Efficiency of a PCR

As explained earlier, the efficiency of a standard PCR usually drops below 1 (100%) with the progression of PCR cycles. Exhaustion of primers and instability of Taq polymerase occur after repeated heat cycles. This lowers the processivity of the enzyme and amount of the PCR product per cycle. Hence there is efficiency drop at later cycles. The exponential phase of amplification is confined to only a few cycles after the $C_T$. Using high amounts of enzyme and primer concentrations, the efficiency of the PCR can be maintained for a longer time.

Macromolecular crowding speeds up enzyme kinetics by stabilizing the enzyme-substrate transition complex. Hence by a multitude of factors, such increased binding affinity, a more structurally and functionally stable enzyme, stronger hybridization, the exponential phase of amplification can be prolonged. This can yield a greater amount of product ultimately.

Accordingly, with the present invention it has been demonstrated that carbohydrate based macromolecules improve fidelity and yield of first strand cDNA that can in-turn result in a greatly increased second strand cDNA (ds-cDNA) after a PCR run.

According to particular embodiments, the invention relates to:

(i) a methodology to use high molecular weight macromolecules or combinations thereof as additives for molecular biology applications in vitro, separately or in combination, that improves molecular biological assays and protocols Wherein the macromolecule(s) is a carbohydrate-based macromolecule exhibiting a neutral surface charge and having a molecular weight of 50 kDa to 500 kDa, preferably polymers of glucose or sucrose.

Wherein the molecular biology applications in vitro include but are not limited to:

Complementary DNA (cDNA) synthesis or where appropriate, the first strand cDNA synthesis from total and/or messenger RNA extracted from biological materials.

The said biological material may be derived from sources of human, animal, plant origin, bacterial, fungal, and viral. Either freshly prepared, archival or ancient.

The methodology of the said synthesis of the cDNA from the extracted RNA is based on standard enzyme catalyzed nucleotide polymerization procedures by reverse transcriptases derived from such sources, but not limited to, the Moloney Murine Leukemia virus (M-MLV) and Avian Myeloblastosis virus (AMV).

Amplification of the synthesized cDNA or where appropriate, the first strand cDNA using DNA polymerization enzymes.

The said amplification techniques include, but not limited to, Polymerase Chain reaction (PCR) and modifications thereof such as nested PCR, hot-start PCR, inverse PCR, and other amplification procedures such as RACE (rapid amplification of cDNA ends), solid phase amplification (SPA) and so on.

The methodology of DNA amplification is based on techniques that employ DNA polymerase enzymes derived from thermophilic bacteria including but not limited to *Thermus aquaticus, Thermophilus, Pyrococcus furiosus* and mesophilic bacteria including but not limited to *E. coli* such as T4 DNA polymerase, T7 DNA polymerase The methodology of DNA amplification may be carried out at specific temperatures stated by the manufacturer which may include but not limited to, ambient temperature, physiological body temperature such as 37° C. and repeated thermal cycling at temperatures for DNA denaturation (e.g. 94° C. but not limited to this temperature), annealing of primer (e.g. in the range of but not limited to 45 to 75° C.) and polymer extension (e.g. 72° C. but not limited to depending on the type of DNA polymerase).

The methodology of DNA amplification may be monitored real-time or by determining the end-products of amplification by visualization of electrophoretically separated DNA bands on an agarose or a polyacrylamide gel.

The methodology of real-time monitoring of DNA amplification may be done using fluorescent technology such as fluorescent dyes that specifically bind to synthesized/amplified double stranded DNAs (e.g. SYBR Green 1 but limited to this dye) and fluorescently labeled primers which their accompanying technologies such as, but not limited to, TaqMan technology. The fluorescence detected may be quantified as a parameter that depends on the concentration of DNA synthesized/amplified The macromolecule according to the invention may gave a hydrodynamic radius range size of 3 nm to 50 nm, in particular, 7 nm to 20 nm, more in particular 10 nm to 20 nm, preferably of 14 nm. Ficoll 70(Fc70) has a radius of 4-6 nm and Ficoll 400(Fc400) has a radius of 12-14 nm according to our DLS results and these agree with literature data.

(ii) A biophysical methodology to determine the optimum crowding conditions: wherein The method is based on Laser light scattering principles to estimate the diffusion coefficients of macromolecules in solution and hence their hydrodynamic radii by simple mathematical deductions.

The estimates of said hydrodynamic radii are applied to determine the macromolecular concentration for the maximal or optimal volume exclusion effects with minimal viscosity changes of the said macromolecular solutions or combinations thereof at the determined concentrations limited to the specific biological reaction.

(iii). The method of synthesis of cDNA or first strand cDNA as appropriate, which involves addition of macromolecules or combinations of different macromolecular species thereof, into the reaction mixture or buffer at predetermined concentrations.

(iv). The method of identifying the ideal macromolecule or combinations thereof that is/are thermostable after repetitive temperature cycles.

(v). The range of the macromolecular concentrations for optimum crowding under conditions of pH and electrolyte concentrations for first strand cDNA synthesis, which is based on the estimation of hydrodynamic radii by dynamic light scattering.

(vi). The method of preparing the macromolecular solutions under physiologic conditions with viscosities of the said solutions confined to values less than 2 cP (2 mPa·s).

(vii). The effect of addition of the said macromolecules of the claimed molecular weight at the said concentrations into the reaction buffer of a reverse transcription reaction to enhance the yield or the amounts of the first strand cDNA thus synthesized under the said crowded conditions (viii). The method of combining more than one type of macromolecular species for the reverse transcription reaction in (vii).

(ix). The combination of different macromolecules at predetermined proportions improves the effect mentioned in (vii).

(x). The method of synthesis of second strand cDNA by PCR, which involves addition of macromolecules or combinations of different macromolecular species according to the invention, optionally into the reaction buffer at predetermined concentrations (xi). The range of optimum concentration of the macromolecular solution or combinations thereof, preferably under conditions of pH and electrolyte concentrations for second strand cDNA synthesis mentioned in (x) by measurement of the hydrodynamic radius (xii). The method of preparing the macromolecular solutions under physiologic conditions with viscosities of the so-prepared solutions confined to values lower than 2 cp (2 mPa·s), in particular in the vicinity or about 1 cP (2 mPa·s) (close to water).

(xiii). The effect of addition of the said macromolecules of the pertinent molecular weight, preferably at the said concentrations, into the reaction buffer of a reverse transcription reaction to enhance the yield or the amounts of the first strand cDNA thus synthesized under the estimated crowded conditions.

(xiv) The concentrations preferred range from 2.5-25 mg/ml for Ficoll 400.

(xv) The method of combining more than one type of macromolecular species for the reverse transcription reaction mentioned in (vii).

(xvi) The combination of different macromolecules at predetermined proportions improves the effect mentioned in (xiii). The determined combination is a mixture of, but not limited to, Ficoll 70 and Ficoll 400.

(xvii) The method of carrying out reverse transcription in crowding conditions in 2 phases may have better effect on the final yield of the first strand cDNA. The preferred art involves adding only Ficoll 70 at a concentration of 7.5-15 mg/ml for the annealing step of oligo(dT) to the RNA and a combination of Fc70(7.5 mg/ml) and Fc400(2.5 mg/ml) for subsequent polymerization step of first strand cDNA synthesis.

(xviii) The effect of addition of the said macromolecules or combinations thereof of the pertinent molecular weights at the said concentrations/mixed concentration proportions into the reaction buffer of a reverse transcription reaction is claimed to enhance the processivity of the reverse transcriptase globally, meaning, increased yield of cDNA strands, longer cDNA strands, better quality of synthesized cDNA due to increased enzyme fidelity.

(xix) The effect of addition of the said macromolecules or combinations thereof of the pertinent molecular weight at the concentrations/mixed concentration proportions into the reaction buffer of a reverse transcription reaction enhances the yield or the amounts of the first strand cDNA thus synthesized under the estimated crowded conditions (xx) The effect of addition of the said macromolecules or combinations thereof of the pertinent molecular weight at the concentrations/mixed concentration proportions into the reaction buffer of a polymerase chain reaction enhances the sensitivity of the PCR for target detection under the estimated crowded conditions.

(xxi) The effect of addition of the said macromolecules or combinations thereof of the pertinent molecular weight at the concentrations/mixed concentration proportions into the reaction buffer of a polymerase chain reaction enhances the yield of specific PCR product when incorporated into the reaction mix of a PCR.

(xxii). The effect of addition of the said macromolecules or combinations thereof of the pertinent molecular weight at the concentrations/mixed concentration proportions into the reaction buffer of a polymerase chain reaction allows for using a fractional amount of routine concentration of Taq polymerase for a detectable amplification.

(xxiii) The addition of the said macromolecules or combinations thereof of the pertinent molecular weight at the concentrations/mixed concentration proportions into the reaction buffer of a polymerase chain reaction maintains/improves the efficiency of the PCR even at higher number of cycles (xxiv) The effect of addition of the said macromolecules or combinations thereof of the pertinent molecular weight at the concentrations/mixed concentration proportions into the reaction buffer of a polymerase chain reaction reduces the error rate of the Taq polymerase and contributes to improved fidelity of the enzyme to incorporate the correct complementary base (xxv) The addition of the said macromolecules or combinations thereof of the pertinent molecular weight at the concentrations/mixed concentration proportions into the reaction buffer of a polymerase chain reaction functions as a (processivity factor to keep the enzyme-DNA complex intact for a longer time period, thus helping synthesis of long DNA strands in a PCR.

(xxvi) Macromolecular crowding of both reverse transcription and PCR in a single tube, by the "one-step" PCR method is claimed to result in a better amplification profile that enhances all aforementioned PCR parameters. The beneficial ramifications of the one-step PCR method is claimed to be suitable for automation of PCR thus bridging the biophysical principles of macromolecular crowding with the technological advancements in MEMS devices for a robust RT-PCR instrument.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Materials and Methods:

All RT and PCR components were purchased from Invitrogen (Singapore) unless stated otherwise. All reactions were conducted on the real-time Mx3000P (Stratagene, Calif., USA). The macromolecules were Fc70 (70 kDa) and Fc400 (400 kDa) (Amersham Pharmacia, Uppsala, Sweden). (Dextran 410 and Dextran 670 from Fluka, Sigma-Aldrich, USA. PVP from Sigma, USA). The small molecules were trehalose (Fluka-Sigma-Aldrich, Singapore), proline (Sigma-Aldrich). They were dissolved in nuclease-free water as a concentrate and added freshly to the reaction buffers each time.

Example 1

Figure 2:
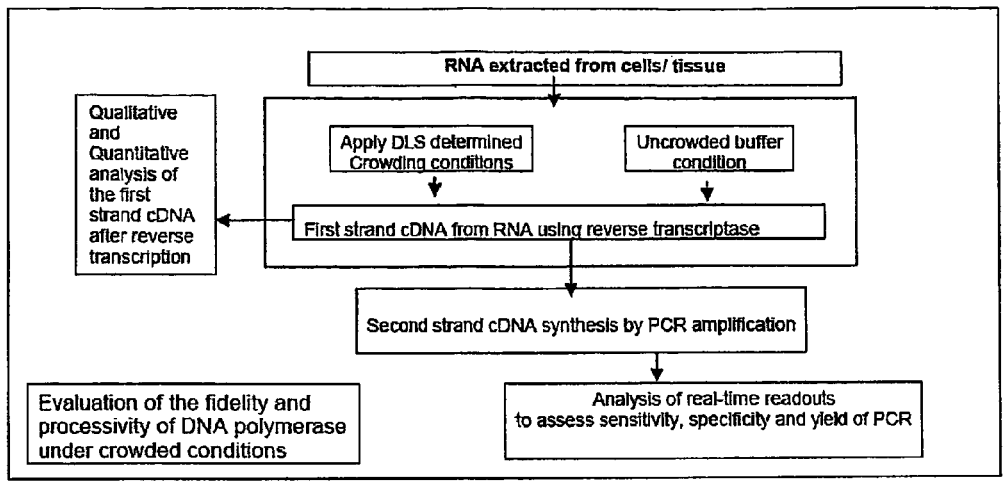
FIG. 2. Schematic flow chart to show the application of crowding to enhance reverse transcription of mRNA to cDNA FIG. 3. Schematic flow chart to show the application of crowding to enhance PCR FIG. 4. Amplification curves for aP2 from real-time PCR under crowded conditions (red or dark dot curve—dextran) due to neutral Dextran 410 KDa (125 µg/ml) is 30.4 lower than $C_T$ for the uncrowded condition (control) that is 31.6.

Effects of crowding the reverse transcription reaction buffer on the yield of first strand cDNA. FIG. 2 shows a schematic flow chart to show the application of crowding to enhance reverse transcription of mRNA to cDNA.

1. RNA extraction.

RNA was extracted from human Wi-38 fibroblasts; American Tissue Culture Collection, VA, USA (ATCC) and differentiated human adipocytes from human mesenchymal stem cells (Cambrex Bio Science, MD, USA) with the Adipogenic hMSC Differentiation BulletKit (Cambrex)] based on a modification (the modification is in using a monophasic solution of phenol and guanidium isothiocyanate) of the single step method of Chomczynski & Sacchi, 1987, Anal Biochem 162, 156. The method uses 2 ml of TRIzol, a monophasic solution of phenol and guanidine isothiocyanate.

Cells/tissue homogenate was dissolved in a precalculated volume (1 ml of TRIzol per 10 sq·cm dish) and 0.2 ml of chloroform per 1 ml of TRIzol to separate out the fatty components.

Then, the aqueous supernatant containing the nucleic acid material was treated with isopropanol (0.5 ml per ml of TRIzol) to isolate RNA from DNA and the extracted RNA was then precipitated with 1 ml of 75% ethanol per ml of TRIzol. All the steps were carried out in RNAse-free deionized, diethylpyrocarbonate (DEPC)-treated water (DEPC from Sigma) or with the RNAqueous (Ambion Inc., TX, USA) according to the Manufacturer's protocol.

The absorbance of RNA was measured at 260 nm, The quality of the extracted RNA was determined by the ratio of the absorbance at 260 nm/280 nm.

2. Dynamic Light Scattering (DLS) Profiling of Macromolecules for RT-PCR

Dynamic light scattering estimation of hydrodynamic radius and optimum concentration of macromolecular crowding agents;

DLS based thermostability screening of macromolecules for PCR applications.

DLS methods: DLS runs were carried out for each of the single macromolecular species (Fc70, Fc400, Neutral Dextran 410 and Neutral Dextran 670, PVP 360) solutions using the Dynapro DLS instrument. DLS was carried out at 20° C. by loading 20 µl samples of each macromolecular solution. The readings were obtained at a wavelength of 8258 and analyzed using the Protein Solutions™ software provided with the Dynapro instrument.

3. Viscosity measurements:

Viscosity measurements at the corresponding macromolecular concentrations in Hanks buffered salt solution (Fc 70: 5 mg/ml to 25 mg/ml; Fc 400: 5 mg/ml to 50 mg/ml; ND 410 & 670: 100 µg/ml to 10 mg/ml; PVP 360: 100 µg/ml to 10 mg/ml) were estimated using the ARES100 FRT Rheometer. Based on the viscosity values, necessary corrections were applied for the hydrodynamic radii by plugging in the viscosity value in the Stokes-Einstein equation (that relates the diffusion coefficient of a particle in solution to the hydrodynamic radius of the particle and viscosity of the solution) to calculate the correct hydrodynamic, radius.

4. Thermostability Screening:

To screen macromolecules for thermostability, solutions of macromolecules were made in Hanks buffered salt solution at different concentrations (Fc 70: 5 mg/ml to 25 mg/ml; Fc 400: 5 mg/ml to 50 mg/mil; ND 410 & ND670: 100 µg/ml to 10 mg/ml; PVP 360: 100 µg/ml to 10 mg/ml) and 20 µl of each sample was subjected to 35 thermal cycles sequentially at 56° C.-72° C.-94° C. DLS runs before and after thermal cycling were done and data analysed in the Dynapro software.

5. First Strand cDNA Synthesis
Sample Preparation:

An initial reagent mix was prepared by mixing 1 µl each of Oligo(dT) primer and 10 mM dNTP (for 1× concentration) and made up to 12 µl with water. For crowding the test samples, the crowding macromolecule (Ficoll PM 400; MW. 400,000, Amersham Pharmacia) was dissolved in water to a final concentration of 2.5 mg/ml before mixing the Oligo(dT) and dNTP mix in the same proportion as mentioned above. For mixed macromolecular crowding, Ficoll 70 (MW. 70 kDa; Amersham Pharmacia) was added to the annealing buffer at a final concentration of 7.5 mg/ml. For the polymerization step (see below), final concentrations of Ficoll 70 (also indicated as Fc70) (7.5 mg/ml) and Ficoll 400 (also indicated as Fc400) (2.5 mg/ml) in combination were prepared in the reaction buffer.

2 µl of this mix was added to the volume of RNA suspension that was calculated to contain the required RNA amounts (eg. ~1 µg or 2 µg). The mix was heated at 65° C./5' and cooled on ice.

In the meantime reaction master mixes were prepared by adding the following (for 1×):
5× buffer 4 µl (5× First Strand Buffer, Invitrogen: 250 mM Tris-HCl, pH 8.3; 375 mM KCl; 15 mM $MgCl_2$)
0.1 M DTT 2 µl (1,4-Dithio-L-threitol, Invitrogen)
SSRT (200 U/µl) 1 µl (SuperScript Reverse Transcriptase I, Invitrogen)
RNAse inhibitor (40 U/µl) 1 µl
8 ul of this reaction mix was added to each of the initial reagent mix and heated at 42° C./50' and then 72° C./15'

The reverse transcript samples were taken out and stored at −20° C.

6. Second Strand cDNA Synthesis(Ds-cDNA Synthesis)
Procedure Primer Design:

Primers against the target gene sequences were designed using the Primer3™ software (MIT, USA). The primers were selected such that:

(i) The primer size was ~20 nt long each (forward and reverse; FP & RP.

(ii) Both FP and RP had $T_m$ of ~60° C.

(iii) The FP and RP were so chosen that their complementary sequences on the target sequence were flanking sequences on different exons so that any genomic DNA amplification during subsequent PCR is prevented.

(iv) Primers were designed against aP2 and a housekeeping gene GAPDH [aP2, tactgggccaggaatttgac (SEQ ID NO:1), gtggaagtgacgaatttcat (SEQ ID NO:2); GAPDH, gtccactgcgtcttcacca (SEQ ID NO:3), gtggcagtgatggcatggac (SEQ ID NO:4)]

(v) Aliquots of 2 µM were made from stock primer concentrations and stored at −20° C.

PCR mixes were prepared by adding the individual components as given in table below:

| Component | 1X (µl) |
| --- | --- |
| 10X buffer (see below) | 2.0 |
| $MgCl_2$ (25 mM) | 2.5 |
| dNTP (5 mM) | 1.0 |
| Primer (2 µM) | 2.0 |
| SYBR Green I (1:500) | 1.0 |
| Taq (5 U/µl) | 0.2 |
| Water | 9.3 |

*Taq polymerase, 10X PCR reaction buffer: 200 mM Tris-HCl; 500 mM KCl and $MgCl_2$ were obtained from Invitrogen™ (platinum Taq); SYBR Green I was from Molecular probes™

To 18 µl of the reaction mix, 2 µl of target DNA template was added and the real-time PCR was run as per the PCR program after necessary optimization for annealing temperature and [Mg++] concentration. Dissociation curves were obtained after taking the temperature to 60° C. followed by heating once to 94° C. and then cooling to 25° C.

These conditions were modified/optimized for different target sequences as required: (i) Optimizing the annealing temperature: annealing temperature for aP2 and GAPDH was optimized at 56° C., and for Collagen I set 1 and set 2 was optimized at 55° C. (ii) MgCl$_2$ concentration for the PCR optimized to 3 mM final concentration in the PCR reaction mix. After PCR run was completed, samples were taken out and stored at 4° C.

Example 2

Figure 3:
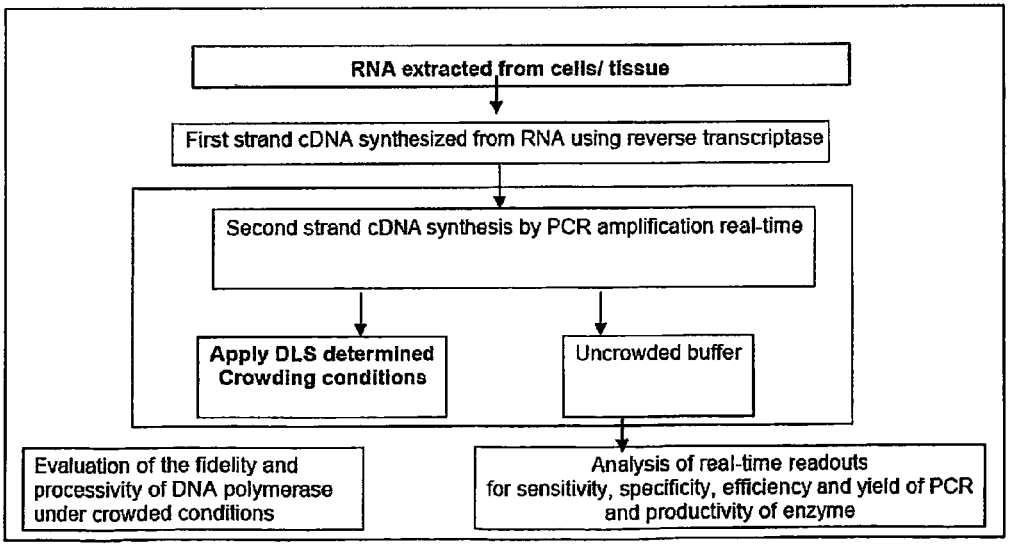

Effects of crowding the PCR reaction buffer on the yield of second strand cDNA. FIG. 3 shows a schematic flow chart to show the application of crowding to enhance PCR 1. RNA Extraction RNA is extracted from cells/tissue based on a modification of the single step method (Chomczynski & Sacchi, 1987, Anal Biochem 162, 156). The method uses TRIzol which is a monophasic solution of phenol and guanidine isothiocyanate as mentioned above.

Cells/tissue homogenate is dissolved in a precalculated volume of TRIzol and chloroform is added to separate out the fatty components.

Then, the non-fatty solution containing the nucleic acid material is treated with isopropanol to isolate RNA from DNA and the RNA is then precipitated with ethanol. All the steps are carried out in RNAse-free DEPC-treated water.

The absorbance of RNA is measured at 260 nm. The quality of the extracted RNA is determined by the ratio of the absorbance at 260 nm/280 nm.

2. Dynamic Light Scattering (DLS) Profiling of Macromolecules for RT-PCR

Dynamic light scattering estimation of hydrodynamic radius and optimum concentration of macromolecular crowding agents DLS based thermostability screening of macromolecules for PCR applications.

DLS methods: DLS runs were carried out for each of the single macromolecular species' solutions as mentioned above using the Dynapro DLS instrument. DLS was carried out at 20° C. by loading 20 µl samples. The readings were obtained at a wavelength of 8258 and analyzed using the Protein Solutions™ software provided with the Dynapro instrument.

3. Viscosity Measurements:

Viscosity measurements at the corresponding concentrations were estimated using the ARES100 FRT Rheometer. Based on the viscosity values, necessary corrections were applied for the hydrodynamic radii as mentioned above.

4. Thermostability Screening:

To screen macromolecules for thermostability, solutions of macromolecules were made in Hanks buffered salt solution at different concentrations as mentioned above and 20 µl of each sample was subjected to 35 thermal cycles sequentially at 56° C.-72° C.-94° C. DLS runs before and after thermal cycling were done and data analysed in the Dynapro software.

5. First Strand cDNA Synthesis

Sample Preparation:

An initial reagent mix was prepared by mixing 1 ul each of Oligo(dT) primer and 10 mM dNTP (for 1× concentration) and made up to 12 µl with water. 2 µl of this mix was added to the volume of RNA suspension that was calculated to contain the required RNA amounts (eg. ~1 µg or 2 µg). The mix was heated at 65° C./5' and cooled on ice.

In the meantime reaction master mixes were prepared by adding the following (for 1×):

| | |
|---|---|
| 5X buffer | 4 µl |
| 0.1M DTT | 2 µl |
| SSRT (200 U/µl) | 1 µl |
| RNAse inhibitor(40 U/µl) | 1 µl |

8 ul of this reaction mix was added to each of the initial reagent mix and heated at 42° C./50' and then 72° C./15' The reverse transcript samples were taken out and stored at −20° C.

6. Second strand cDNA synthesis (ds-cDNA synthesis)

Procedure

Primer design:

Primers against the target gene sequences were designed using the Primer3™ software. The primers were selected such that:

(i) The primer size was ~20 nt long each (forward and reverse; FP & RP)

(ii) Both FP and RP had T$_m$ of ~60° C.

(iii) The FP and RP were so chosen that their complementary sequences on the target sequence were flanking sequences on different exons so that any genomic DNA amplification during subsequent PCR is prevented.

(iv) Primers were designed against aP2 and a house-keeping gene GAPDH.

(v) Aliquots of 2 µM were made from stock primer concentrations and stored at −20° C.

PCR mixes were prepared by adding the individual components as given in table below:

| Component | 1X (µl) |
|---|---|
| 10X buffer | 2.0 |
| MgCl2 (25 mM) | 2.5 |
| dNTP (5 mM) | 1.0 |
| Primer (2 µM) | 2.0 |
| SYBR Green I (1:500) | 1.0 |
| Taq (5 U/µl) | 0.2 |
| Water | 9.3 |

*Taq polymerase, 10X buffer and MgCl2 were obtained from Invitrogen ™ (platinum Taq); SYBR Green I was from Molecular probes ™

The macromolecular crowder was dissolved in the master mix at the required concentration (Fc400: 2.5-5 mg/ml; Dextran 410 kDa: 125-250 ug/ml).

For the polymerization step (see below), final concentrations of Fc70(7.5 mg/ml) and Fc400(2.5 mg/ml) in combination were prepared in the reaction buffer.

To 18 µl of the reaction mix, 2 µl of target DNA template was added and the real-time PCR was run as per the PCR program after necessary optimization for annealing temperature and [Mg++] concentration. Dissociation curves were obtained after taking the temperature to 60° C. followed by heating once to 94° C. and then cooling to 25° C.

These conditions were modified/optimized for different target sequences as required.

After PCR run was completed, samples were taken out and stored at 4° C.

Results of Examples 1 and 2

(i) Sensitivity of the PCR amplification

Figure 4:
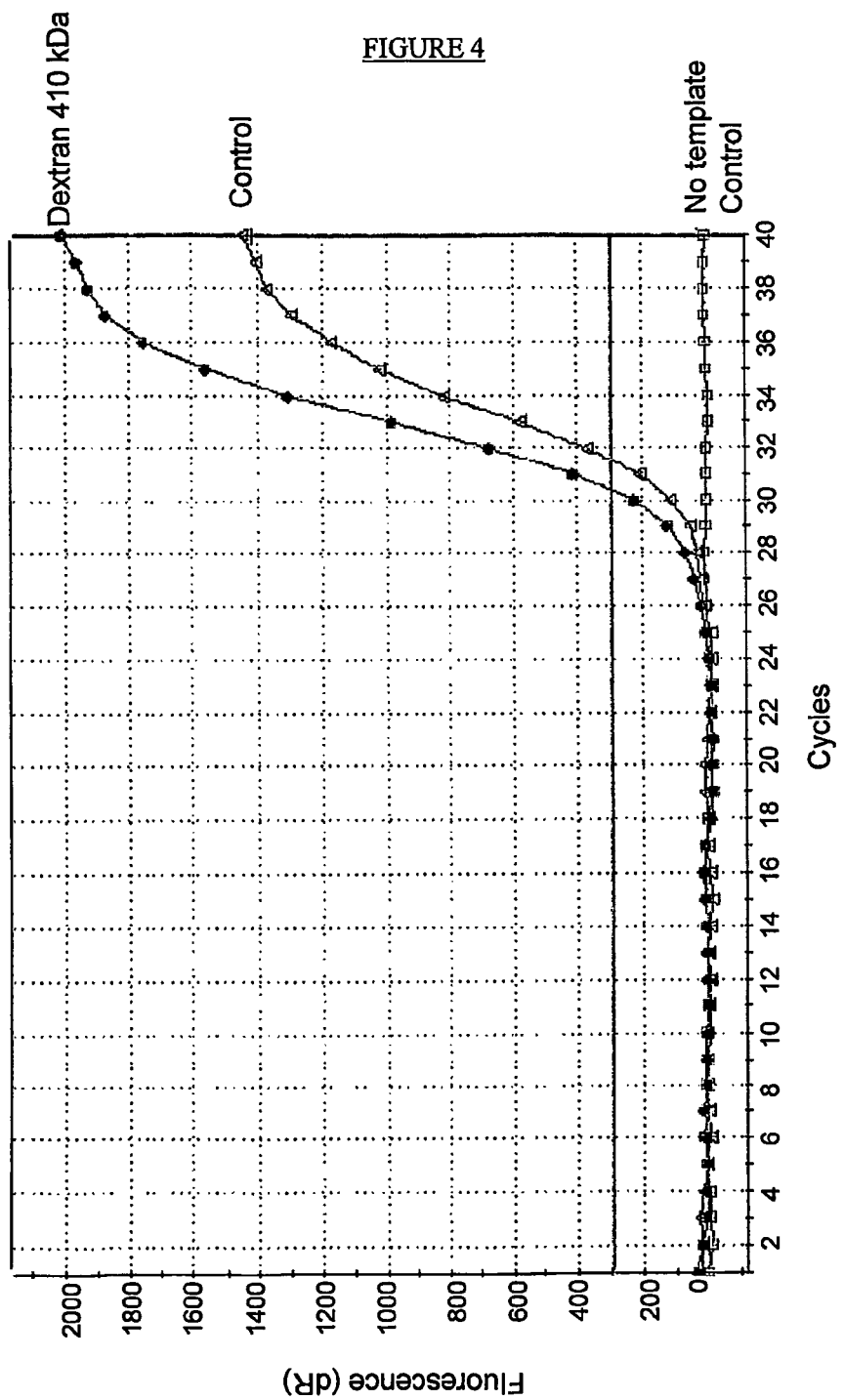

FIG. 4. shows a $C_T$ value for aP2 amplification under crowded condition (red or dark colour curve) due to Dextran 410 kDa (125 µg/ml) is 30.4 is lower than $C_T$ for the uncrowded condition (control) that is 31.6

Sensitivity of PCR amplification is determined by a minimum number of target DNA required to be present in the sample so that it can be detected after amplifying for a fixed number of cycles. In the real-time parlance, this is indicated by the cycle number in which there is a significantly elevated fluorescence above the baseline. This cycle number that marks the threshold amplification is denoted by the term $C_T$. Thus lower the value of $C_T$, more sensitive is the PCR. The Mx3000P software (Stratagene) computes the value of $C_T$ by fixing a threshold based on the degree of amplification and hence called as the "amplification-based threshold". All the $C_T$ values were obtained using the Mx3000P software for analysis.

In the present case, the reaction mixes with containing neutral dextran of 410 kDa, show a $C_T$ of ~30.4 (see FIG. 4) and the controls without crowding ~31.6(B), a cycle difference of −1.2 for threshold amplification. In the present case, it was assumed that the efficiencies of the PCR at the early exponential phases for the test and the control were the same as the values of the slopes of both amplification curves were calculated and found to be approximately equal in the early exponential phase.

Since a cycle difference ($\Delta\Delta C_T$) of 1 suggests a 2-fold difference of the initial target number (by the comparative quantitation method, Livak 1997), the results indicated an improved sensitivity due to PCR under crowded conditions due to neutral dextran 410 kDa. The above results proved that crowding by high molecular weight polymers does lead to increase in the sensitivity of amplification of PCR.

FIG. 5 shows the $C_T$ value for aP2 amplification under crowded condition (red or dark curve) due to Ficoll 400 kDa (2.5 mg/ml) that is 30.6 is lower than $C_T$ for the uncrowded condition (control) that is ~32.9.

The $C_T$ for the PCR amplification under crowded conditions due to Fc400 (see FIG. 4) at a concentration of 2.5 mg/ml was found to be 30.62 as compared to the control run in uncrowded conditions that was 32.93, a difference of ~2 cycles (by $\Delta\Delta C_T$ method).

Next, a comparison of the sensitivity due to a single macromolecular species with a combination of 2 different macromolecules was done by mixing Ficolls of different molecular weights to observe effects on PCR of a different gene target (GAPDH). Mixed macromolecular crowding has been biophysically shown to provide beneficial crowding effects compared to crowding by a single species alone (on the oxidative refolding of lysozyme, Zhou et al, 2004). The target was a house-keeping gene, GAPDH. The macromolecules selected were Ficoll 70 and Ficoll 400 in a combination of different proportions ranging from 2.5 mg/ml to 7.5 mg/ml for each. All permutations and combinations within this range were tried and PCR was run. As an example the amplification plots for a PCR using primers against GAPDH are shown below (FIG. 6A), the combination shown here is Fc70: Fc400:: 7.5:2.5. Melt curves confirmed the T corresponding to GAPDH (~90° C.).

Figure 6A:
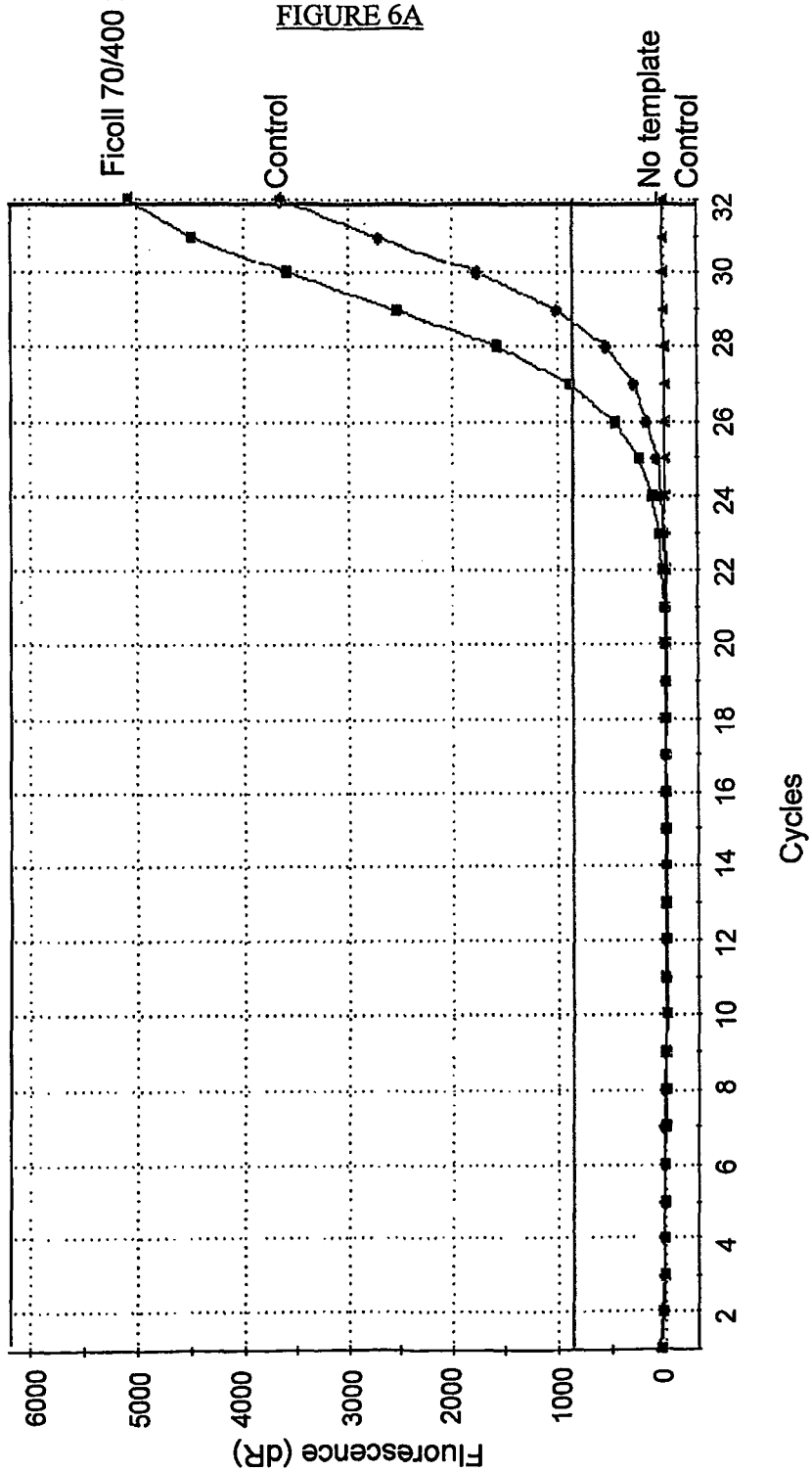
FIG. 6A. Amplification curves for GAPDH gene from real-time PCR under crowded conditions due to Ficoll 70+Fc 400. Improved sensitivity by mixed macromolecular crowding. The combination of Fc70 and Fc400 at a ratio ~(7.5):(2.5) lowers $C_T$ by ~2.0 cycles compared to the control.
Figure 6B:
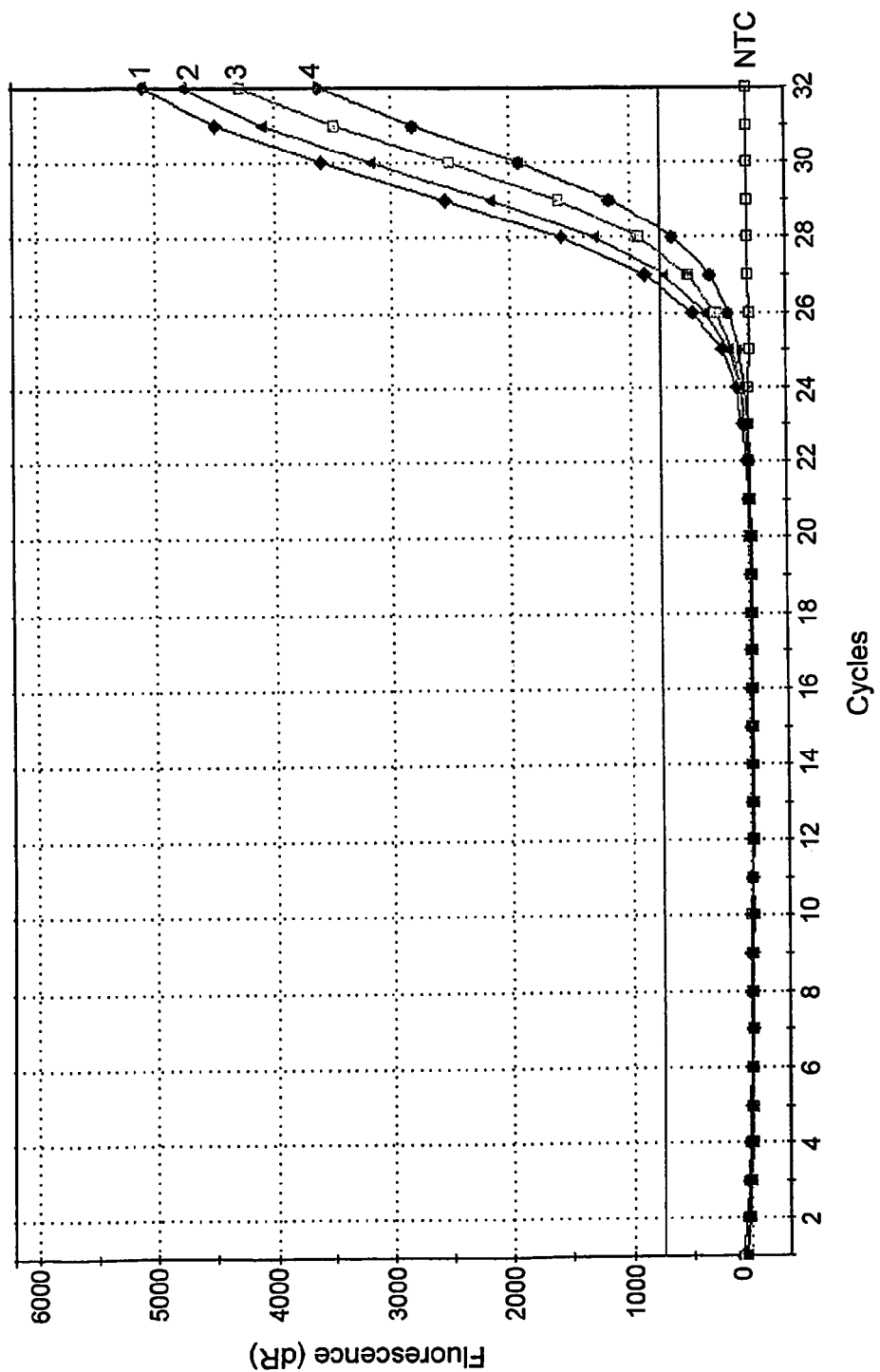
FIG. 6B. Improved sensitivity by mixed macromolecular crowding compared to crowding by single macromolecule. Improved sensitivity by mixed macromolecular crowding. The improvement in sensitivity due to the combination of graded increments of Fc70 and Fc400(1, 2, 3) is higher than the sensitivity due to Fc400 alone(4). 1: Fc70 (7.5 mg/ml)+Fc400(2.5 mg/ml); 2: Fc70 (5 mg/ml)+Fc400(2.5 mg/ml); 3: Fc70 (2.5 mg/ml)+Fc400(2.5 mg/ml); 4: Fc400(2.5 mg/ml); NTC: No template control FIG. 7. Dissociation curves from real-time PCR using primers against aP2 under crowded conditions due to Dextran. Dissociation curves from real-time PCR using primers against aP2 under crowded conditions due to Dextran 410 kDa (250 µg/ml) show a single peak, also higher than control. Primer concentrations used 100 nM; Specificity confirmed by observing the melting temperature for aP2 (~87.5° C.). Note the double-peak for PCR in uncrowded condition.

The sensitivity due to the mixed crowding was ~2.0 cycles lower $C_T$ compared to the control that was uncrowded (FIG. 6A). The sensitivity with mixed macromolecular crowding was better than the PCR run with Fc400 alone (2.5 mg/ml; FIG. 6B). The sensitivity shows a sequential improvement with graded increments of Ficoll 70 (2.5 mg/ml→45 mg/ml→7.5 mg/ml) in combination with a constant amount of Ficoll 400 (2.5 mg/ml). By mixed crowding, there is better binding between the primers and targets at the start of the amplification (due to Ficoll 70), and better stability of enzyme at later amplification cycles (Ficoll 400).

FIG. 6A shows an improved sensitivity by mixed macromolecular crowding. The combination of Fc70 and Fc400 at a ratio ~(7.5):(2.5) lowers $C_T$ by ~2.0 cycles compared to the control.

FIG. 6B shows an improved sensitivity by mixed macromolecular crowding. The improvement in sensitivity due to the combination of graded increments of Fc70 and Fc400(1, 2, 3) is higher than the sensitivity due to Fc400 alone(4). 1: Fc70 (7.5 mg/ml)+Fc400(2.5 mg/ml); 2: Fc70 (5 mg/ml)+Fc400(2.5 mg/ml); 3: Fc70 (2.5 mg/ml)+Fc400(2.5 mg/ml); 4: Fc400(2.5 mg/ml); NTC: No template control.

(ii) Specificity of the PCR Product

FIG. 7 shows dissociation curves from real-time PCR using primers against aP2 under crowded conditions due to Dextran 410 kDa (250 µg/ml) show a single peak, also higher than control. Primer concentrations used 100 nM; Specificity confirmed by observing the melting temperature for aP2 (~87.5° C.). Note the double-peak for PCR in uncrowded condition.

A specific PCR product has to match the calculated length of the target sequence and depends on primer design. This implies that it has to melt/dissociate at a temperature predicted from the primer GC content, sodium concentration etc. Hence by correlating the expected with the empirical values, we can identify the PCR specificity. The real-time PCR identified the specific product based on the melting temperature. A combination of the melt curve analysis and sequencing the PCR product reliably identified the right PCR product.

The specificity of the PCR amplification was verified by generating dissociation curves (melt curve see FIG. 6) for the PCR products. PCR was run at uncrowded (control) as well as crowded conditions (Dextran 410 kDa, 250 µg/ml) in the reaction buffer at a primer concentration of 100 nM (routine concentrations used: 200 nM). As can be seen from FIG. 8 the melt peaks correspond to a temperature of 87.5° C. that agreed with the $T_m$ for aP2. The melt curve showed a single sharp peak for the PCR run under crowded conditions. Under uncrowded conditions, a double-peak was noted. This was due to a non-specific product as a result of mis-priming. Crowding rectifies any non-specificity that may arise due to such reasons by enabling the primers to bind to the correct complementary sequences on the target. Another PCR run to test the effect of crowding by Ficoll 400 kDa on the specificity of PCR using a higher than routine primer concentration at 250 nM also showed that (FIG. 7) the crowding conditions maintain the specificity of the PCR in the face of changed PCR conditions that might otherwise lead to non-specific PCR products (see double-peak in FIG. 9).

FIG. 8 shows dissociation curves from real-time PCR using primers against aP2 under crowded conditions due to Ficoll 400 kDa (2.5 mg/ml) show a single peak, also higher than control. Primer concentrations used 250 nM; Specificity confirmed by observing the melting temperature for aP2 (~87.5° C.). Note the double-peak for PCR in uncrowded condition.

(iii) Efficiency of the PCR Amplification Due to Crowding

Liu and Saint, 2002 have established a new mathematical method for calculating the efficiency of a PCR amplification at any point during the cycle. Earlier methods have relied on relative quantitation which is based on constructing a standard curve for known amounts of a DNA sample and calculating the unknown quantity by normalizing to the known standards. The other method (the comparative $C_T$ method, Livak 1997) is based on the assumptions that the amplification efficiencies of the test and control are approximately equal and that the amplification efficiency is close to 1. Then the difference in the $C_T$ between the test and control ($\Delta\Delta C_T$) is computed and comparison is made. But this method is disadvantageous because it estimates the efficiency at the early exponential phase of the PCR and does not consider cycles in the late exponential phase which are equally important. It is a known fact that efficiency does fall at late exponential phase and much lower in the linear phase. To solve this problem, Liu and Saint provide a new method that can estimate the efficiency of a PCR from the kinetics of the reaction and then can be used for quantitation and normalization. The accuracy of this method is comparable to the standard curve method and better than the comparative $C_T$ method and has been applied in the present analysis of estimating PCR efficiency.

Figure 9:
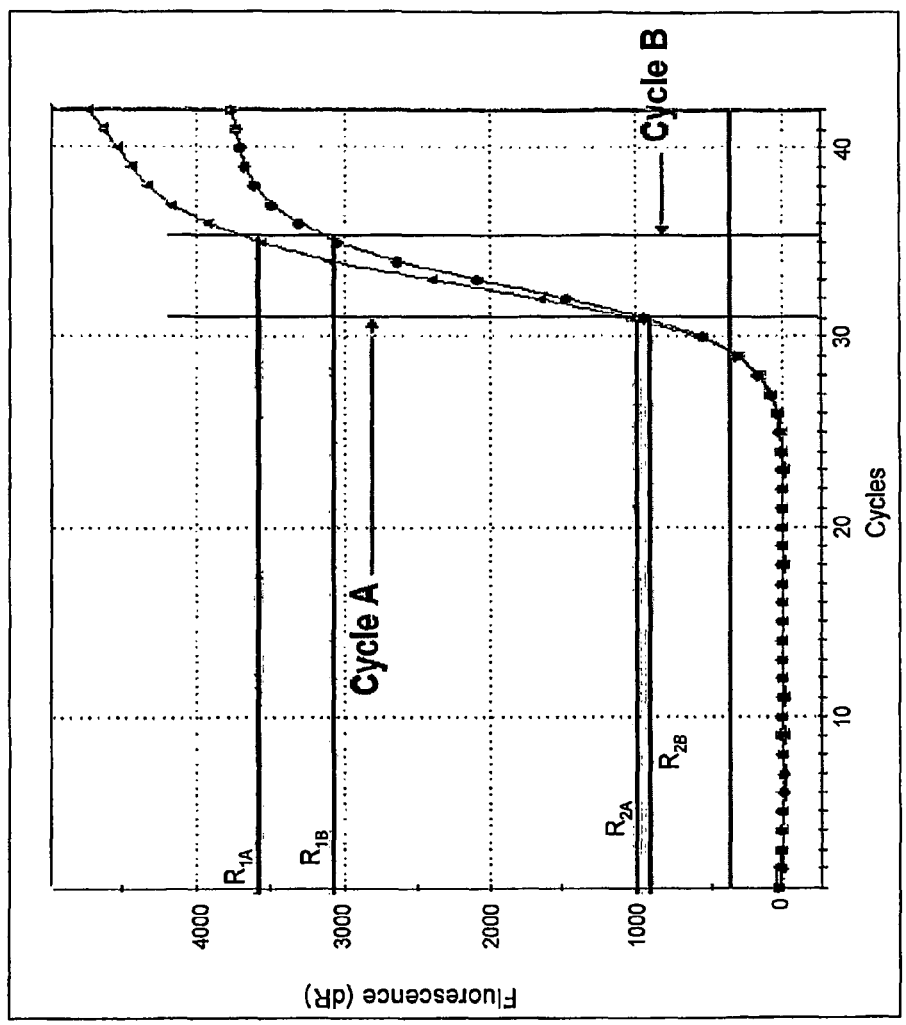
FIG. 9. Schematic illustration of determining the efficiency of a PCR at the late exponential phase of a PCR.

FIG. 9 shows a schematic illustration of determining the efficiency of a PCR at the late exponential phase of a PCR amplification.

According to the method of Liu and Saint, the fluorescence values of test and control samples at cycles A and B were noted from real-time PCR readouts. Then the efficiencies for both samples were calculated according to the formula (derived from Liu and Saint, 2002):

$$\frac{R'_{n,A}}{R_{n,B}} = (1+E)^{A-B}$$

Where,
$R_{n,A}$=fluorescence value at cycle number A
$R_{n,B}$=fluorescence value at cycle number B (for the same amplification curve)
E=Efficiency of PCR The efficiencies of the PCR amplification for different crowding agents were calculated according to the method and formula of Liu and Saint for PCR runs against aP2 (see melt curves below) and tabulated as follows:

Efficiency of PCR Amplification at the Late Exponential Phase

| Macromolecule | Test | Control | % gain |
| --- | --- | --- | --- |
| Ficoll 400 | 51% | 46% | 5% |
| Dextran 670 | 48% | 43% | 5% |
| PVP 360 | 36% | 21% | 15% |

It is to be expected that efficiency generally decreases at late PCR cycles. Thus the exponential amplification that is theoretically predicted (efficiency close to 100%) is no longer seen. However, under crowded conditions this fall in efficiency is corrected so that exponential amplification can occur for a longer time span. Thus, this indicates that crowding improves the overall efficiency of a PCR. We have observed that different macromolecules have different abilities in influencing the various parameters that have been discussed above. So, while one macromolecule improves sensitivity of PCR (Dextran 410,000), the effects on specificity may not be that great as compared to another macromolecule which has favorable effects on improving specificity or reducing the amounts of Taq enzyme for producing a good yield of PCR product (Ficoll 400,00)

A higher efficiency leads to a greater amount of PCR product that is finally produced. This is computed by integrating the dissociation curve to calculate the area under the curve as shown below:

(iv) Yield of PCR Product Computed from the Area Under the Dissociation Curve

Figure 10:
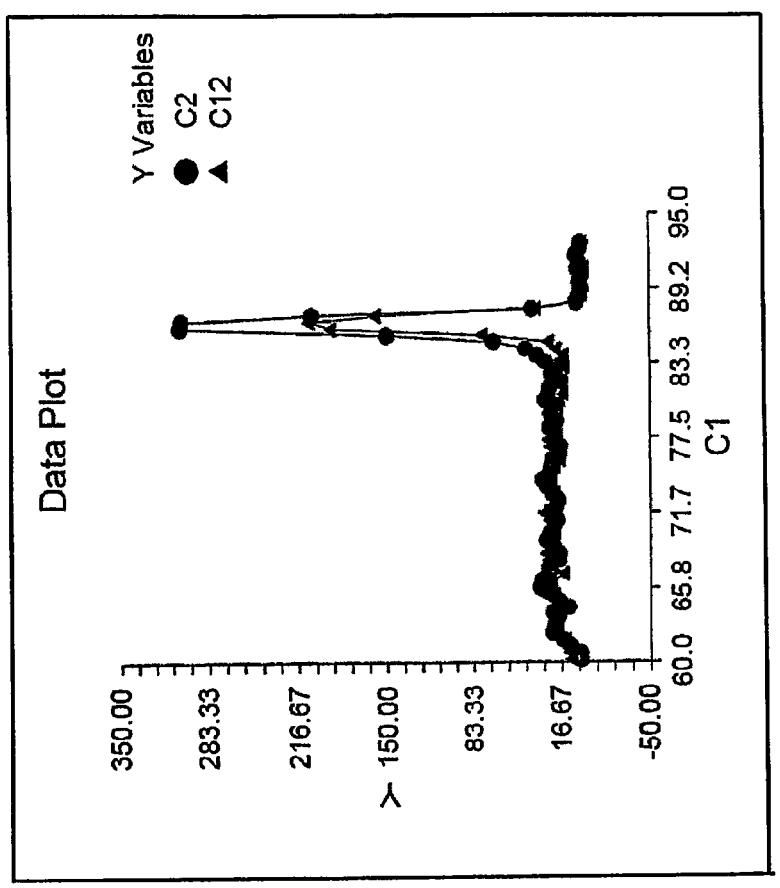
FIG. 10. Calculation of the area under the curve for PCR with Neutral Dextran 410 kDa (125 µg/ml) gives a value of 1116 sq. units as compared to the control 853 sq. units. *calculation done using NCSS™ software.

FIG. 10 shows calculation of the area under the curve for PCR with Neutral Dextran 410 kDa (125 µg/ml) gives a value of 1116 sq. units as compared to the control 853 sq. units. *calculation done using NCSS™ software Area under the dissociation curve is a measure of the number of copies of DNA that have been produced as a result of the PCR amplification. It is a distribution of the amplified products. Hence a single sharp, narrow peak is suggestive of a specific and pure product. The area under the peak which is an integrand of the fluorescence derivative and unit temperature ($\Delta T$) was computed by feeding the data into NCSS™ software.

Figure 11:
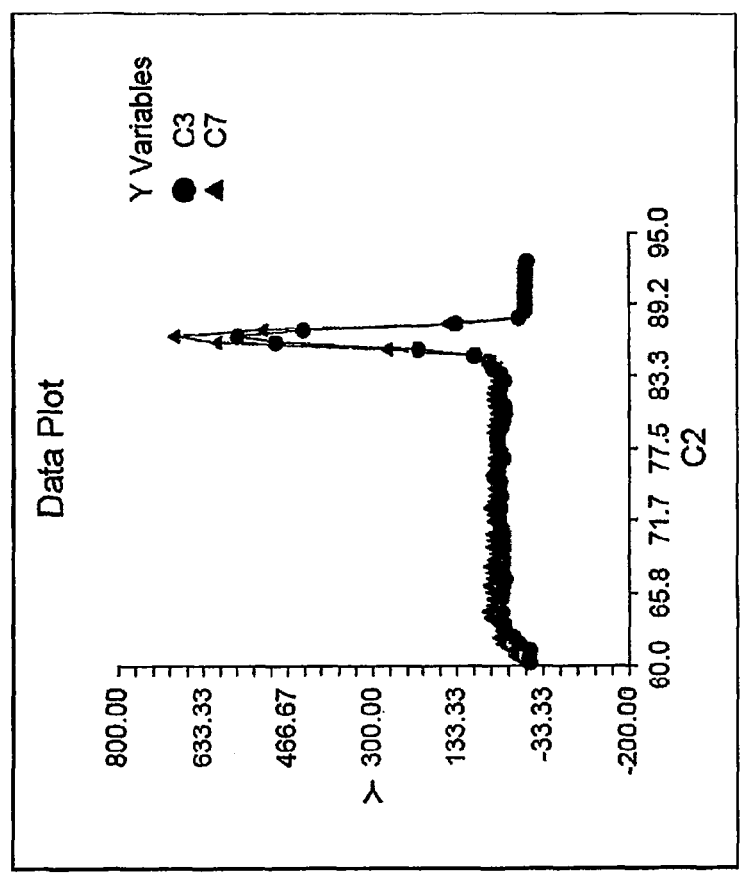
FIG. 11. Calculation of the area under the curve for PCR with Ficoll 400 kDa (2.5 mg/ml) gives a value of 2576 sq. units as compared to the control 2087 sq. units. *calculation done using NCSS™ software.

FIG. 11 shows calculation of the area under the curve for PCR with Ficoll PM 400 kDa (2.5 mg/ml) gives a value of 2576 sq. units as compared to the control 2087 sq. units. *calculation done using NCSS™ software. As shown in FIG. 11, the area under the melt curves for neutral dextran 410 and its corresponding control are respectively 1116 and 853 sq. units. This implies an increase of 31% in the total yield due to the macromolecular crowding with respect to the control.

Figure 12:
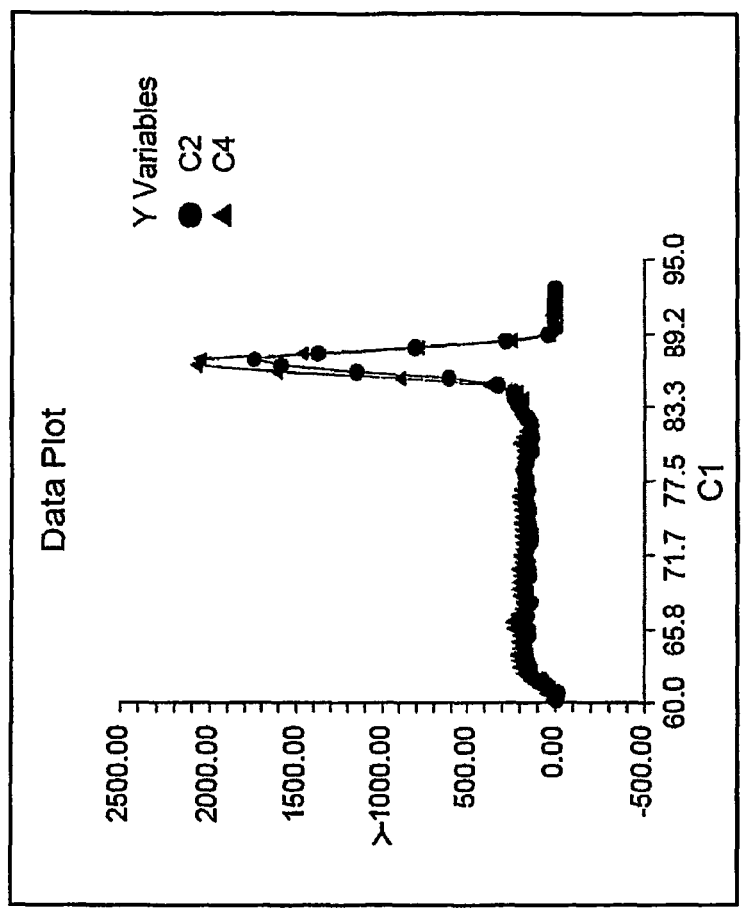
FIG. 12. Calculation of the area under the curve for PCR with Polyvinyl Pyrrolidone (PVP) 360 kDa (125 µg/ml) gives a value of 8478 sq. units as compared to the control 7022 sq. units.*calculation done using NCSS™ software.

FIG. 12 shows the calculation of the area under the curve for PCR with Polyvinyl Pyrrolidone 360 kDa (125 µg/ml) gives a value of 8478 sq. units as compared to the control 7022 sq. units. *calculation done using NCSS™ software. As shown in FIG. 12, the area under the melt curves for Ficoll 400 and its corresponding control are respectively 2576 and 2087 sq. units. This implies an increase of 23% in the total yield due to the macromolecular crowding with respect to the control.

Figure 13B:
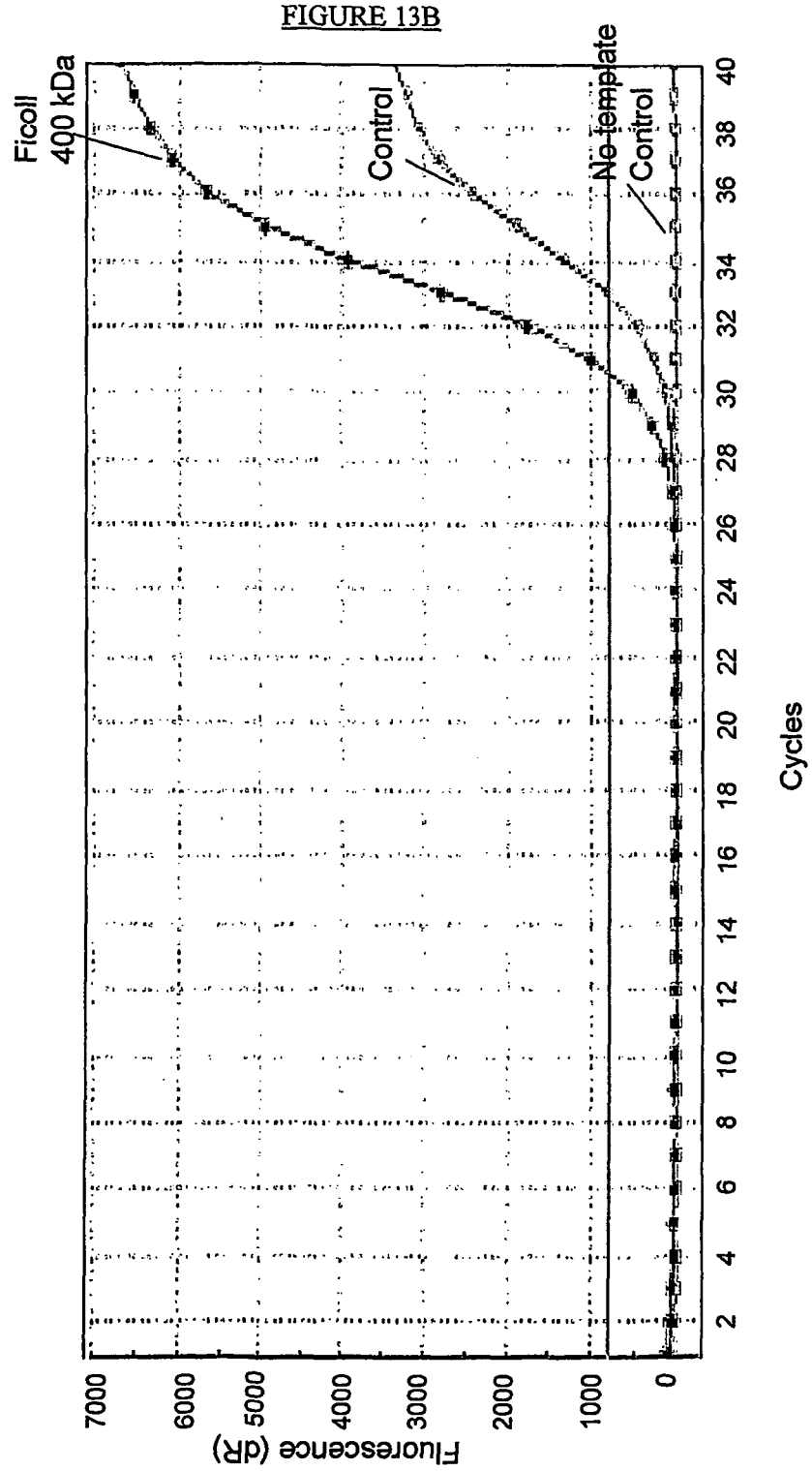
FIGS. 13A and B. Amplification and dissociation curves from real-time PCR of GAPDH, at routine and reduced concentration of Taq enzyme, in crowded conditions.

FIGS. 13A,B. Amplification and dissociation profiles of PCR runs using primers against aP2 gene at Taq concentrations of 1 U/reaction under crowded conditions due to Fc400. As shown in FIG. 13, the area under the melt curves for Polyvinyl Pyrrolidone 360 and its corresponding control are respectively 8478 and 7022 sq. units. This implies an increase of 21% in the total yield due to the macromolecular crowding with respect to the control Next, we proceeded to check whether crowding is able to yield a detectable amplification of the specific PCR product when the Taq polymerase enzyme was present at less than the routinely used concentrations (which is 1.25 U/reaction mixture). Accordingly, the appropriate dilutions of the enzyme were made and the PCRs were run at uncrowded and crowded conditions (due to Ficoll 400 kDa, 2.5 mg/ml) this concentration of Ficoll was selected considering our previous results with aP2 amplification, whence the macromolecule resulted in a better amplification profile in terms of specificity and yield.

A series of dilutions of Taq polymerase were made from a stock of 1.25 U/reaction as follows: 1 U/rxn, 0.75 U/rxn, 0.5/rxn, 0.25 U/rxn. Amplification of GAPDH gene at both uncrowded and crowded conditions was carried out at each dilution of the enzyme. The amplification profile at 1 U/reaction is shown in FIG. 13A. The profile indicates better sensitivity and efficiency for the crowding supported amplification. When the dissociation curves are observed, melt peaks correspond to ~87.5° C. (FIG. 13 B). The amount of the product as indicated by the area under the curve (AUC) is also higher for the crowded condition. A table showing the amount of the PCR product produced at higher enzyme dilutions (as mentioned earlier) is shown below. The amounts (AUC) at various dilutions are relative to the AUC of the 1 U/reaction aliquot.

| Enz. amt | condition | Normalized AUC |
|---|---|---|
| 1U/rxn | ---MMC | 0.42 |
| | +MMC | 1.00 |
| 0.75U/rxn | ---MMC | 0.40 |
| | +MMC | 0.71 |
| 0.5U/rxn | ---MMC | 0.31 |
| | +MMC | 0.63 |
| 0.25U/rxn | ---MMC | 0.28 |
| | +MMC | 0.58 |

A comparison of the productivity of Taq polymerase at reduced amounts in the PCR reaction mix. The area under the melt curve for each enzyme concentration was calculated and normalized with respect to the AUC for the enzyme concentration of 1 U/reaction mix under crowded conditions, denoted as MMC in the table; refers to Fc400 at 2.5 mg/ml.

(vi) Effects of Crowding on Reverse Transcriptase Activity

Figure 14A:
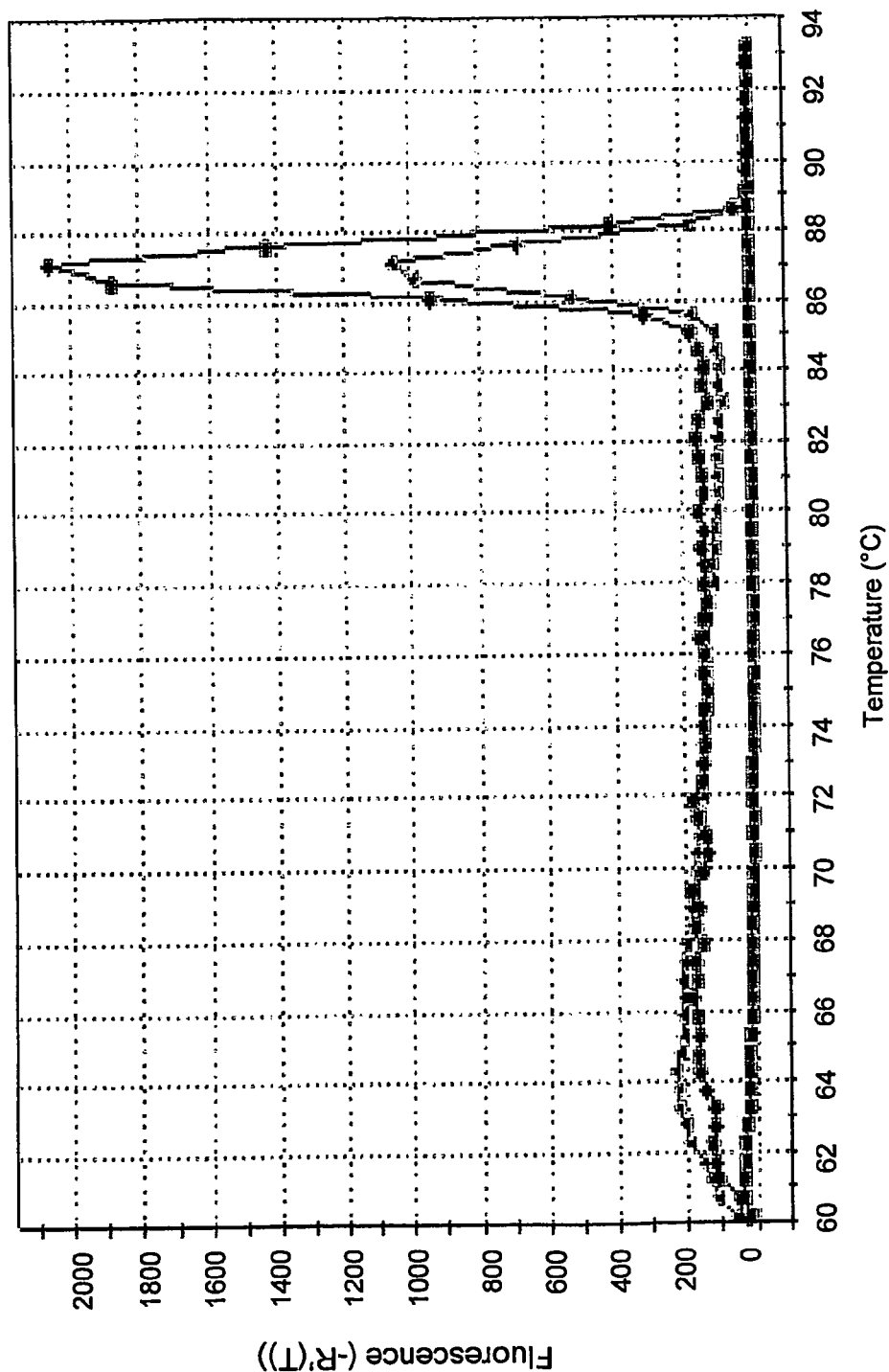
FIGS. 14A and B. Dissociation curves from real-time PCR after reverse transcription of mRNA under crowded conditions.

FIGS. 14A,B. Dissociation curves from real-time PCR after reverse transcription of RNA derived from adipose tissue using primers against aP2 gene, under crowded conditions. Area under the melt curve shows a higher value for (A) compared to (B). (A):Target DNA was derived from reverse transcription of mRNA under crowded conditions; (B):Target DNA was derived from reverse transcription of mRNA under uncrowded conditions.

After reverse transcribing the mRNA under crowded conditions, a PCR on the first strand cDNA was done to find out if there was an increase in the reverse transcript due to crowding. The target cDNA was diluted serially in two-fold fashion up to a one-sixteenth dilution and were used as templates for the PCR. The PCR itself was run under identical conditions for both the test and control samples.

Figure 14B:
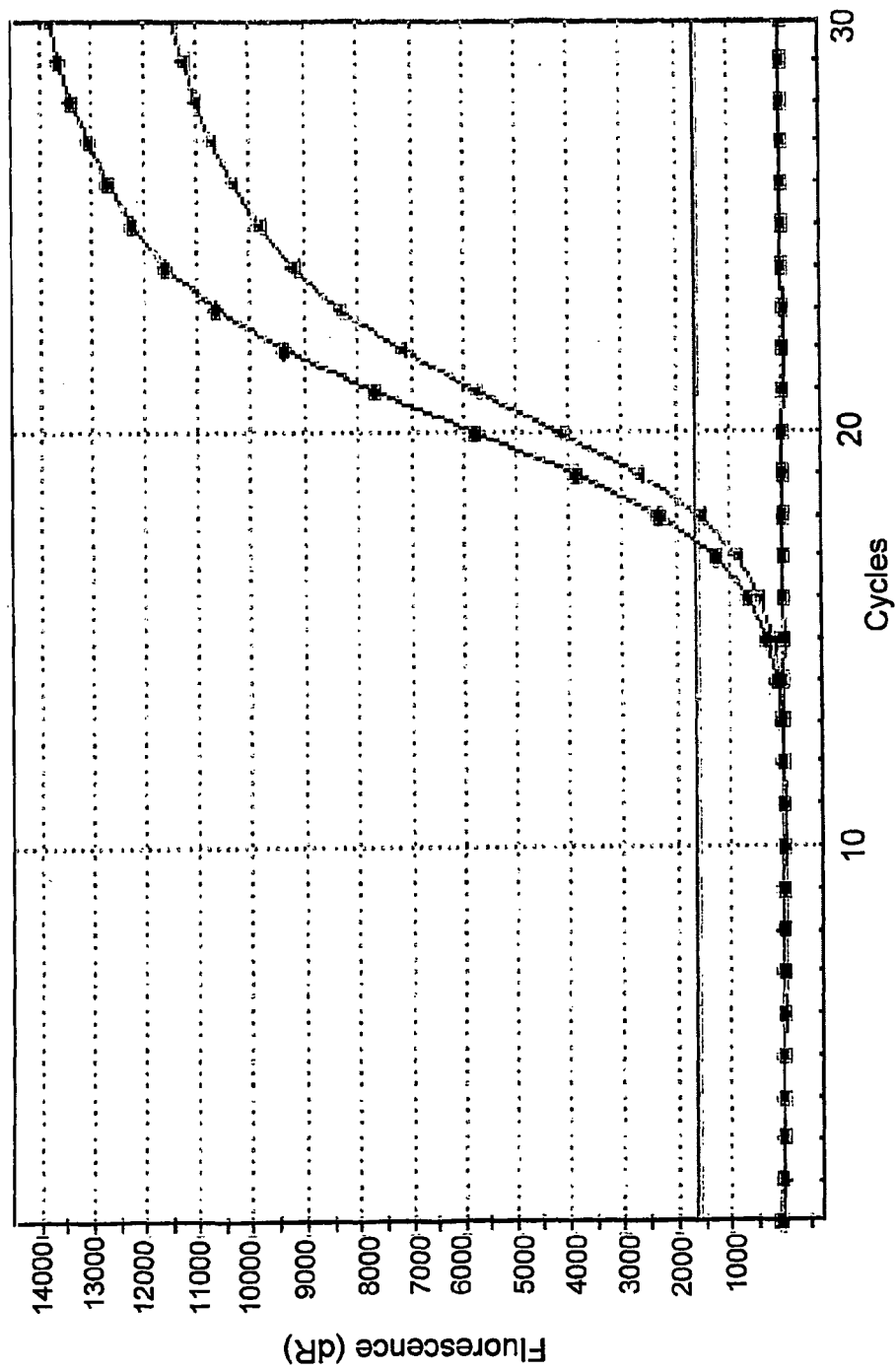

FIGS. 14 A and B show an amplification and dissociation profile of the PCR for the 1:4 diluted template. As can be appreciated from the curves (see FIG. 14A), the $C_T$ for the template (uncrowded—b) was found to be 18.13 whereas for the crowded condition(a), $C_T$=17.47. Thus there is a marginal increase in sensitivity, suggesting a greater concentration of the starting template that was obtained under crowded conditions.

Dissociation peaks were seen at ~87.5° C. that confirms the identity of the PCR product as aP2 from the predicted $T_m$ for this sequence.

In addition, the dissociation plots show that there is an astonishingly greater amount of the PCR product produced due to the template that was obtained under crowded conditions. A calculation of the area under the melt curves showed the following:

Area under curve A=6421 sq. units

Area under curve B=4827 sq. units

A difference of 33% in area under the melt curve

Thus, incorporating a crowder in the reverse transcription reaction yields a greater amount of second strand cDNA that is an indirect measure of an increased first strand DNA yield due to crowding.

Example 3

1. RNA Extraction

RNA was extracted from human WI-38 fibroblasts (American Tissue Culture Collection, VA, USA), adipocytes differentiated from human mesenchymal stem cells (Cambrex Bio Science, MD, USA) with the Adipogenic hMSC Differentiation BulletKit (Cambrex).

Extractions were performed with DEPC (Sigma)-treated water or the RNAqueous (Ambion Inc., TX, USA) according to the Manufacturer's protocol.

2. Reverse Transcriptase

Complementary DNA synthesis was carried out according to the Manufacturer's protocol for SuperScript II reverse transcriptase with oligo(dT) primers with the following modifications. Fc70 was added to the annealing buffer at a final concentration of 7.5 mg/ml. For the polymerization step, a final concentration of 7.5 mg/ml of Fc70 and 2.5 mg/ml of Fc400 were added to the reaction buffer.

3. Polymerase Chain Reaction

Two μl of cDNA where used as target for all PCRs in a reaction volume of 20 μl. The component concentrations for all PCRs were as follows, unless as otherwise stated: 1 U Platinum Taq. DNA polymerase in 1× reaction buffer, 300 nM primers and 3.0 mM $MgCl_2$. The thermal cycling program for all PCRs was the following, unless as otherwise stated: 94° C./5 min, 94° C./30 s, 56° C./30 s, 72° C./30 s, for (Collagen I set 1, 30; GAPDH, 35; aP2 and M13, 40; Collagen I set 2, 42) cycles with a final dissociation step of 60° C. to 94° C. at 1.1° C./s and ending with 25° C./30 s. The annealing temperature for aP2 and GAPDH was 56° C., and for Collagen I set 1 and set 2 was 55° C. Fluorescence was detected with SYBR Green I (Molecular Probes-Invitrogen). Primer sequences were: aP2, tactgggccaggaatttgac (SEQ ID NO:1), gtggaagtgacgaatttcat (SEQ ID NO:2); GAPDH, gtccactg-gcgtcttcacca (SEQ ID NO:3), gtggcagtgatggcatggac (SEQ ID NO:4); collagen I set 1, agccagcagatcgagaacat (SEQ ID NO:5), tcttgtccttggggttcttg (SEQ ID NO:6); M13, ttgcttccg-gtctggttc (SEQ ID NO:7), caccctcagagccaccac (SEQ ID NO:8); collagen I set 2, gtgctaaaggtgccaatggt (SEQ ID NO:9), ctcctcgctttccttcctct (SEQ ID NO:10).

Processivity Experiments

The M13 processivity assay for Taq. DNA polymerase was performed according to Bambara et al. Accordingly, 100 nM of primer (gtaaaacgacggccagt) (SEQ ID NO:11) were added to 100 nM ssM13 mp 18 DNA (New England Biolabs Inc., MA, USA) in buffer with 1 U Taq. DNA polymerase in the absence or presence of Fc400 at a final concentration of 2.5 mg/ml. The samples were heated to 94° C./5 min, cooled to 55° C./1 min followed by 72° C. for 1-5 min. The reactions were stopped by adding 50 mM EDTA and placed on ice before gel electrophoresis. For the reverse transcriptase processivity assay, a standard RT was performed without and with the macromolecules Fc70/Fc400 mixture, as above, following which one half of the reaction was subjected to digestion with RNase A (20 μg/ml) for 15 min at 37° C. Both the undigested and digested reaction portions were then separated on a denaturing 0.6% agarose gel.

Agarose Gel Electrophoresis

Reaction products were either resolved in 1×TAE agarose (Seakem, Me., USA) gels or in formamide-denaturing agarose gels (14) at the stipulated concentrations of 0.6 or 2.0%. The molecular weight markers were 1 kb (Promega Corporation, WI, USA), 50 and 100 bp (Invitrogen) DNA ladders. Post-staining was done with SYBR Gold (Molecular Probes-Invitrogen) and the images were captured with a Versadoc™

(Bio-Rad) and densitometric analysis was performed with Quantity One v4.5.2 (Bio-Rad).

Thermal Stressing of Taq. DNA Polymerase

Thermal stressing of Taq. DNA polymerase was performed in the absence and presence of the macromolecule Fc400 and small molecules trehalose and proline, individually, at final concentrations of 2.5, 100 and 113 mg/ml, respectively. They were dissolved in 1×PCR reaction buffer. Ten l reaction volumes with 2 U of enzyme were heated at 95° C. for 45 min. Following which 5 l of the stressed reaction was added to the standard GAPDH PCR and subjected to 40 thermal cycling events.

Calculation of the Area-Under-the-Curve and Late Phase PCR Efficiency

The method of Rasmussen et al. which uses the NCSS™ software was used to calculate the area-under-the-curve from the PCR dissociation curves raw data values derived from the Stratagene software MxPro v3.20. The late-phase efficiency of PCR amplification was calculated according to the method of Liu and Saint.

Results for Example 3

Sensitivity

Figure 15A:
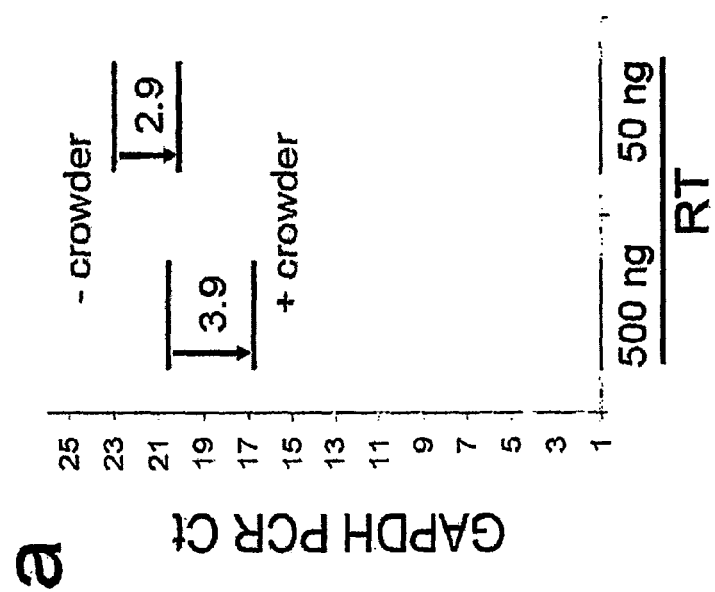
FIG. 15. Macromolecules enhance the sensitivity of RT and PCR assays. (a) The average Ct values for samples amplified with the GAPDH PCR from cDNA prepared in the presence and absence of the crowders Fc70 (7.5 mg/ml) and Fc400 (2.5 mg/ml). The amount of total RNA used for the RT was 500 and 50 ng. (b) Amplification plots (left panel) and dissociation curves (right panel) of the PCR samples. (c) Agarose gel demonstrating a specific 261 bp amplicon. (d) The average Ct values from samples amplified with the collagen I set 1 PCR in the presence (+crowder) (green or dark colour) and absence (−crowder)(orange or light colour) of crowders from cDNA prepared in the presence and absence of the same crowders, respectively. Crowders were as for (a). The amount of total RNA used for the RT was 1000 and 50 ng. (e) Amplification plots (left panel) and dissociation curves (right panel) of the PCR samples. (f) Agarose gel demonstrating a specific 250 bp amplicon. All the graphs show one replicate per PCR sample for display clarity. The agarose gels were 2% and the molecular weight standard (MW STD) was the 100 bp DNA Ladder. The −ve control was the PCR template-free control.
Figure 15B:
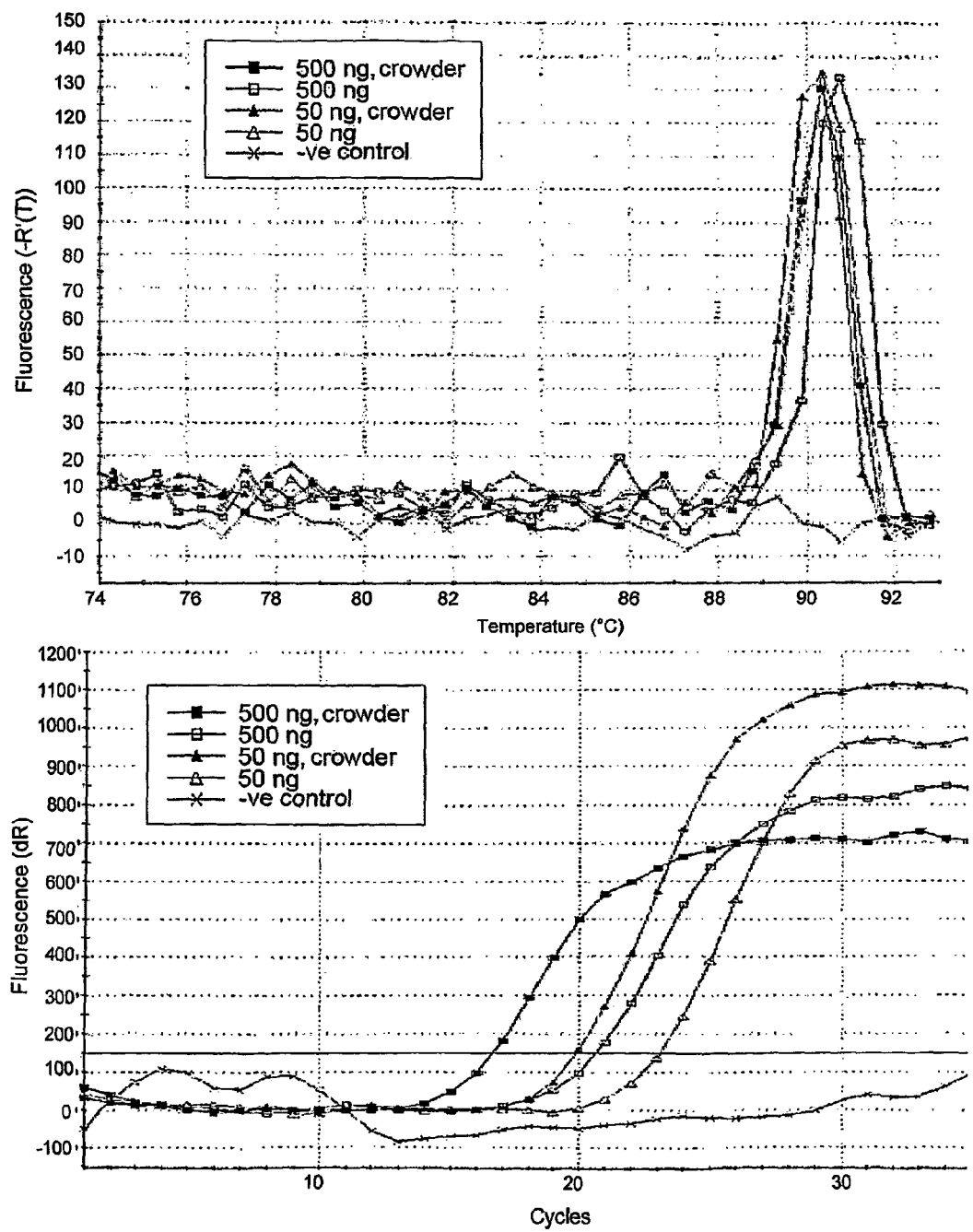
Figure 15:
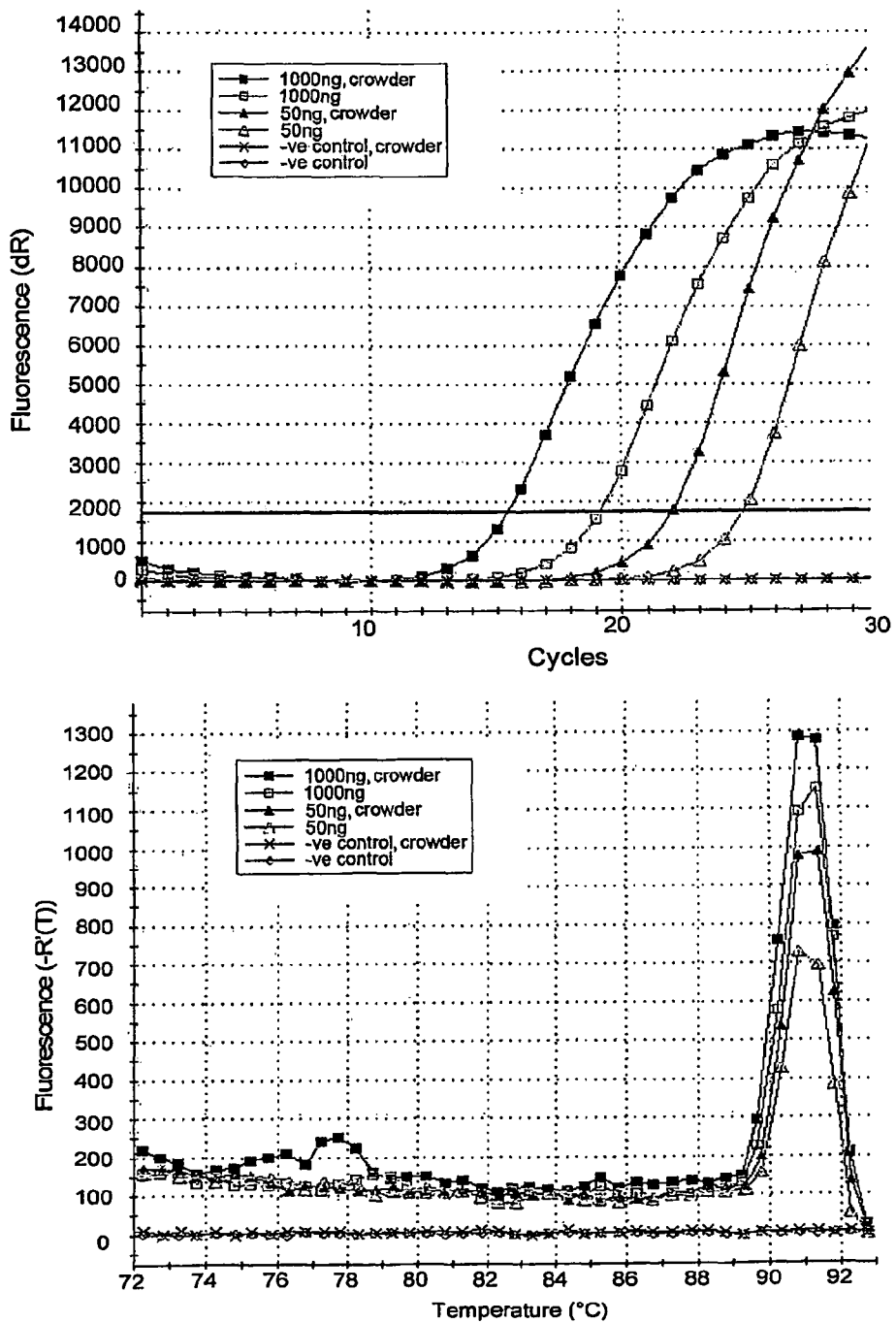
Figure 15:
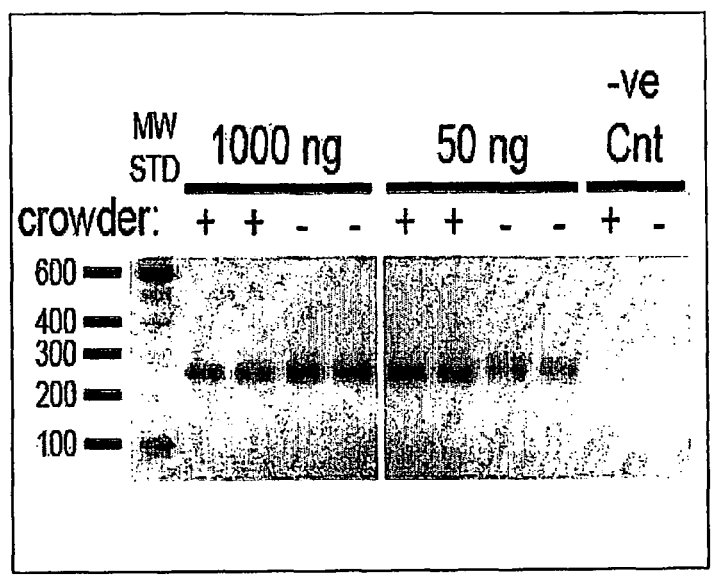

A key goal in PCR applications is sensitivity. It is defined as the minimum amount of target required for a specific PCR amplicon to be detected above background; given by the Ct for a real-time readout. Therefore, the lower the Ct value, the more sensitive is the PCR. We demonstrated that by adding certain macromolecules (Fc 70 and Fc 400) to a standard RT reaction, we dramatically enhanced its sensitivity. Reverse transcription was performed with 500 and 50 ng of total RNA starting material followed by amplification of a specific target, GAPDH, with a standard (i.e. non-crowded) PCR (FIG. 15). We attained a reduction in Ct value of 3.9 and 2.9, respectively (FIG. 15a) taken from the amplification plots (FIG. 15b, left panel). Theoretically, a gain in 1 Ct value is equivalent to an increase in 2-fold sensitivity. Considering that at the early exponential phase of a PCR the reaction rate is close to theoretical amplification, this equates to an average sensitivity gain of greater-than 8-fold. In fact, the PCR samples run with the RT prepared from 50 ng of total RNA in the presence of macromolecules demonstrated greater sensitivity than the RT prepared with 10-times (500 ng) the amount of RNA in the absence of macromolecules. The dissociation curves (FIG. 15b, right panel) in conjunction with the agarose gel electrophoresis (FIG. 15c) demonstrate that the PCR amplicons for all the treatments were the same. When we added macromolecules to both the RT and PCR we found an increase in sensitivity. The RT was performed in the presence and absence of macromolecules (as above) followed by amplification with collagen I PCR in the presence and absence of a macromolecule (Fc 400), respectively. There was a greater-than 3 Ct decrease when the reactions were performed in the presence of macromolecules (FIG. 15d; FIG. 15e, left panel). The dissociation curves (FIG. 15e, right panel) and agarose gel (FIG. 15f) demonstrate that the amplicons were identical.

PCR Yield and Late Exponential Phase Efficiency

Figure 16:
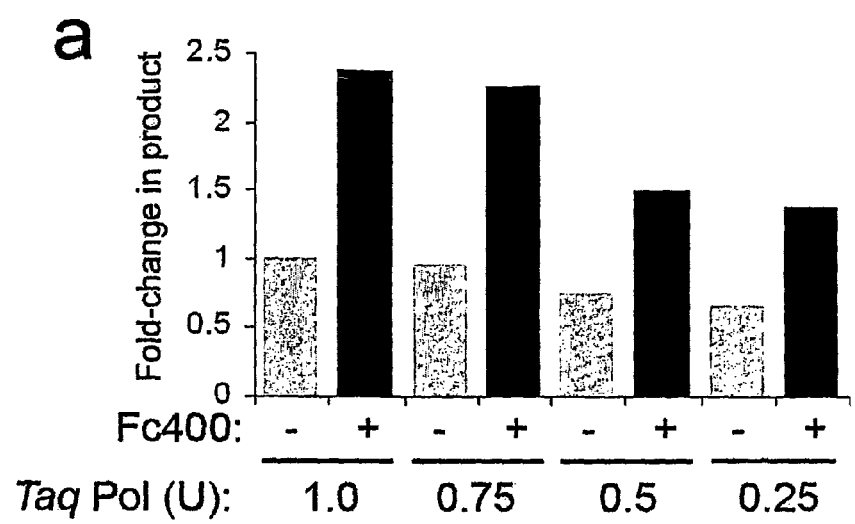
FIG. 16. Specific PCR amplicon yield and Taq. DNA polymerase thermal stability are enhanced with macromolecules. (a) A range of Taq. DNA polymerase concentrations (1-0.25 U) were used to amplify the aP2 product in the absence (−) and presence (+) of Fc400 (2.5 mg/ml). (b) Amplification plots (left panel) and dissociation curves (right panel) for the PCR samples performed with 1 and 0.25 U of enzyme are only shown, for display clarity. (c) Taq. DNA polymerase was thermally stressed in the absence (None) and presence of 2.5 mg/ml Fc400, 100 mg/ml trehalose (Trh), or 113 mg/ml proline (Pro) and then the samples were subjected to a GAPDH PCR. Two replicates per treatment are shown on a 2% agarose gel demonstrating the presence of discrete bands of the correct size, 261 bp. (d) Amplification plots (left panel) and dissociation curves (right panel) are shown for one replicate per treatment for display clarity. The molecular weight standard (MW STD) was the 100 bp DNA Ladder. The −ve Cnt (control) was the PCR template-free control.
Figure 16B:
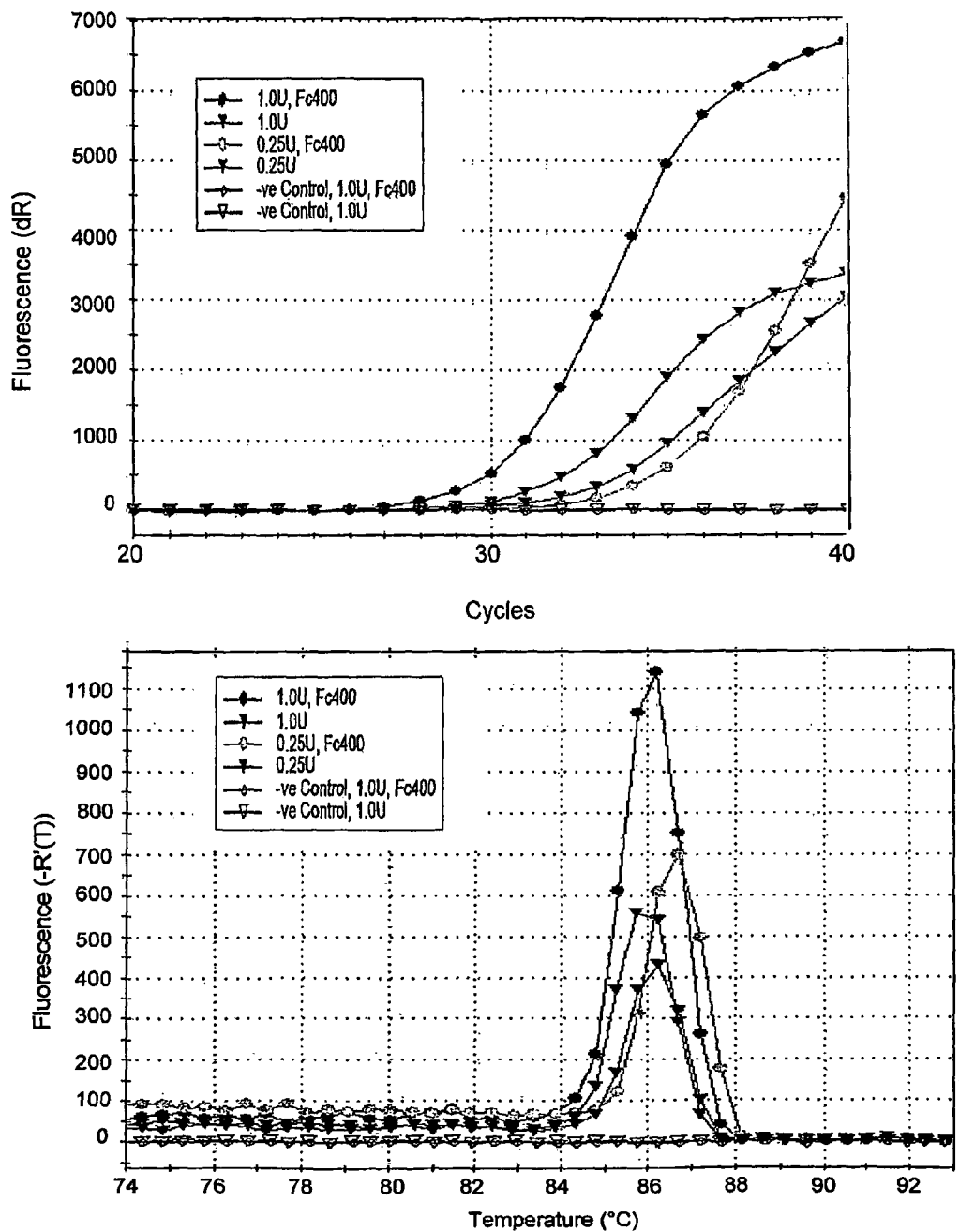

Overall PCR yield was considerably enhanced under crowded conditions, resulting in many-fold greater yield in specific amplicon for aP2 (FIG. 16a). Amplifications were performed in the absence and presence of Fc400 with decreasing amounts of Taq. DNA polymerase. Even at one-quarter of the Taq. DNA polymerase concentration (0.25 unit (U)) in the presence of crowding the yield was 6-fold greater than the yield from the reaction with 1 U enzyme without crowding, per U enzyme. The graph values were taken from integrating the area under the dissociation curve for each sample (FIG. 16b, right panel) which represents the total quantity of specific PCR product. The productivity (i.e. yield) of a PCR is generally determined by the reaction efficiency, which normally decreases at the late exponential amplification phase. Thus, the exponential amplification that is theoretically predicted and can be attained by efficient reactions (efficiency close to 100%) is no longer seen. For this reason the Ct is measured as close to the "take-off" Ct as the background permits. In the aP2 PCR example above, the addition of Fc400 resulted in 2-fold greater value for the slope at exponential late-phase which correlates with faster reaction kinetics and thereby efficiency, thus accounting for the greater yield. In addition, the duration of the exponential phase in the presence of the macromolecule was longer, adding to greater yield.

Thermal Stability

Figure 16C:
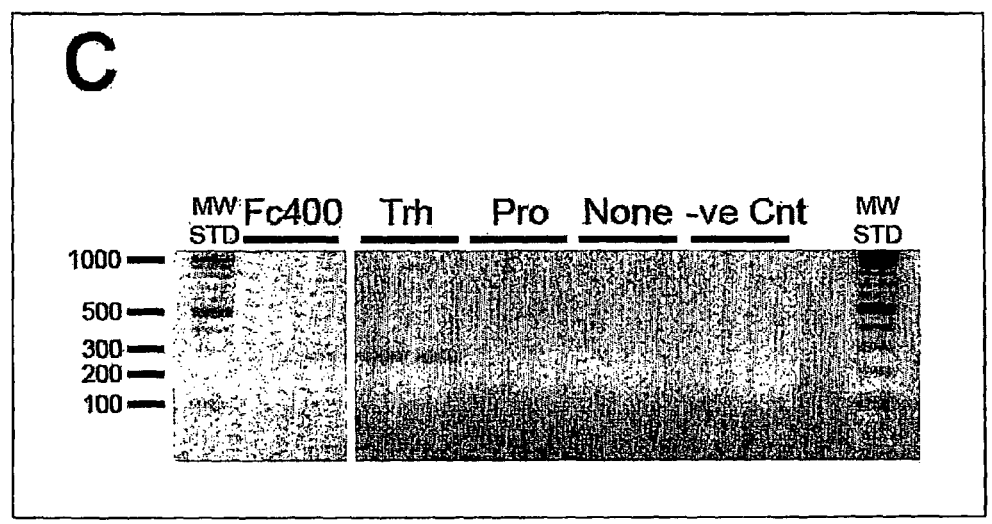

The key parameter of Taq. DNA polymerase that has made PCR so practical is the enzyme's ability to function at high temperatures. However, the present conditions under-which PCR is performed are far removed from the crowded interior environment of *Thermus aquaticus* where the enzyme was isolated from. We tested the thermal stabilizing property of Fc400 for Taq. DNA polymerase and compared against known thermal stabilizers, trehalose and proline. The enzyme was heat-stressed in the presence and absence of the macromolecule or compatible solutes prior to the PCR proper in the presence of the same. Only the presence of Fc400 and trehalose preserved the Taq. DNA polymerase's enzymatic activity (FIGS. 16c and 16d). In the presence of proline or in the absence of the other additives reliable enzymatic activity was lost after heat stress. The 1° C. difference in the Tm of the amplicons (FIG. 16d, right panel) is not surprising since trehalose is known to reduce the melting temperature of DNA duplexes.

Processivity

Figure 17C:
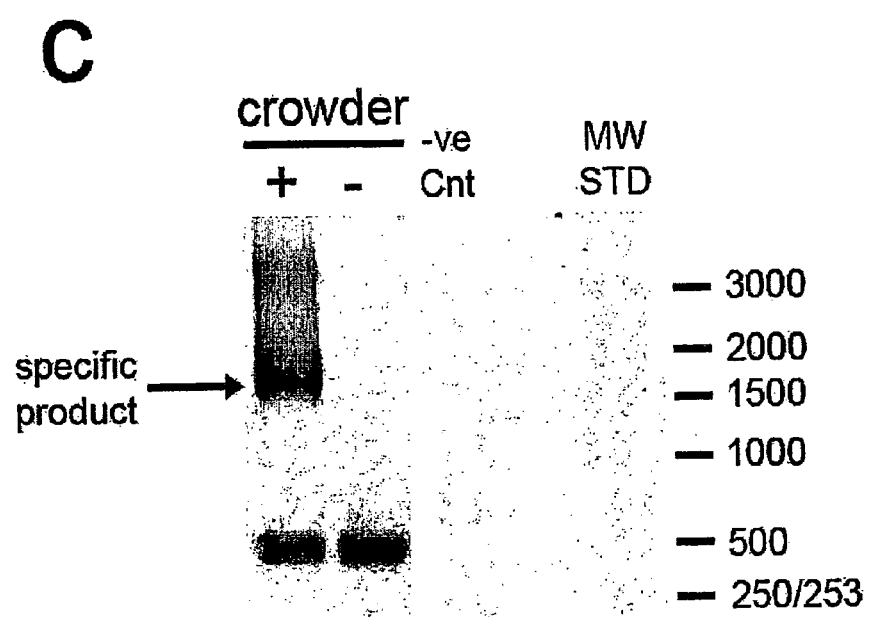
FIG. 17. Macromolecular crowding enhances enzyme processivity. (a) The ssM13 processivity assay for Taq. DNA polymerase was performed in the absence and presence of Fc400. Densitometric analysis of the total amount of ssDNA products (left panel) and their relative migration (right panel) through a denaturing 0.6% agarose gel (b). The −ve Cnt was the enzyme-free negative control. (c) A non-denaturing agarose gel of the long M13 PCR products amplified in the presence of mixed Fc70 and Fc400 (15 and 5 mg/ml, respectively) and in their absence. One ng of ssM 13 was used as target and the extension time was 40 s. The −ve Cnt was the template-free negative control. The arrow indicates the specific target which is 1547 bp. A standard RT reaction was preformed in the absence and presence of Fc70/Fc400 with 500 ng of total RNA. (d) Densitometric analysis of total products before (total RNA+cDNA) and after (cDNA) RNase A digestion (left panel) and their relative migrations (right panel) through a denaturing 0.6% agarose gels (e). "−ve" is the enzyme negative control. All graphs and migration profiles were derived from the respective agarose gels. The molecular weight marker (MW STD) was the 1 Kb DNA Ladder. Gel images (b,c) are composites of the respective gels omitting irrelevant sections. Abbreviations: dgt, digested; undgt, undigested.
Figure 17D:
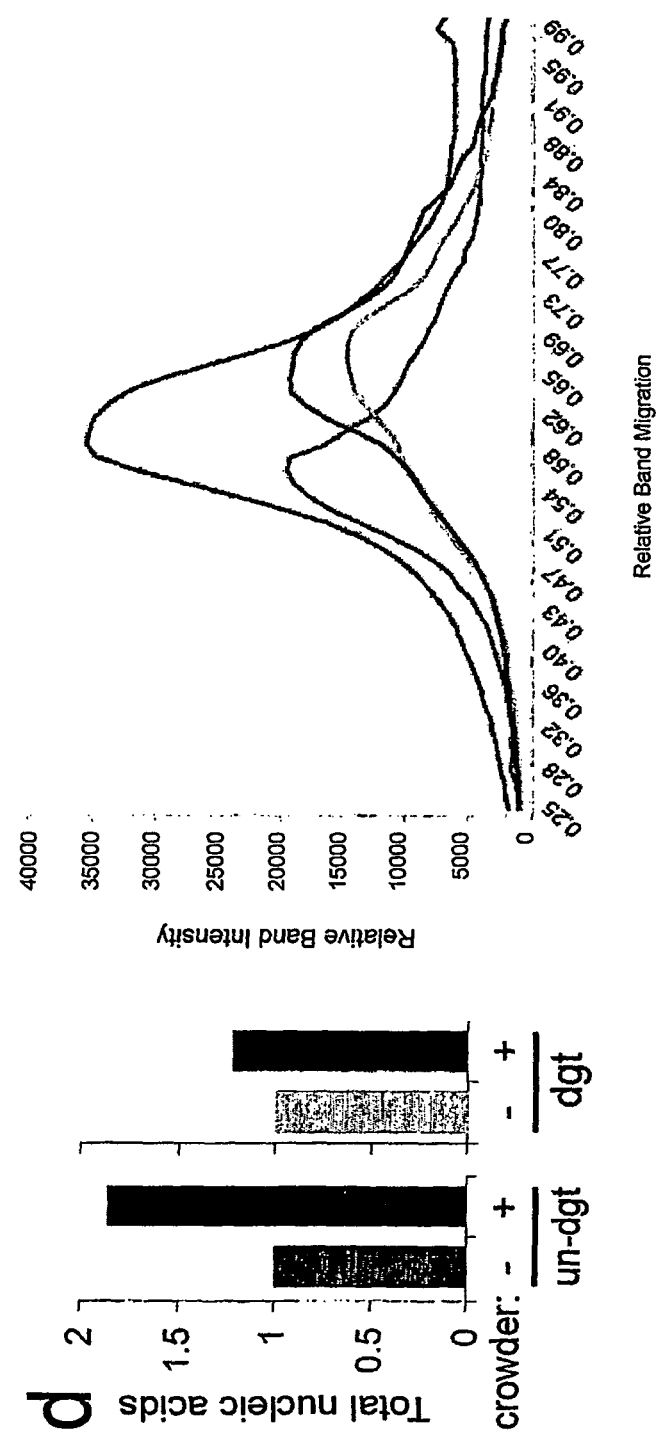
Figure 17E:
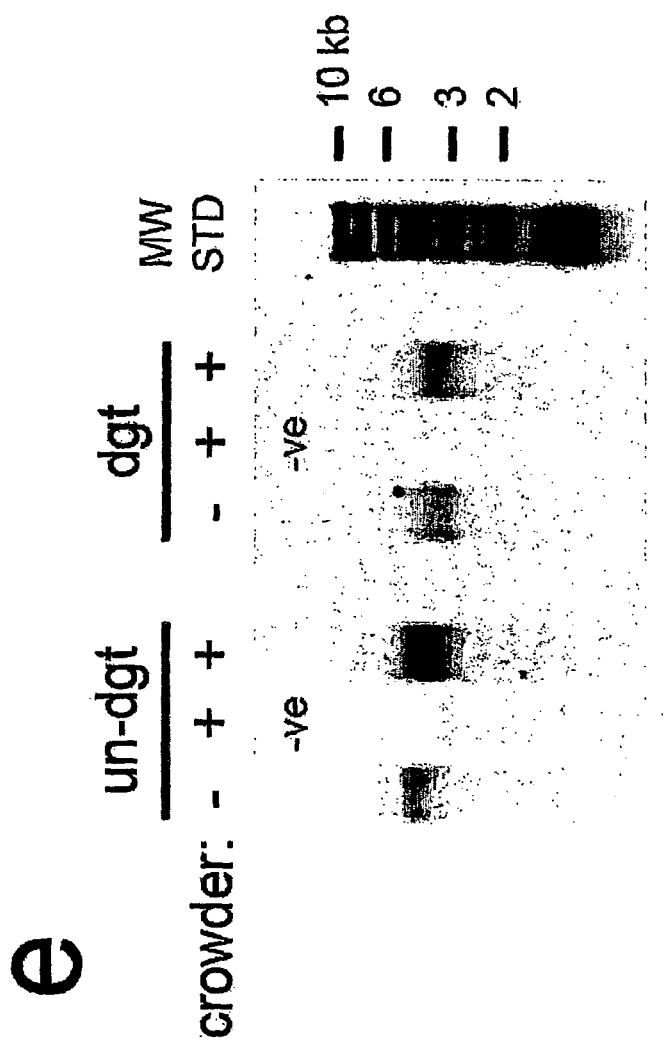

Increased processivity is the ability of enzymes such as Taq. DNA polymerase and reverse transcriptase to produce more and longer complementary strands of nucleic acids. Poor initial enzyme-nucleic acid polymer complex and its premature detachment result in low processivity, a common scenario in vitro. In order to assess the ability of macromolecules to enhance processivity of Taq. DNA polymerase, we performed a classical single-stranded M13 (ssM13) processivity assay in the absence and presence of macromolecules. This involved one priming and polymerization event which was then run under denaturing agarose gel conditions and subjected to densitometric analysis. The presence of Fc400 resulted in an average increase in product of 15% (FIG. 17a, left panel). More significantly, the presence of the crowder resulted in larger DNA fragments which is apparent from the relative migration profiles (FIG. 17a, right panel) derived from the denaturing agarose gel (FIG. 17b). The enhanced processivity induced by crowding was clearly apparent with the long M13 PCR assay (FIG. 17c). The addition of a macromolecule mixture of Fc70/Fc400 enabled the amplification of the correct amplicon (1547 bp) under conditions of limited extension time (40 s). In contrast, the reaction carried out in the absence of crowding could not amplify the correct amplicon. Reverse transcriptase binds to the RNA-primer (e.g. oligo(dT)) hybrid and in a single turnover run, a complementary cDNA is synthesized. We carried out cDNA synthesis in the absence and presence of crowding additives (Fc70-Fc400). Densitometric analysis of the denaturing agarose gel of the reaction products (FIG. 17e) demonstrated an increase of total cDNA produced of 86 and 22% for the crowded condition before and after digestion of the total RNA, respectively (FIG. 17d).

Specificity

We were unable to amplify a particular collagen I template target region through standard RT-PCR due to its long distance form the olig(dT) priming site (~4390 bp; NM_000088). However, when a mixture of Fc70 and Fc400 was added to the PCR the specific product was clearly detected at the lower range of primer concentrations (100-300 nM) (FIG. 18). The higher primer concentrations resulted in high background but the specific product was still present and dominated the amplicons that were generated in the presence of macromolecules, whereas the reactions preformed in the absence of macromolecules only possessed non-specific products. The success of the PCR was due to enhanced specificity of the primers as a result of crowding.

Example 4

A Study of the Effects of Peg 4000 Da Compared with Macromolecular Crowding Agents Fc 400-Fc70 Combination on PCR Profile The experiment was carried out according to Example 3. PEG final concentrations tested were 2.5 mg/ml, 5 mg/ml and 10 mg/ml.

PCR runs were done on cDNA reverse transcribed from Wi-38 fibroblast mRNA. The target was a 261-bp GAPDH sequence and the PCR conditions were:
94 deg C./5 minutes
35 cycles of 95 deg C./15"→156 deg C./20"→472 deg C./30"
Followed by: 60 deg C.→994 deg C.→25 deg C.

Figure 19:
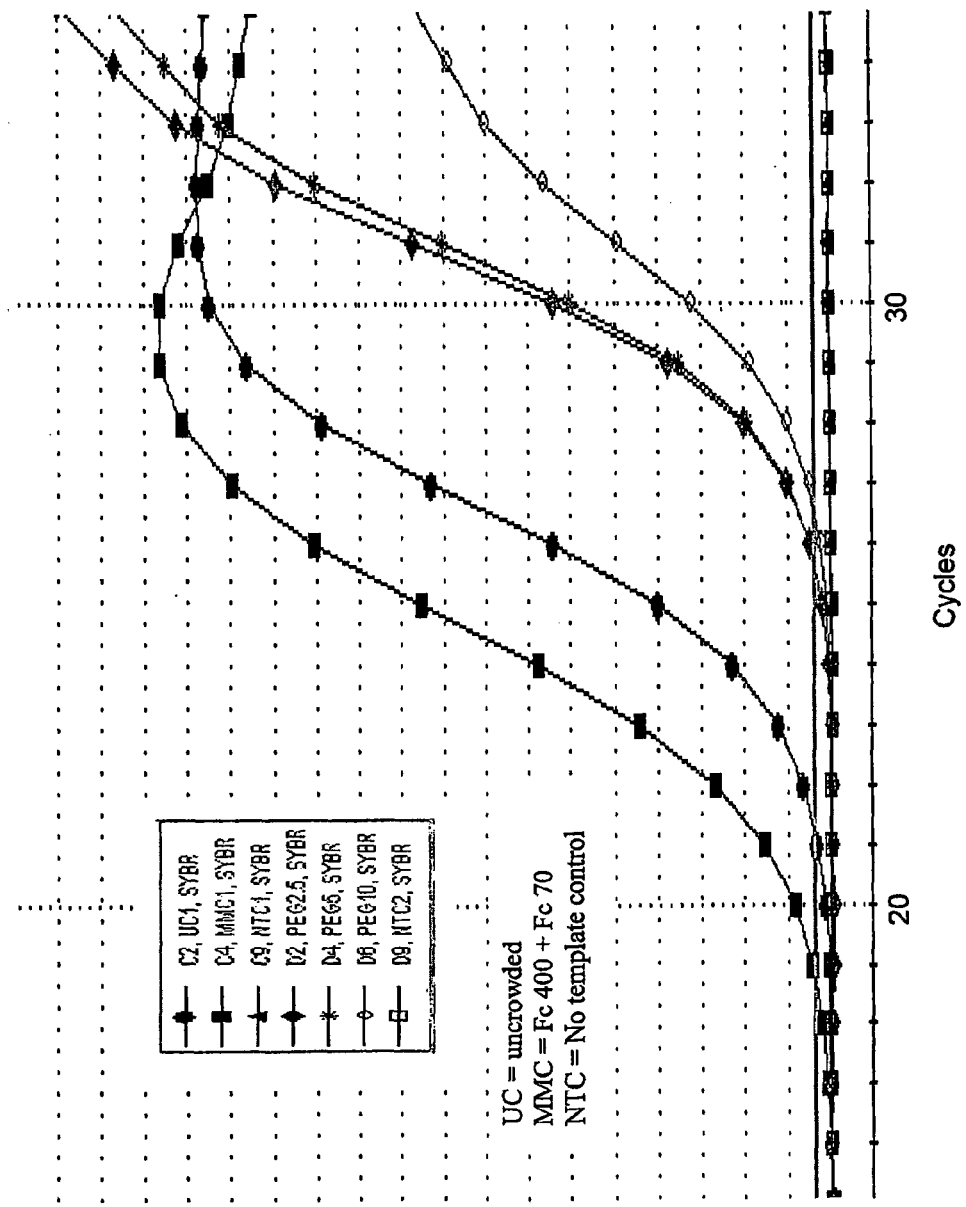
FIGS. 19 and 20: PCR with crowders show a ~2 CT decrease compared to uncrowded and hence greater sensitivity. PCR with PEG at all 3 tested concentrations show a decrease in sensitivity relative to controls; Dissociation profiles show a melt peak of 90° C. typical of our GAPDH sequence. UC=uncrowded; MMC=Fc 400+Fc 70; NTC=No template control.
Figure 20:
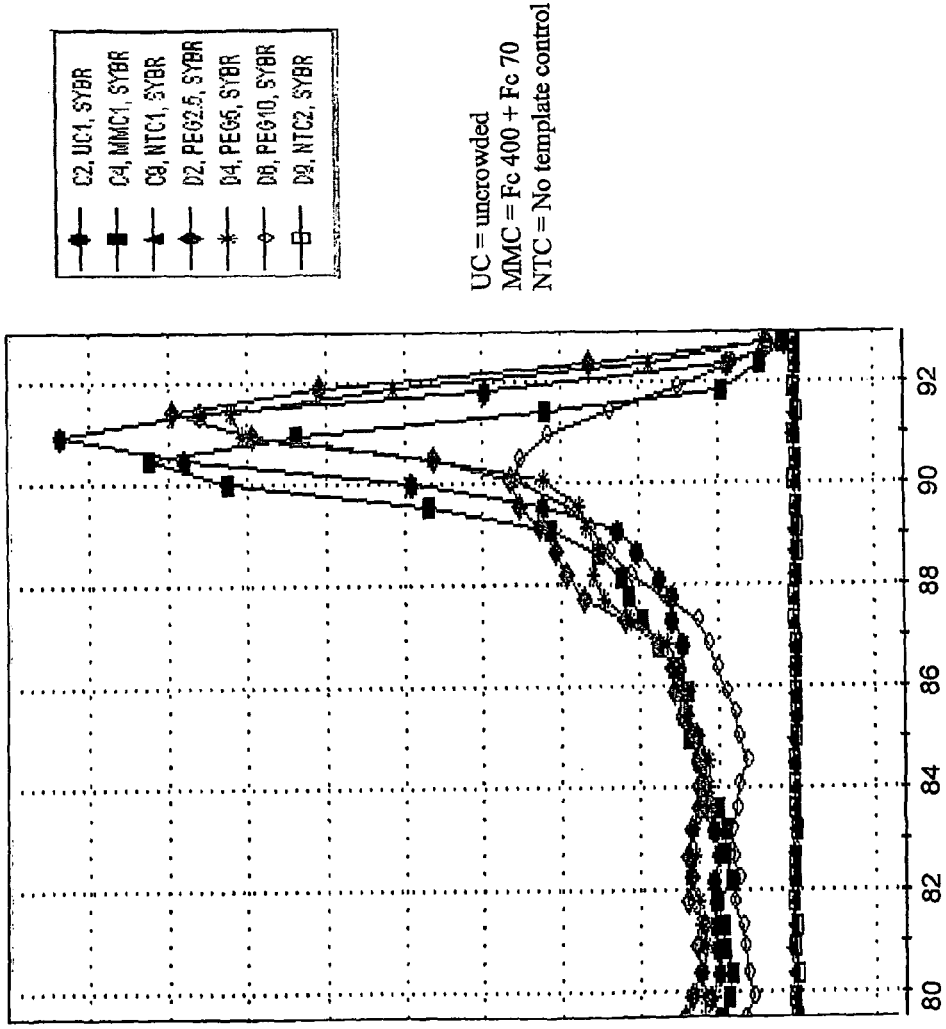
Figures 21A, 21B:
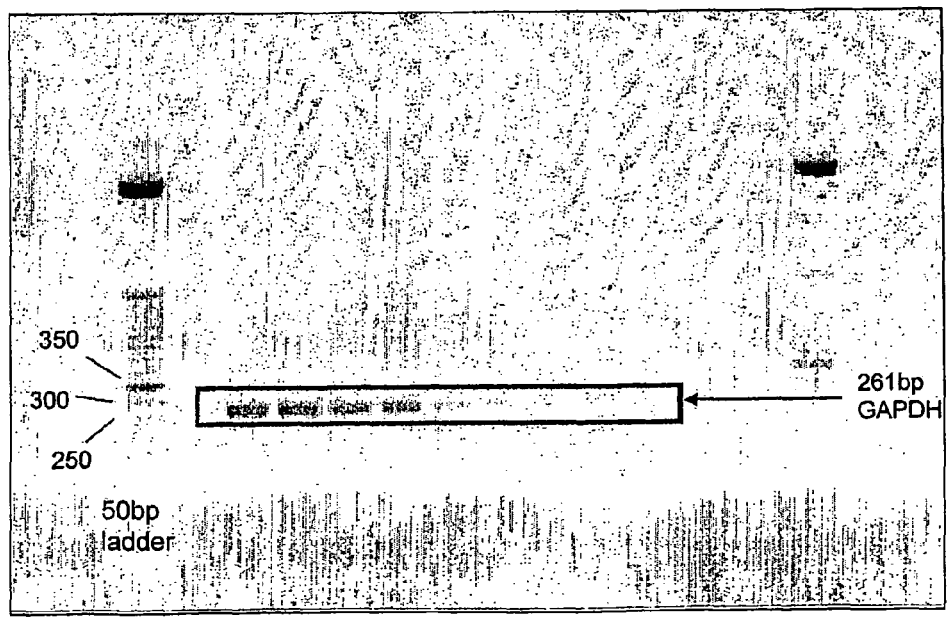
FIGS. 21 (A, B): The figures confirm the CT values of the PCR products; 2% Agarose gel confirms the identity of the PCR product at 261 bp.

The sample volumes were 20 µl/reaction in duplicates. The PCR products were then run on a 2% Agarose gel and stained with SYBR Gold for visualization of bands on a Versadoc imaging system Bio-Rad). In FIGS. 19 and 20, PCR with crowders show a ~2 CT decrease compared to uncrowded and hence greater sensitivity. However, PCR with PEG at all 3 tested concentrations showed a decrease in sensitivity relative to controls. Dissociation profiles showed a melt peak of 91 deg C. typical of our GAPDH sequence. FIG. 21 (A, B) confirm the CT values of the PCR products; 2% Agarose gel confirms the identity of the PCR product at 261 bp.

Analysis of PCR Results of Example 4 and Discussion

The threshold CT for macromolecular crowders showed a 2 cycle decrease compared to the uncrowded condition. Therefore, sensitivity due to macromolecular crowder combination of Fc400 and Fc70 showed a 4-5 fold increase in sensitivity than uncrowded. However, at similar w/v concentrations, PEG 4000 showed a >2 cycle increase in $C_T$, thus PEG 4000 is not an ideal crowding agent.

Example 5

A Study of the Effects of Macromolecular Crowding on the Restriction Endonuclease Digestion of Lambda DNA 1. The optimal conditions that would give complete digestion of λ DNA by the restriction enzyme, EcoRI, under standard (uncrowded) conditions was first established. The optimal conditions established as follows: Target lambda DNA (Promega Inc, WI, USA) 0.25 µg/ul; temperature of incubation: 37° C.; time of incubation: 1 hour; enzyme quantity: 2 units of EcoRI (New England Biolabs, USA) in a 25 µl reaction mix.

2. Then, the suboptimal condition, where DNA is not or incompletely digested under standard (uncrowded) conditions, was achieved by: (1) reducing the amount of the enzyme EcoRI by one-tenth; at 0.2 U per reaction, and (2) reducing the temperature to 25° C.

3. Digestion runs were then carried out under crowded and uncrowded conditions by crowding the reaction mixes at suboptimal conditions (see above) as follows: Ficoll 400 at 2.5 mg/ml, 5 mg/ml, 10 mg/ml, 12.5 mg/ml, 15 mg/ml, 20 mg/ml; ND670 at 125 µg/ml, 250 µg/ml, 375 µg/ml, and 500 µg/ml.

4. After running the reactions, the reactions were stopped using a stop solution containing 50 mM EDTA at 5 µl/reaction mix and kept on ice for 5 minutes.

5. The digested fragments were identified using agarose gel electrophoresis as in example 1 with modifications as follows: A 0.4% agarose gel electrophoresis was run and bands identified by ethidium bromide staining.

Results for Example 5

Effects of Crowding on the Activity of Restriction Endonuclease EcoRI

Figure 22:
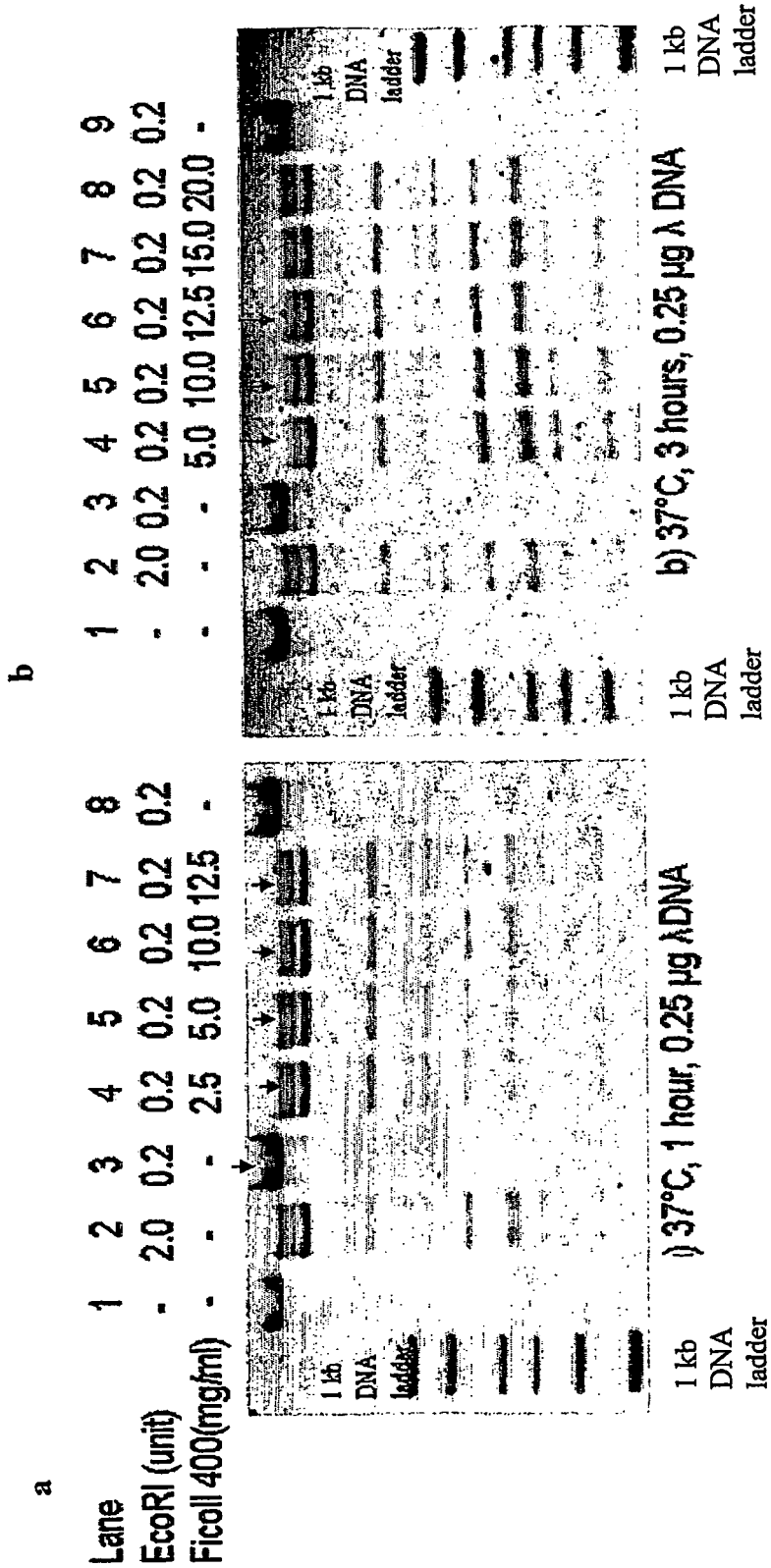
FIGS. 22(a, b): The effect of crowding on the activity of Eco RI using Ficoll 400: a) Lane 1: undigested-uncrowded control; Lane 2, 3 & 8: uncrowded controls; lane 2: 2 units EcoRI, lanes 3&8: 0.2 unit EcoRI. Lanes 4-7: crowded by different concentrations of Ficoll 400, at 0.2 unit of EcoRI. b) Lane 1: undigested-uncrowded control; Lane 2, 3 & 9: uncrowded controls; lane 2: 2 units EcoRI, lanes 3& 9: 0.2 unit EcoRI. Lanes 4-8: crowded by different concentrations of Ficoll 400, at 0.2 unit of EcoRI FIGS. 23(a, b): Effect of crowding using Neutral Dextran (ND) 670. (a) Lane 1: undigested-uncrowded control; Lanes 2, 3, 8 & 9: uncrowded controls; lanes 2 & 9: 2 units EcoRI and lanes 3 & 8: 0.2 unit EcoRI. Lanes 4-7: crowded by different concentrations of Neutral Dextran (ND) 670, at 0.2 unit EcoRI. (b) Lane 1: undigested-uncrowded control; Lanes 2 & 3: uncrowded controls; lane 2: 2 units EcoRI; lane 3: 0.2 unit EcoRI. Lanes 4-8: crowded by different concentrations of Neutral Dextran (ND) 670, at 0.2 unit of EcoRI.

Under uncrowded conditions (FIG. 22a; blue arrow—lane 3), there was no digestion using 0.2 unit of EcoRI after 1 hour of incubation at 37° C. Therefore the reaction conditions have been rendered sub-optimal for any digestion to be carried out by the enzyme.

However, there is evidence of a definite digestion, although not complete, under crowded conditions due to Ficoll 400 at 0.2 unit of EcoRI per reaction (FIG. 22a; red arrows—lanes 4 to 7). Thus a digestion was realized under crowded conditions even with a tenth of the routinely used enzyme amounts in a restriction digestion reaction.

We then explored if extended incubation could bring about more complete digestion profile for all the samples. However, it was observed that the results did not differ much after 3 hours of incubation compared with that after 1 hour incubation under uncrowded conditions (FIG. 22b). This suggests that the enzyme activity is saturated/inactivated well before the 3 hour time period and hence no increase was observable after this time.

But under crowded conditions, there was a more complete digestion at 3 of the 5 concentrations of Fc 400 at which crowding was set-up (FIG. 22 b; see red arrows)—lanes 4 to 6. Thus crowding was able to maintain the activity of the enzyme even after 3 hours at 37° C.

Thus crowding stabilized the enzyme at longer incubation times at the temperature mentioned above.

Neutral Dextran 670 as the Crowder

Under uncrowded conditions (FIG. 22a; blue arrow—lane 3), there was no digestion using 0.2 unit of EcoRI after 1 hour of incubation at 37° C. Therefore the reaction conditions have been rendered sub-optimal for any digestion to be carried out by the enzyme.

However, there is evidence of a definite digestion, although not complete, under crowded conditions due to ND 670 at 0.2 unit of EcoRI per reaction (FIG. 23a; arrows). Thus a digestion was realized under crowded conditions even with a tenth of the routinely used enzyme amounts in a restriction digestion reaction. We then explored if extended incubation could bring about more complete digestion profile for all the samples. However, it was observed that the results did not differ much after 3 hours of incubation compared with that after 1 hour incubation under uncrowded conditions (FIG. 23b). This suggests that the enzyme activity is saturated/inactivated well before the 3 hour time period and hence no increase was observable after this time.

Figure 23:
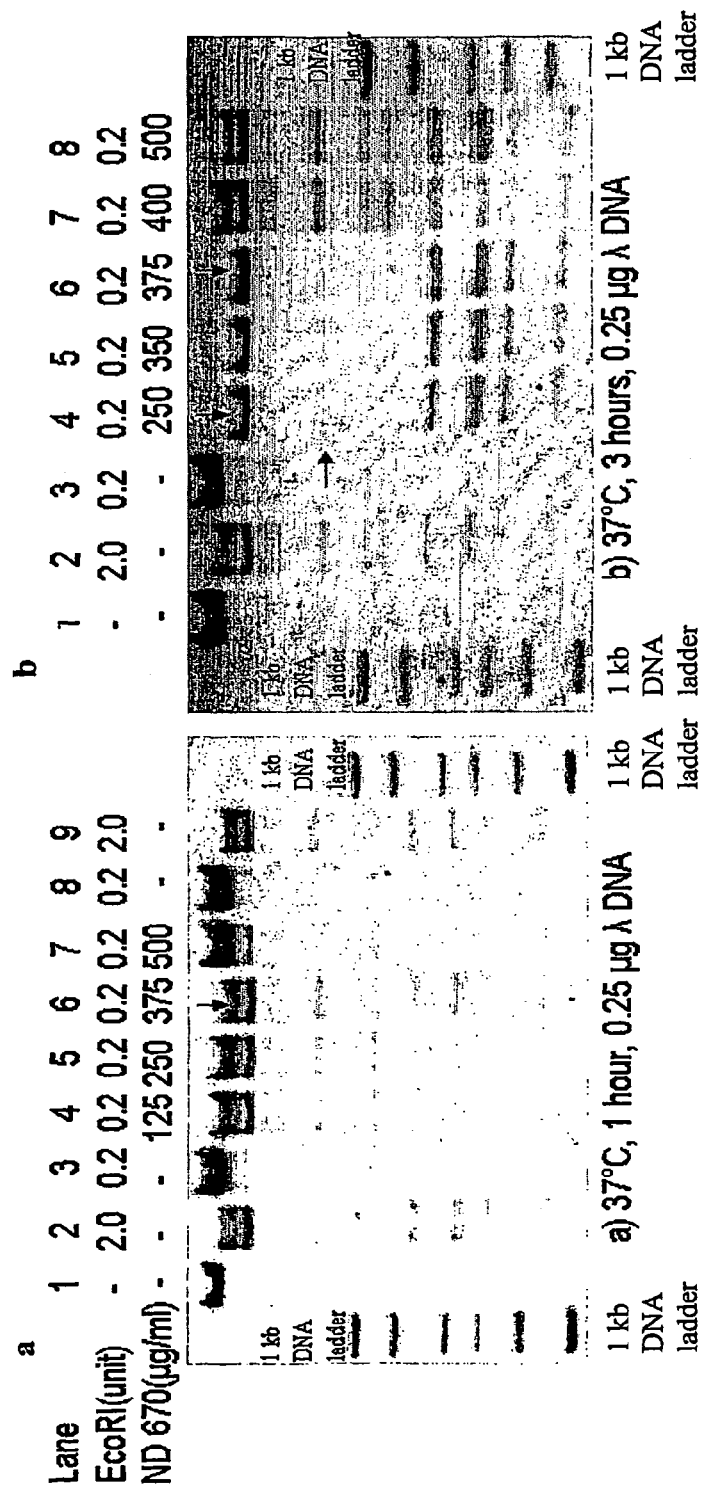

But under crowded conditions, there was a more complete digestion at 3 of the 5 concentrations at which crowding was set-up (FIG. 23 b; see arrows). In lanes 4-6 in FIG. 23b it can be seen that the DNA is nearly completely digested compared to lanes 4-6 in FIG. 23a. This means that crowding would indeed stabilize the enzyme and extend its active half-life.

Thus crowding stabilized the enzyme at longer incubation times at the temperature mentioned above.

Effect of Crowding on Restriction Digestion Reaction at Reduced Temperatures

Under room temperature, EcoRI is more active under crowded environment than uncrowded environment.

Figure 24:
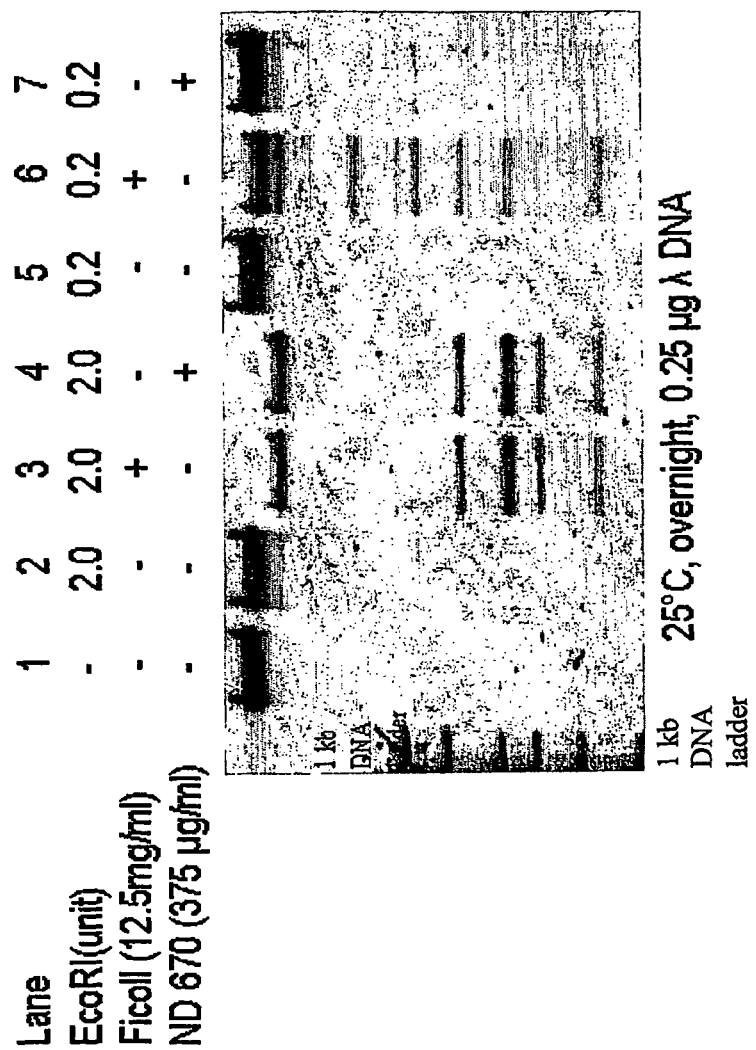
FIG. 24: restriction digestion reaction at reduced temperatures: Lane 1: undigested and uncrowded control. Lanes 2-4: 2.0 unit of EcoRI; lane 2: uncrowded, lane 3: crowded by Ficoll 400; lane 4: crowded by Neutral Dextran (ND) 670. Lane 5-7: 0.2 unit of EcoRI; lane 5 uncrowded, lane 6 crowded by Ficoll 400 and lane 7 crowded by Neutral Dextran 670.

In FIG. 24, lanes 3 & 4, which were crowded by Ficoll 400(12.5 mg/ml) and ND 670(375 µg/ml), complete digestion occurred while in lane 1 which was not crowded, the DNA was incompletely digested.

The results preliminarily indicate that even when temperature conditions are sub-optimal, the crowded conditions enable the reaction to occur.

LIST OF REFERENCES

1. Bambara, R. A., Uyemura, D. and Choi, T. (1978) On the processive mechanism of *Escherichia coli* DNA polymerase I. *J. Bid. Chem.*, 253, 413-423.
2. Chebotareva N A, Kurganov B I, Livanova N B. Biochemical effects of molecular crowding. *Biochemistry* (Mosc). 2004 November; 69(11):1239-51.
3. Cheung, M S. Klimov, D, and Thirumalai D. Molecular crowding enhances native state stability and refolding rates of globular proteins. *Proc Natl Acad Sci, USA* (2005), 102 (13), 4753-58.
4. Chomczynski P and Sacchi N. (1987). Anal Biochem 162, 156
5. Ellis R J. Macromolecular crowding: obvious but under-appreciated. *Trends Biochem Sci.* 2001 October; 26(10): 597-604.
6. Gottlieb, J., Marcy, A. I., Coen, D. M. & Challberg, M. D. The herpes simplex virus type 1 UL42 gene product: a subunit of DNA polymerase that functions to increase processivity. J. Virol., 64, 5976±5987 (1990)
7. Gronthos S, Zannettino A C W, Hay S J, Shi S, Graves S E, Kortesidis A, and Simmons P J. Molecular and cellular characterization of highly purified stromal stem cells derived from human bone marrow. *J cell Sci,* 2003, 116, 1827-35
8. Kotewicz M L, D'Alessio J M, Driftmier K M, Blodgett K P, and Gerard G F. (1985) *Gene* 35, 249.
9. Liu, W. and Saint, D. A. (2002) A new quantitative method of real time reverse transcription polymerase chain reaction assay based on simulation of polymerase chain reaction kinetics. *Anal. Biochem.*, 302, 52-59.
10. Livak, K. 1997. ABI Prism 7700 Sequence Detection System, User Bulletin 2. PE Applied Biosystems, Foster City, Calif.
11. Minton A P. Protein folding: Thickening the broth. Curr Bio, 2000, R97-R99
12. Minton A P. The influence of macromolecular crowding and macromolecular confinement on biochemical reactions in physiological media. *J Biol Chem.* 2001 Apr. 6; 276(14):10577-80. Epub 2001 Feb. 15.
13. Motz, M., et al., J. Biol. Chem. May 3, 2002; 277 (18); 16179-88).
14. Ponchel F, Toomes C, Bransfield K, Leong F T, Douglas S H, Field S L, Bell S M, Combaret V, Puisieux A, Mighell A J, Robinson P A, Inglehearn C F, Isaacs J D and Markham A F. Real-time PCR based on SYBR-Green I fluorescence: An alternative to the Taq Man assay for a relative quantification of gene rearrangements, gene amplifications and micro gene deletions. *BMC Biotechnology* 2003, 3:18
15. Rasmussen, R., Morrison, T., Hermann, M. and Wittwer, C. (1998) Quantitative PCR by continuous fluorescence monitoring of a double strand DNA specific binding dye. *Biochemica,* 2, 8-11.
16. Schnell S and Mendoza C., Theoretical Description of the Polymerase Chain Reaction. *J. Theor. Biol.*, (1997), 188, 313-318
17. Spiess, A. N. and Ivell, R. A. (2002) Highly efficient method for long-chain cDNA synthesis using trehalose and betaine. *Anal. Biochem.*, 301, 168-174.
18. Spiess A N, Mueller N, and Ivell R. Trehalose Is a Potent PCR Enhancer: Lowering of DNA Melting Temperature and Thermal Stabilization of Taq Polymerase by the Disaccharide Trehalose. *Clinical Chemistry* 50, No. 7, 2004
19. Tokuriki N, Kinjo M, Negi S, Hoshino M, Goto Y, Urabe I, Yomo T., Protein folding by the effects of macromolecular crowding. *Prot Sci* (2004), 13: 125-133.
20. Wenner J R and Bloomfield V A. Crowding Effects on EcoRV Kinetics and Binding. *Biophys J. Volume* 77 December 1999 3234-3241
21. Zhou B R, Liang Y, Du F, Zhou Z, Chen J. Mixed Macromolecular Crowding Accelerates the Oxidative Refolding of Reduced, Denatured Lysozyme: Implications for protein folding in intracellular environments *J Biol Chem,* 279, 2004, 55109-55116.
22. Zimmerman, S. B. and Harrison, B. (1987) Macromolecular crowding increases binding of DNA polymerase to DNA: an adaptive effect. *Proc. Natl. Acad. Sci. USA.*, 84, 1871-1875.
23. Zimmerman S B and Minton A P. Macromolecular crowding: Biochemical, Biophysical, and Physiological Consequences. *Ann. Rev. Biophys. Biomol. Struct.* 1993.22. 27-65.
24. WO0192501. 25. WO94/18333. 26. WO03053647. 27. US Patent Application US 20040241713A1. 28. U.S. Pat. No. 4,582,802. 29. U.S. Pat. No. 6,787,305. 30. U.S. Pat. No. 6,656,685. 31. U.S. Pat. No. 6,114,150. 32. U.S. Pat. No. 6,428,986. 33. U.S. Pat. No. 6,300,073. 34. U.S. Pat. No. 5,972,603.

The invention claimed is:

1. A method of nucleic acid synthesis or amplification, or of improving the efficiency, activity or stability of at least one nucleic acid-modifying enzyme, the method comprising at least one step of introducing at least two organic-based hydrophilic macromolecules having a molecular weight of 50 kDa to 500 kDa and neutral surface charge, wherein the at least two macromolecules are a combination of Ficoll 70 and Ficoll 400 present at a concentration of 2.5-25 mg/ml in a reaction mixture used in the method of nucleic acid synthesis or amplification, or of improving the efficiency, activity or stability of at least one nucleic acid-modifying enzyme, thereby synthesizing or amplifying a nucleic acid, or improving the efficiency, activity or stability of at least one nucleic acid-modifying enzyme.

2. The method of claim 1, wherein the macromolecule is a combination of Ficoll 70 present at a concentration of 7.5-15 mg/ml and Ficoll 400 present at a concentration of 2.5-5 mg/ml.

3. The method of claim 1, wherein the macromolecule is present in the form of a macromolecular solution with a viscosity of less than 2 mPa·s.

4. The method of claim 1, wherein the method is a RT-PCR.

5. A kit for nucleic acid synthesis, or amplification or for improving the efficiency, activity or stability of at least one nucleic acid-modifying enzyme, the kit comprising at least two organic-based hydrophilic macromolecules of molecular weight 50 kDa to 500 kDa and neutral surface charge wherein the at least two macromolecules are a combination of Ficoll 70 and Ficoll 400 present in the form of a solution at a concentration of 2.5-25 mg/ml and optionally at least one nucleic acid-modifying enzyme.

6. The kit of claim 5, wherein the macromolecule is a combination of Ficoll 70 solution at a concentration of 7.5-15 mg/ml and Ficoll 400 solution at a concentration of 2.5-5 mg/ml.

7. The kit of claim 5, wherein the macromolecule solution has a viscosity of less than 2 mPa·s.

8. A macromolecule solution for use in nucleic acid synthesis, or amplification or for improving the efficiency, activity or stability of an enzyme, the solution comprising at least two organic-based hydrophilic macromolecules having a molecular weight of 50 kDa to 500 kDa and neutral surface charge, wherein the at least two macromolecules are a combination of Ficoll 70 and Ficoll 400 present at a concentration of 2.5-25 mg/ml.

9. A method of determining the optimum crowding conditions in a method for nucleic acid synthesis, or amplification or for improving the efficiency, activity or stability of at least one nucleic acid-modifying enzyme, the method comprising:

providing at least two macromolecule candidates, wherein the at least two macromolecules are at least two organic-based hydrophilic macromolecules of molecular weight 50 kDa to 500 kDa and neutral surface charge, wherein the at least two macromolecules are a combination of Ficoll 70 and Ficoll 400 is present at a concentration of 2.5-25 mg/ml; introducing the at least two macromolecule candidates into a reaction mixture used in the method for nucleic acid synthesis, or amplification or for improving the efficiency, activity or stability of at least one nucleic acid-modifying enzyme; and determining the macromolecular concentration or macromolecular concentration range of the at least two macromolecule candidates that achieves optimum crowding with optimal volume exclusion effect and minimal viscosity changes of the at least two macromolecules in solution, which concentration or concentration range is the optimum crowding condition for nucleic acid synthesis, or amplification or for improving the efficiency, activity or stability of at least one nucleic acid-modifying enzyme.

10. The method of claim 9, wherein the determining of macromolecular concentration or macromolecular concentration range for optimum crowding is based on estimation of hydrodynamic radius of at least one macromolecule.

11. The method of claim 1, wherein the macromolecule has a radius range of 2 to 50 nm.

12. The method according to claim 1, wherein the method is PCR, RT-PCR or restriction digestion.

13. A method of nucleic acid synthesis or amplification, the method comprising: amplifying a DNA target sequence utilizing polymerase chain reaction (PCR) or reverse transcriptase-PCR in the presence of at least two different organic-based hydrophilic macromolecules having a molecular weight of 50 kDa to 500 kDa and neutral surface charge, wherein the at least two different macromolecules are Ficoll 70 and Ficoll 400 present at a total macromolecule concentration of 2.5-25 mg/ml.

14. A method of improving the efficiency, activity or stability of at least one nucleic acid-modifying enzyme in a polymerase chain reaction (PCR) or a reverse transcriptase-PCR, the method comprising: contacting at least one nucleic acid-modifying enzyme and at least two different organic-based hydrophilic macromolecules having a molecular weight of 50 kDa to 500 kDa and neutral surface charge, wherein the at least two different macromolecules are Ficoll 70 and Ficoll 400 present at a total macromolecule concentration of 2.5-25 mg/ml to thereby improve the efficiency, activity or stability of the at least one acid-modifying enzyme in a PCR or RT-PCR.

* * * * *